United States Patent [19]
Davidsen et al.

[11] Patent Number: 5,952,320
[45] Date of Patent: Sep. 14, 1999

[54] MACROCYCLIC INHIBITORS OF MATRIX METALLOPROTEINASES AND TNFα SECRETION

[75] Inventors: Steven K. Davidsen, Libertyville; Douglas H. Steinman, Morton Grove; George S. Sheppard, Wilmette; Lianhong Xu, Libertyville; James H. Holms; Yan Guo, both of Gurnee; James B. Summers, Libertyville; Alan S. Florjancic, Lake Bluff; Michael R. Michaelides, Gurnee, all of Ill.

[73] Assignee: Abbott Laboratories, Abbott Park, Ill.

[21] Appl. No.: 08/992,668

[22] Filed: Dec. 17, 1997

Related U.S. Application Data

[60] Provisional application No. 60/035,780, Jan. 7, 1997.

[51] Int. Cl.$^6$ .................. A61K 31/33; C07D 225/04; C07D 267/22; C07D 281/18
[52] U.S. Cl. .................. 514/183; 540/453; 540/454; 540/455; 540/456; 540/457; 540/458; 540/459; 540/460; 540/461; 540/463
[58] Field of Search ................... 540/453, 454, 540/455, 456, 457, 458, 459, 460, 461, 463; 514/183

[56] References Cited

U.S. PATENT DOCUMENTS

| | | | |
|---|---|---|---|
| 4,996,358 | 2/1991 | Handa et al. | 562/621 |
| 5,300,501 | 4/1994 | Porter | 514/238.2 |
| 5,442,110 | 8/1995 | Isomura et al. | 562/621 |

FOREIGN PATENT DOCUMENTS

| | | |
|---|---|---|
| 0489577 | 6/1992 | European Pat. Off. |
| 0498665 | 8/1992 | European Pat. Off. |
| 0575844 | 12/1993 | European Pat. Off. |
| 9102716 | 3/1991 | WIPO |
| 9213831 | 8/1992 | WIPO |
| 9324449 | 12/1993 | WIPO |
| 9402446 | 2/1994 | WIPO |
| 9402447 | 2/1994 | WIPO |
| 9410990 | 5/1994 | WIPO |
| 9421612 | 9/1994 | WIPO |
| 9422309 | 10/1994 | WIPO |
| 9424140 | 10/1994 | WIPO |
| 9425434 | 11/1994 | WIPO |
| 9504735 | 2/1995 | WIPO |
| 9506031 | 3/1995 | WIPO |
| 9519956 | 7/1995 | WIPO |
| 9519961 | 7/1995 | WIPO |
| 9522966 | 8/1995 | WIPO |
| 9523790 | 9/1995 | WIPO |
| 9529892 | 11/1995 | WIPO |
| 9532944 | 12/1995 | WIPO |
| 9616027 | 5/1996 | WIPO |
| 9616931 | 6/1996 | WIPO |
| 9633161 | 10/1996 | WIPO |
| 9718207 | 5/1997 | WIPO |

OTHER PUBLICATIONS

Nature vol. 370 Aug. 18, 1994, pp. 555–557 "Processing of tumor necrosis factor–α precursor by metalloproteinases."
Nature vol. 370 Jul. 21, 1994, pp. 218–220 "Protection against a lethal dose of endotoxin be an inhibitor of tumor necrosis factor processing."
Nature vol. 370 Aug. 18, 1994, pp. 558–561 "Regulation of tumour necrosis factor–α processing by a metalloproteinase inhibitor."
F.B. Ibrahim, "Quantitative Determination of Oxaprozin and Several of its Related Compounds by high Performance Reversed–Phase Liquid Chromatography", *J. Liq. Chromatogr.*, vol. 18, No. 13, (1995), 2621–2633.
J. Wyeth et al., "Identification of Impurities in a Novel Antiinflammatory Oxazole Derivative", *Proc. Soc. Anal. Chem.*, vol. 9, No. 2, (1972), pp.; 32–35.
K. Brown et al., Antiinflammatory 3–[4,5–bis (p–chlorophenyl) oxazol–2–yl] propionic acid and derivatives, Brit. 4 pp., Addn. to. Brit. 1,206,403. (abstract), 1974.
F.W. Short et al., Synthesis of 5–aryl–2–oxazolepropionic Acids Analogs. Antiinflammatory Agents, *J. Heterocycl. Chem.*, vol. 6, No. 5, (1969), pp. 707–712.
CAS Online printout of WO 97/18207, May 1997.

*Primary Examiner*—Mukund J. Shah
*Assistant Examiner*—Brenda Coleman
*Attorney, Agent, or Firm*—Gregory W. Steele

[57] ABSTRACT

Macrocyclic compounds of formula

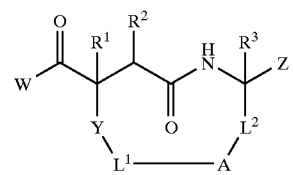

are potent inhibitors of matrix metalloproteinase and are useful in the treatment of diseases in which matrix metalloproteinase play a role. Also disclosed are matrix metalloproteinase inhibiting compositions and a method of inhibiting matrix metalloproteinase in a mammal.

13 Claims, No Drawings

MACROCYCLIC INHIBITORS OF MATRIX METALLOPROTEINASES AND TNFα SECRETION

This application claims the benefit of U.S. Provisional Application No. 60/035,780, filed Jan. 7, 1997.

TECHNICAL FIELD

This invention relates to compounds having activity to inhibit matrix metalloproteinases and TNFα secretion, to pharmaceutical compositions comprising these compounds, and to a medical method of treatment. More particularly, this invention concerns macrocyclic compounds which inhibit matrix metalloproteinases and TNFα secretion, to pharmaceutical compositions comprising these compounds and to a method of inhibiting matrix metalloproteinases and TNFα secretion.

BACKGROUND OF THE INVENTION

The matrix metalloproteinases (MMP's) are a class of extracellular enzymes including collagenase, stromelysin, and gelatinase which are believed to be involved in the tissue destruction which accompanies a large number of disease states varying from arthritis to cancer.

Typical connective tissue cells are embedded within an extracellular matrix of high molecular weight proteins and glycoproteins. In healthy tissue, there is a continual and delicately-balanced series of processes which include cell division, matrix synthesis, and matrix degradation. In certain pathological conditions, an imbalance of these three processes can lead to improper tissue restructuring. For example, in arthritis, joint mobility can be lost when there is improper remodelling of load-bearing joint cartilage. In the case of cancer, lack of coordination of cell division and the two processes of matrix synthesis and degradation can lead to conversion of transformed cells to invasive phenotypes in which increased matrix turnover permits tumor cells to penetrate basement membranes surrounding capillaries leading to subsequent metastasis.

There has been hightened interest in discovering therapeutic agents which bind to and inhibit MMP's. The discovery of new therapeutic agents possessing this activity will lead to new drugs having a novel mechanism of action for combatting disease states involving tissue degenerative processes including, for example, rheumatoid arthritis, osteoarthritis, osteopenias such as osteoporosis, periodontitis, gingivitis, corneal, epidermal or gastric ulceration, and tumor growth and metastasis or invasion.

Tumor Necrosis Factor α (TNFα) is a potent proinflammatory mediator which has been implicated in inflammatory conditions including arthritis, asthma, septic shock, non-insulin dependent diabetes mellitus and inflammatory bowel disease. TNFα is originally expressed as a membrane-bound protein of about 26 kD, which is proteolytically cleaved to release a soluble 17 kD fragment (TNFα processing) which combines with two other secreted TNFα molecules to form a circulating 51 kD homotrimer. Recently, several MMP inhibitors were found to inhibit TNFα processing (see Mohler, et al., *Nature*, 1994, 370, 218; Gearing, et al., *Nature*, 1994, 370, 555; and McGeehan, et al., *Nature*, 1994, 370, 558), leading to the hypothesis that TNFα processing is caused by an as yet uncharacterized metalloproteinase residing in the plasma membrane of cells producing TNFα. Inhibitors of this metalloproteinase would therefore be useful as therapeutics to treat disease states involving TNFα secretion.

Transforming growth factor alpha (TGFα) is a potent mitogen which ellicites its biological activity by binding to cell surface receptors, in particular epidermal growth factor (EGF) receptor. It is known to promote angiogenesis and to stimulate epithelial cell migration and therefore has been implicated in a number of malignant disorders such as breast cancer and ovarian carcinoma. TGFα is produced by proteolytic cleavage of a 160 amino acid membrane bound precursor. Several cleavage sites have been identified including Ala38-Val39, similar to the cleavage site of proTNFα (Ala-76-Val77). This common cleavage site suggests that inhibitors of TNFα processing may also block the cleavage of proTGFα and therefore would be therapeutically useful in diseases mediated by TGFα.

SUMMARY OF THE INVENTION

The present invention provides a novel class of macrocyclic inhibitors of matrix metalloproteinases and/or TNFα secretion.

In its principle embodiment, the present invention provides a macrocyclic compound of formula I

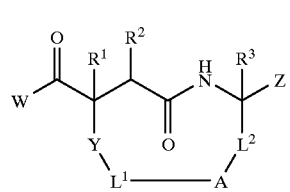

or a pharmaceutically acceptable salt, ester or prodrug thereof wherein

W is NHOH or OH.

$R^1$ and $R^3$ are independently selected from hydrogen or alkyl of one to four carbon atoms.

$R^2$ is selected from the group consisting of
  (a) alkyl of one to ten carbon atoms,
  (b) alkenyl of two to ten carbon atoms,
  (c) cycloalkyl of three to eight carbon atoms,
  (d) (cycloalkyl)alkyl wherein the cycloalkyl portion is of three to eight carbon atoms, and the alklene portion is of one to six carbon atoms,
  (e) cycloalkenylene of five to eight carbon atoms,
  (f) (cycloalkenylene)alkyl wherein the cycloalkenylene portion is of five to eight carbon atoms, and the alklene portion is of one to six carbon atoms,
  (g) phenyl,
  (h) phenyl substituted with 1, 2, or 3 substutuents independently selected from alkoxyalkyloxy, alkyl of one to four carbon atoms, alkoxy of one to four carbon atoms, halogen, haloalkyl of one to four carbon atoms, cyano, cyanoalkyl, —$CO_2R^4$ wherein $R^4$ is independently selected at each occurrence from hydrogen and alkyl of one to four carbon atoms, and —$CONR^4R^5$ wherein $R^4$ is defined above and and $R^5$ is independently selected at each occurrence from hydrogen and alkyl of one to four carbon atoms,
  (i) phenylalkyl wherein the alkylene portion is of one to six carbon atoms,
  (j) phenylalkyl wherein the alkylene portion is of one to six carbon atoms and the phenyl ring is substituted with 1, 2, or 3 substituents independently selected from alkoxyalkyloxy, alkyl of one to four carbon atoms, alkoxy of one to four carbon atoms, halogen, haloalkyl of one to four carbon atoms, cyano, cyanoalkyl, —CO$_2$R$^4$, —CONR$^4$R$^5$, phenyl, and phenyl substituted with 1, 2, or 3 substutuents independently selected from alkyl of one to four carbon atoms, hydroxy, alkoxy of one to four carbon atoms, halogen, haloalkyl of one to four carbon atoms, cyano. cyanoalkyl, —CO$_2$R$^4$, and —CONR$^4$R$^5$, (k) —(CH$_2$)$_m$—T—(CH$_2$)$_n$—R$^6$ wherein m and n are independently 0, 1, 2, 3 or 4, T is O or S, and R$^6$ is selected from the group consisting of alkyl of one to four carbon atoms, phenyl, and phenyl substituted with 1, 2, or 3 substituents selected from alkoxyalkyloxy, alkyl of one to four carbon atoms, hydroxy, alkoxy of one to four carbon atoms, halogen, haloalkyl of one to four carbon atoms, cyano, cyanoalkyl, —CO$_2$R$^4$, —CONR$^4$R$^5$, phenyl, and phenyl substituted with 1, 2, or 3 substutuents independently selected from alkyl of one to four carbon atoms, alkoxy of one to four carbon atoms, halogen, haloalkyl of one to four carbon atoms, cyano, cyanoalkyl, —CO$_2$R$^4$, and —CONR$^4$R$^5$, and (l) fluorenylalkyl wherein the alkylene portion is of one to four carbon atoms.

Y is absent or —O—.

L$^1$ is alkylene of two to six carbon atoms.

L$^2$ is selected from the group consisting of
(a) alkylene of one to six carbon atoms, and
(b)

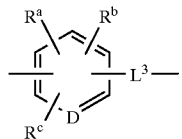

wherein D is CH or N, L$^3$ is absent or is alkylene of one to four carbon atoms, and R$^a$, R$^b$ and R$^c$ are independently selected from hydrogen, alkyl of one to four carbon atoms, hydroxy, alkoxy of one to four carbon atoms, halogen, haloalkyl of one to four carbon atoms, cyano, —SO$_2$R$^6$, wherein R$^6$, is alkyl of one to four carbon atoms, —SO$_2$NH$_2$, —CO$_2$R$^4$, 2-tetrazolyl, and —CONR$^7$R$^8$ wherein R$^7$ and R$^8$ are independently selected at each occurrence from hydrogen and alkyl of one to four carbon atoms, or R$^7$ and R$^8$ together with the N atom to which they are attached define a a 5- or 6-membered heterocyclic ring selected from the group consisting of morpholinyl, thiomorpholinyl, thiomorpholinyl sulfone, pyrrolidinyl, piperazinyl, piperidinyl, and 3-ketopiperazinyl.

A is absent or is selected from the group consisting of
(a) —O—,
(b) —NR$^9$— wherein R$^9$ is selected from the group consisting of
(1) hydrogen,
(2) alkyl of one to four carbon atoms,
(3) —CO$_2$R$^{10}$ wherein R$^{10}$ is independently selected at each occurrence from the group consisting of alkyl of one to four carbon atoms, haloalkyl of one to four carbon atoms, phenyl, phenyl substituted with 1, 2, or 3 substituents independently selected from alkyl of one to four carbon atoms, alkoxy of one to four carbon atoms, halogen, haloalkyl of one to four carbon atoms, nitro, cyano, cyanoalkyl, —SO$_2$NH$_2$, —CO$_2$R$^4$, and —CONR$^4$R$^5$, phenylalkyl wherein the alkylene portion is of one to four carbon atoms, phenylalkyl wherein the alkylene portion is of one to four carbon atoms, and the phenyl ring is substituted with 1, 2, or 3 substituents independently selected from alkyl of one to four carbon atoms, alkoxy of one to four carbon atoms, halogen, haloalkyl of one to four carbon atoms, cyano, cyanoalkyl, —SO$_2$NH$_2$, —CO$_2$R$^4$, and —CONR$^4$R$^5$, heteroarylalkyl wherein the alkylene portion is of one to four carbon atoms, and the heteroaryl group is selected from furyl, pyridyl, thienyl, benzimidazolyl, imidazolyl, thiazolyl, and benzothiazolyl wherein the heteroaryl group is unsubstituted or substituted with alkyl of one to four carbon atoms, (4) —CONR$^7$R$^8$,
(5) —COR$^{10}$, and
(6) —SO$_2$R$^{10}$, (c) —S(O)$_n$, —wherein n, is 0, 1, or 2,
(d) —S—S—
(e) —CH=CH—,
(f)

wherein V is O or NOR$^4$,
(g)

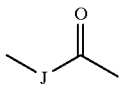

wherein J is O or NR$^4$,
(h)

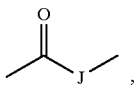

(i)

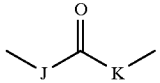

wherein J is defined above and K is selected from O and NR$^4$, provided that J and K are not simultaneously O, (j)

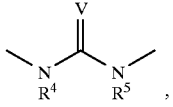

(k)

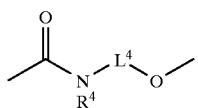

wherein $L^4$ is alkylene of two to six carbon atoms, (l)

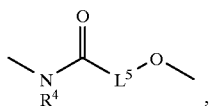

wherein $L^5$ is alkylene of one to three carbon atoms, (m)

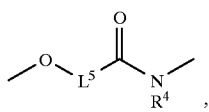

(n)

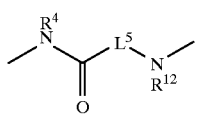

wherein $R^4$ is defined above and $R^{12}$ is selected from hydrogen, alkyl of one to four carbon atoms, —$COR^{10}$, —$CO_2R^{10}$, and —$SO_2R^{10}$, (o)

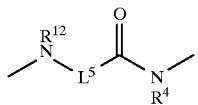

(p)

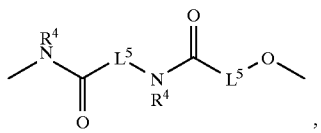

(q)

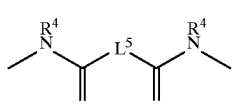

(r)

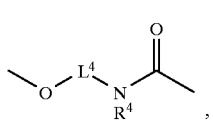

(s)

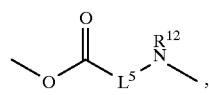

(t)

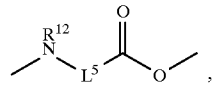

(u)

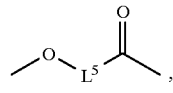

(v)

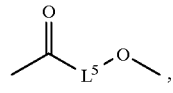

(w) —J'—$L^4$—K'— wherein J' and K' are independently selected from O and $NR^{12}$, (x) —$NR^4SO_2$—, (y) —$SO_2NR^4$—, (z) —$NR^4SO_2NR^5$—, (aa)

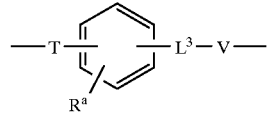

wherein T and V are independently selected from O and S and $R^a$ is defined above, (bb)

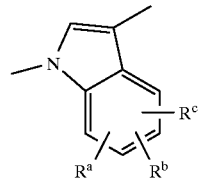

wherein $R^a$, $R^b$, and $R^c$ are defined above, (cc)

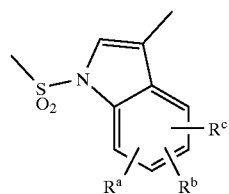

(dd)

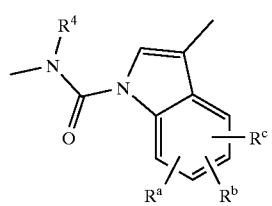

-continued (ee)
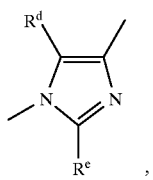

wherein $R^d$ and $R^e$ are independently selected from hydrogen and alkyl of one to four carbon atoms, and (ff)
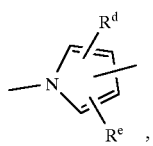

provided that when A is selected from (aa), (bb), (cc), (dd) and (ff) above, $L^2$ is alkylene, and further provided that when both Y and A are absent, L1 is alkylene of three to six carbon atoms.

Z is absent or is selected from the group consisting of
(a) —CO$_2$H,
(b) —CO$_2$R$^{10}$,
(c)

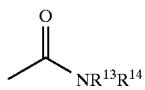

wherein $R^{13}$ is hydrogen or alkyl of one to six carbon atoms, and $R^{14}$ is selected from the group consisting of
(1) hydrogen,
(2) alkyl of one to six carbon atoms,
(3) cycloalkyl of three to eight carbon atoms,
(4) (cycloalkyl)alkyl wherein the cycloalkyl portion is of three to eight carbon atoms and the alkyl portion is of one to four carbon atoms,
(5) cycloalkenyl of five to eight carbon atoms,
(6) (cycloalkenyl)alkyl wherein the cycloalkenyl portion is of five to eight carbon atoms and the alkyl portion is of one to four carbon atoms,
(7) —SO$_2$R$^{10}$,
(8) —CH$_2$CH$_2$M(L$^3$M)$_p$—R$^4$ wherein p is 1, 2 or 3, L$^3$ is alkylene of from one to four carbon atoms and M is selected at each occurrence from O and S,
(9) —L$^4$—(NR$^4$L$^4$)$_q$—NR$^7$R$^8$ wherein q is 0, 1 or 2,
(10) —L$^4$—(NR$^4$L$^4$)$_q$—NR$^4$SO$_2$NR$^7$R$^8$,
(11) aryl wherein the aryl group is selected from (a) phenyl, (b) phenyl substituted with 1, 2, or 3 substituents selected from alkyl of one to four carbon atoms, halogen, haloalkyl of one to four carbon atoms, hydroxy, alkoxy of one to four carbon atoms, cyano, —C(O)R$^4$, —NR$^4$R$^5$, —CO$_2$R$^4$, —SO$_2$R$^4$, —SO$_2$NR$^4$R$^5$phenyl wherein the phenyl ring may be substituted with 1, 2, or 3 substituents independently selected from alkyl of one to four carbon atoms, halogen, haloalkyl of one to four carbon atoms, and benzylloxy, (c) naphthyl, (d) naphthyl substituted with 1, 2 or 3 substituents independently selected from alkyl of one to four carbon atoms, halogen, haloalkyl of one to four carbon atoms, hydroxy, alkoxy of one to four carbon atoms, cyano, —C(O)R$^4$, —NR$^4$R$^5$, —CO$_2$R$^4$, —SO$_2$R$^4$, —SO$_2$NR$^4$R$^5$,
(12) heteroaryl selected from the group consisting of (a) pyridyl, (b) thiazolyl, (c) furyl, (d) thienyl, (e) pyrrolyl, (f) tetrahydrofuryl, (g) imidazolyl, (h) phenylthiazolyl, (i) benzothiazolyl, (j) benzimidazolyl, (k) pyrazinyl, (l) pyrimidyl, (m) quinolyl, (n) piperazinyl, and (o) indolyl wherein the heteroaryl group is unsubstituted or substituted with alkyl of one to four carbon atoms,
(13) arylalkyl wherein the alkylene portion is of one to four carbon atoms and the aryl group is defined above,
(14) heteroarylalkyl wherein the alkylene portion is of one to four carbon atoms and the heteroaryl group is defined above,

(15)
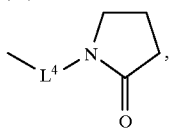

(16)
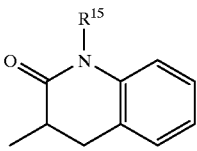

wherein $R^{15}$ is selected from hydrogen, hydroxy, alkyl of one to four carbon atoms, alkoxy of one to four carbon atoms, and alkoxyalkyl of one to four carbon atoms, and

(17)
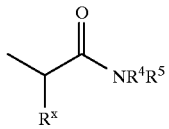

wherein $R^x$ is the side chain of a naturally occurring amino acid,

(18)
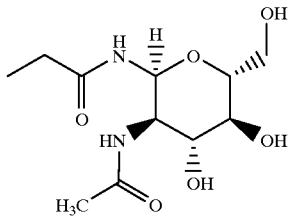

or $R^{13}$ and $R^{14}$, together with the N atom to which they are attached define a 5- or 6-membered heterocyclic ring selected the group consisting of
(1) morpholinyl,
(2) thiomorpholinyl,
(3) thiomorpholinyl sulfone, (4) pyrrolidinyl,
(5) piperazinyl,
(6) piperidinyl,
(7) 3-ketopiperazinyl, and
(8)

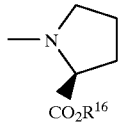

wherein $R^{16}$ is hydrogen or benzyl, and (d)

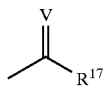

wherein V is defined above and $R^{17}$ is selected from the group consisting of
(1) alkyl of one to six carbon atoms,
(2) carboxyalkyl wherein the alkylene portion is of two to six carbon atoms,
(3) phenyl,
(4) phenyl substituted with 1, 2, or 3 substituents selected from alkyl of one to four carbon atoms, halogen, hydroxy, hydroxyalkyl of one to four carbon atoms, haloalkyl of one to four carbon atoms, alkoxy of one to four carbon atoms, amino, cyano, $-NR^4R^5$, $-SO_2NR^4R^5$, $-SO_2R^4$, $-CH_2NR^7R^8$, $-CONR^7R^8$, $-CO_2R^4$, and phenyl, wherein the phenyl ring may be substituted with 1, 2, or 3 substituents independently selected from alkyl of one to four carbon atoms, halogen, and haloalkyl of one to four carbon atoms,
(5) 1,3-benzodioxole,
(6) indolyl,
(7) indolyl substituted with alkyl of one to four carbon atoms, halogen, haloalkyl of one to four carbon atoms, alkoxy of one to four carbon atoms, $-SO_2NR^4R^5$, $-CO_2R^{10}$, and phenyl, wherein the phenyl ring may be substituted with 1, 2, or 3 substituents independently selected from alkyl of one to four carbon atoms, halogen, haloalkyl of one to four carbon atoms, and alkoxy of one to four carbon atoms,
(8) pyrrolyl,
(9) pyrrolyl substituted with alkyl of one to four carbon atoms,
(10) imidazolyl.
(11) imidazolyl substituted with alkyl of one to four carbon atoms, provided that in (6)–(11) above, when the heterocycle is attached at a carbon atom, the N atom may bear a substituent selected from the group consisting of alkyl of one to six carbon atoms $-CONR^7R^8$, $-SO_2NR^7R^8$ and $-SO_2R^{10}$,
(12) pyridyl,
(13) pyridyl substituted with alkyl of one to four carbon atoms,
(14) thienyl,
(15) thienyl substituted with halogen, alkyl of one to four carbon atoms, and haloalkyl of one to four carbon atoms,
(16) thiazolyl,
(17) thiazolyl substituted with halogen, alkyl of one to four carbon atoms, and haloalkyl of one to four carbon atoms,
(18) oxazolyl,
(19) oxazolyl substituted with halogen, alkyl of one to four carbon atoms, and haloalkyl of one to four carbon atoms,
(20) furyl,
(21) furyl substituted with halogen, alkyl of one to four carbon atoms, and haloalkyl of one to four carbon atoms,
(22) benzofuryl,
(23) benzofuryl substituted with 1, 2, or 3 substituents selected from alkyl of one to four carbon atoms, halogen, and haloalkyl of one to four carbon atoms,
(24) benzothiazolyl,
(25) benzothiazolyl substituted with 1, 2, or 3 substituents selected from alkyl of one to four carbon atoms, halogen, and haloalkyl of one to four carbon atoms,
(26) benzimidazolyl and
(27) benzimidazolyl substituted with 1, 2 or 3 substituents independently selected from alkyl of one to four carbon atoms, halogen, and haloalkyl of one to four carbon atoms, (e)

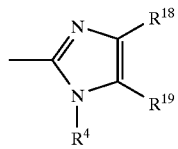

wherein $R^{18}$ and $R^{19}$ are independently selected from the group consisting of
(1) alkyl of one to four carbon atoms,
(2) halogen,
(3) haloalkyl of one to four carbon atoms,
(4) alkoxyalkyl wherein the alkoxy and alkylene portions are independently of one to six carbon atoms,
(5) alkanoyl of one to six carbon atoms,
(6) $-CH(OH)R^4$,
(7) $-CONR^4R^5$,
(8) $-CO_2R^4$,
(9) phenyl,
(10) phenyl substituted with 1, 2, or 3 substituents selected from alkyl of one to four carbon atoms, halogen, hydroxy, haloalkyl of one to four carbon atoms, alkoxy of one to four carbon atoms, amino, cyano, $-SO_2NR^4R^5$, $-SO_2R^4$, $-CH_2NR^4R^5$, $-CONR^4R^5$, and $-CO_2R^4$ or $R^{18}$ and $R^{19}$ together with the carbon atoms to which they are attached define a fused 5-7 membered carbocyclic aryl or heterocyclic aryl ring wherein the ring may be substituted with alkyl of one to four carbon atoms or haloalkyl of one to four carbon atoms.

In another aspect, the present invention provides pharmaceutical compositions which comprise a therapeutically effective amount of compound of formula I in combination with a pharmaceutically acceptable carrier.

In yet another aspect, the present invention provides a method of inhibiting matrix metalloproteinases and/or TNFα secretion in a host mammal in need of such treatment comprising administering to a mammal in need of such treatment a therapeutically effective amount of a compound of formula I.

DETAILED DESCRIPTION

As used throughout this specification and the appended claims, the following terms have the meanings specified.

The term alkyl refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "alkanoyl" represents an alkyl group, as defined above, attached to the parent molecular moiety through a carbonyl group. Alkanoyl groups are exemplified by formyl, acetyl, propionyl, butanoyl and the like.

The terms alkoxy and alkoxyl denote an alkyl group, as defined above, attached to the parent molecular moiety through an oxygen atom. Representative alkoxy groups include methoxy, ethoxy, propoxy, butoxy, and the like.

The term "alkoxycarbonyl" represents an ester group; i.e. an alkoxy group, attached to the parent molecular moiety through a carbonyl group such as methoxycarbonyl, ethoxycarbonyl, and the like.

The term alkenyl as used herein refer to monovalent straight or branched chain groups of 2 to 6 carbon atoms containing a carbon-carbon double bond, derived from an alkene by the removal of one hydrogen atom and include, but are not limited to groups such as ethenyl, 1-propenyl, 2-propenyl, 2-methyl-1-propenyl, 1-butenyl, 2-butenyl and the like.

The term alkylene denotes a saturated divalent hydrocarbon group derived from a straight or branched chain saturated hydrocarbon containing by the removal of two hydrogen atoms, for example —$CH_2$—, —$CH_2CH_2$—, —CH($CH_3$)$CH_2$— and the like.

The term alkenylene denotes a divalent group derived from a straight or branched chain hydrocarbon containing at least one carbon-carbon double bond. Examples of alkenylene include —CH=CH—, —$CH_2$CH=CH—, —C($CH_3$)=CH—, —$CH_2$CH=CH$CH_2$—, and the like.

The terms alkynylene refers to a divalent group derived by the removal of two hydrogen atoms from a straight or branched chain acyclic hydrocarbon group containing at least one carbon-carbon triple bond. Examples of alkynylene include —CH≡CH—, —CH≡C—$CH_2$—, —CH≡CH—CH($CH_3$)— and the like.

The term "benzyloxy" as used herein refers to O-alkylene-phenyl wherein in the alkylene is of one to four carbons.

The term cycloalkyl as used herein refers to a monovalent saturated cyclic hydrocarbon group. Representative cycloalkyl groups include cyclopropyl, cyclobutyl, cyclopentyl, cyclohexyl, cycloheptyl, bicyclo[2.2.1]heptane and the like.

Cycloalkylene denotes a divalent radical derived from a cycloalkane by the removal of two hydrogen atoms.

The terms "(cycloalkyl)alkyl" and "(cycloalkenylene) alkyl" refer, respectively, to a cycloalkyl group or cycloalkenylene group as defined above attached to the parent molecular moiety through an alkylene group.

The term cyanoalkyl denotes an alkyl group, as defined above, substituted by a cyano group and includes, for example, cyanomethyl, cyanoethyl, cyanopropyl and the like.

The term haloalkyl denotes an alkyl group, as defined above, having one, two, or three halogen atoms attached thereto and is exemplified by such groups as chloromethyl, bromoethyl, trifluoromethyl, and the like.

The term "hydroxyalkyl" represents an alkyl group, as defined above, substituted by one to three hydroxyl groups with the proviso that no more than one hydroxy group may be attached to a single carbon atom of the alkyl group.

The term "phenoxy" refers to a phenyl group attached to the parent molecular moiety through an oxygen atom.

By pharmaceutically acceptable salt is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M Berge, et al. describe pharmaceutically acceptable salts in detail in *J. Pharmaceutical Sciences*, 1977, 66:1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyates, acrylates and ethylsuccinates.

The term "pharmaceutically acceptable prodrugs" as used herein refers to those prodrugs of the compounds of the present invention which are, within the scope of sound medical judgement, suitable for use in contact with with the tissues of humans and lower animals with undue toxicity, irritation, allergic response, and the like commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche. ed., *Bioreversible Carriers in Drug Design*, American Pharmaceutical Association and Pergamon Press, 1987, both of which are incorporated herein by reference.

Asymmetric centers may exist in the compounds of the present invention. The present invention contemplates the various stereoisomers and mixtures thereof. Individual stereoisomers of compounds of the present invention are made by synthesis from starting materials containing the chiral centers or by preparation of mixtures of enantiomeric products followed by separation as, for example, by conversion to a mixture of diastereomers followed by separation by recrystallization or chromatographic techniques, or by direct separation of the optical enantiomers on chiral chromatographic columns. Starting compounds of particular stereochemistry are either commercially available or are made by the methods detailed below and resolved by techniques well known in the organic chemical arts.

Preferred Embodiments

Preferred compounds of the present invention have formula II

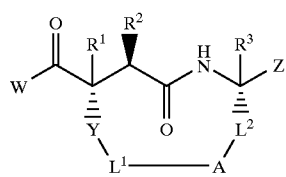

II wherein W and $L^2$ are defined above,

Y is absent or —O—;

$R^1$ and $R^3$ are H;

$L^1$ is alkylene of two to six carbon atoms:

A is selected from the group consisting of
(a) —O—,
(b) —$NR^9$— wherein $R^9$ is selected from the group consisting of
  (1) hydrogen,
  (2) alkyl of one to four carbon atoms,
  (3) —$CO_2R^{10}$ wherein $R^{10}$ is independently selected at each occurrence from the group consisting of alkyl of one to four carbon atoms, phenyl, phenyl substituted with 1, 2, or 3 substituents independently selected from alkyl of one to four carbon atoms, alkoxy of one to four carbon atoms, halogen, haloalkyl of one to four carbon atoms, nitro, cyano, cyanoalkyl, —$SO_2NH_2$, —$CO_2R^4$, and —$CONR^4R^5$, phenylalkyl wherein the alkylene portion is of one to four carbon atoms, phenylalkyl wherein the alkylene portion is of one to four carbon atoms, and the phenyl ring is substituted with 1, 2, or 3 substituents independently selected from alkyl of one to four carbon atoms, alkoxy of one to four carbon atoms, halogen, haloalkyl of one to four carbon atoms, cyano cyanoalkyl, —$SO_2NH_2$, —$CO_2R^4$, and —$CONR^4R^5$, and
  (4) —$SO_2R^{10}$,
(c) —CH═CH—,
(d)

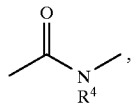

(e)

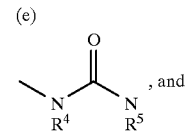
, and (f)

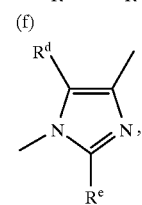

wherein $R^d$ and $R^e$ are independently selected from hydrogen and alkyl of one to four carbon atoms, provided that when A is (f) above, $L^2$ is alkylene;

$R^2$ is selected from the group consisting of isobutyl, cyclohexyl, cyclopentylmethyl, phenyl, 3-(4-tolyl)propyl, 3-(4-chlorophenyl)propyl, 2-(4-propylphenyl)ethyl, 3-benzyloxypropyl, 4-phenoxybutyl, 4-(4-butylphenoxy)butyl, 4-biphenyloxy, and 2-(4-(4'cyano)biphenyloxy)ethyl; and Z is absent or is selected from the group consisting of
(a) —$CO_2H$,
(b) —$CO_2R^{10}$,
(c)

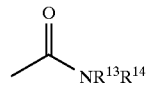

wherein $R^{13}$ is hydrogen or alkyl of one to six carbon atoms, and $R^{14}$ is selected from the group consisting of
(1) hydrogen,
(2) alkyl of one to four carbon atoms,
(3) 2-phenylethyl,
(4) 2-(4-aminosulfonyl)phenylethyl,
(5) cyclopropyl,
(6) phenyl,
(7) phenylsulfonyl,
(8) 2-thiomethylethyl,
(9) 2-dimethylaminoethyl,
(10) —$(CH_2)_2OCH_2O(CH_2)_2OCH_3$,
(11) 2-morpholinylethyl,
(12) 4-pyridinylethyl,
(13) 2-furylmethyl,
(14) 2-pyridyl,
(15) 2-thiazolyl, (16)

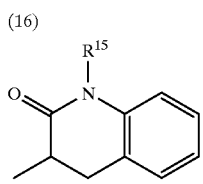

wherein $R^{15}$ is hydrogen, and

(17) 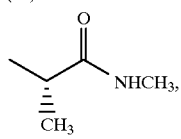

or $R^{13}$ and $R^{14}$, together with the N atom to which they are attached define a 5- or 6-membered heterocyclic ring selected the group consisting of morpholinyl, pyrrolidinyl, piperidinyl, and

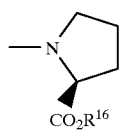

wherein $R^{16}$ is hydrogen or benzyl, (d) 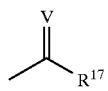

wherein V is defined above and $R^{17}$ is selected from the group consisting of
(1) phenyl,
(2) phenyl substituted with alkyl of one to four carbon atoms, methanesulfonyl or dimethylaminomethyl,
(3) 3-indolyl,
(4) 2-pyrrolyl, and
(5) 1-dimethylaminocarbamoylindol-3-yl, (e)

(f)

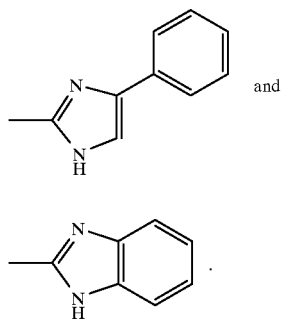

More preferred compounds of the present invention have formula II wherein W is —NHOH.

Still more preferred compounds have formula II wherein Y, $R^1$, $R^3$, $L^1$ and A are defined above; $R^2$ is selected from isobutyl, 3-(4-tolyl)propyl, 2-(4-propylphenyl)ethyl; and Z is absent or is selected from the group consisting of —CO₂H, —CO₂CH₃, —CO₂benzyl, —CONHCH₃, —CON(CH₃)₂,

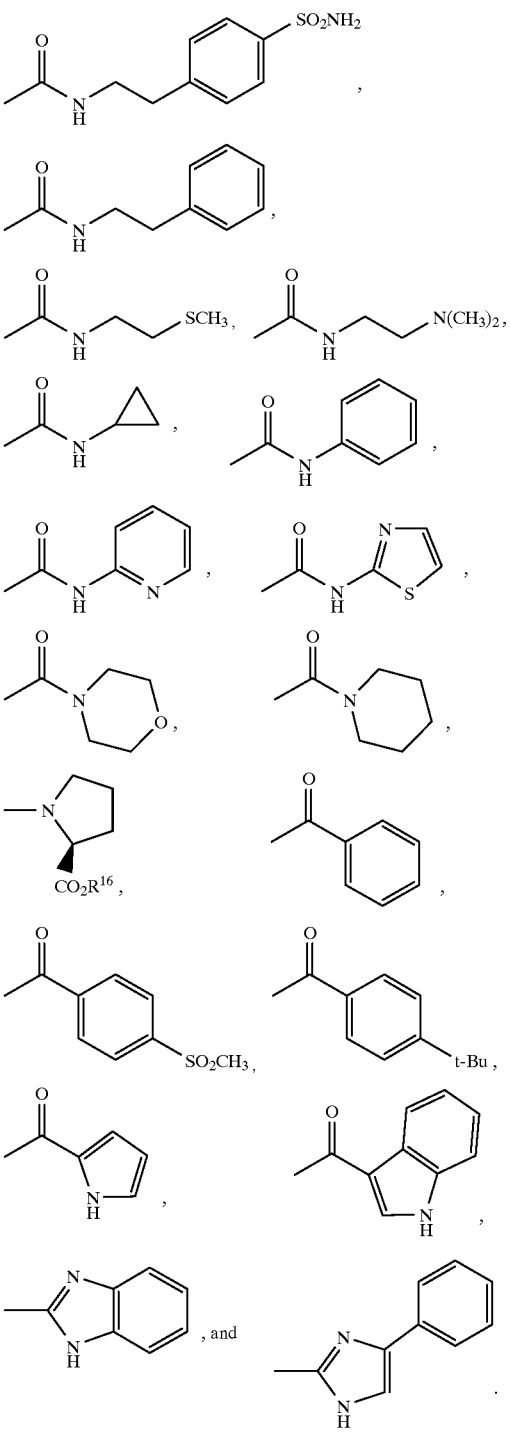

Still yet more preferred compounds have the formula II wherein W is —NHOH and Z is —CONHCH₃.

The most preferred compounds of the present invention have formula III

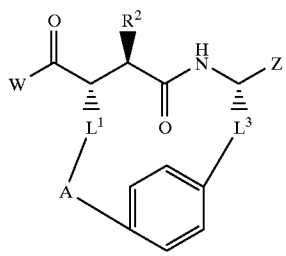

wherein

W is NHOH;

$L^1$ is alkylene of two to six carbon atoms;

$L^3$ is absent or methylene;

A is selected from the group consisting of
(a) —O—,
(b) —$NR^9$— wherein $R^9$ is selected from hydrogen, —$CO_2$benzyl, —$SO_2CH_3$, —$SO_2$-(4-tolyl),
(c) —CH=CH—, and
(d) —C(O)NH—;

$R^2$ is selected from isobutyl, 3-(4-tolyl)propyl, 2-(4-propylphenyl)ethyl; and Z is is selected from the group consisting of —$CONHCH_3$, —$CON(CH_3)_2$,

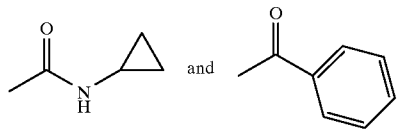

Determination of Stromelysin Inhibition

The efficacy of the compounds of this invention as matrix metalloproteinase inhibitors was determined by measuring the inhibition of stromelysin. The inhibition of stromelysin by the compounds of this invention was determined as follows: Recombinant truncated stromelysin (human sequence) produced in *E. coli* was prepared by expression and purification of the protein as described by Ye et al., *Biochemistry*, 1992, 31, 11231–11235. The enzyme was assayed by its cleavage of the thiopeptide ester substrate Ac-Pro-Leu-Gly-[2-mercapto-4-methyl-pentanoyl]-Leu-Gly-OEt described by Weingarten and Feder, *Anal. Biochem.*, 1985, 147, 437–440 (1985), as a substrate of vertebrate collagenase. The reported conditions were modified to allow assays to be carried out in a microtiter plate. Upon hydrolysis of the thioester bond, the released thiol group reacts rapidly with 5,5'-dithio-bis(2-nitrobenzoic acid) (DTNB), producing a yellow color which is measured by a microtiter plate reader set at 405 nm. The rates of cleavage of the substrate by stromelysin in the presence or absence of inhibitors are measured in a 30 min assay at ambient temperature. Solutions of the compounds in DMSO are prepared, and these are diluted at various concentrations into the assay buffer (50 mM MES/NaOH pH 6.5 with 10 mM $CaCl_2$ and 0.2% Pluronic F-68), which is also used for dilution of the enzyme and substrate. The potency of the compounds [$IC_{50}$] are calculated from the inhibition/inhibitor concentration data. The compounds of this invention inhibit stromelysin as shown by the data for representative examples in Table 1.

TABLE 1

Inhibitory Potencies against Stromelysin of Representative Compounds

| Example | $IC_{50}$ (nM) |
| --- | --- |
| 1 | 6.9 |
| 2 | 7.2 |
| 3 | 5.8 |
| 4 | 2.4 |
| 5 | 9.3 |
| 6 | 2.6 |
| 7 | 3.6 |
| 8 syn | 570 |
| 8 anti | 3.9 |
| 9 | 2100 |
| 10 | 7.8 |
| 11 | 6.1 |
| 12 | 12 |
| 13 | 2.4 |
| 14 | 2.7 |
| 15 | 7.2 |
| 16 | 23 |
| 18 | 0.61 |
| 19 | 20 |
| 20 | 92 |
| 21 | 39 |
| 23 | 8.1 |
| 24 | 8.9 |
| 25 | 44 |
| 26 | 27 |
| 30 | 20 |
| 31 | 2.9 |
| 32 | 6.7 |
| 34 | 1.5 |
| 38 | 0.56 |
| 41 | 26 |

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions. suspensions, syrups and elixirs. In addition to the active compounds, the liquid dosage forms may contain inert diluents commonly used in the art such as, for example. water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain. in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of Compounds of this Invention

The compounds of this invention may be prepared by a variety of synthetic routes. Representative procedures are outlined in the following Schemes 1–10. It is understood that while the following schemes describe the preparation of macrocycles predominately derived from tyrosine, the substitution of any of a number of both natural and unnatural amino acids will result in the formation of the desired macrocycles.

Abbreviations which have been used in the descriptions of the schemes and the examples that follow are: THF for tetrahydrofuran; DMF for N,N-dimethylformamide, ETOAc for ethyl acetate: Et$_2$O for diethyl ether, IPA for isopropanol; ETOH for ethanols MeOH for methanol: AcOH for acetic acid; HOBT for 1-hydroxybenzotriazole hydrdate; EDC for 1-(3-dimethylaminopropyl)-3-ethylcarbodiimide hydrochloride; Ms for methyl sulfonate; NMM for N-methylmorpholine; Bu$_3$P for tributylphosphine; ADDP for 1,1'-(azodicarbonyl)dipiperidine; and DMPU for 1,3-dimethyl-3,4,5,6-tetrahydro-2(1 H)-pyrimidinone.

The preparation of compounds of formula 6, wherein W is —OH and 7, wherein W is —NHOH and R$^1$, R$^2$, R$^3$, R$^{13}$ and R$^{14}$ are defined above is described in Schemes 1a and b. According to Scheme 1a, coupling of acid 1 with amino amide 2 in the presence of an tertiary amine base, hydroxybenzotriazole (HOBt), and a suitable coupling agent such as 1-(3-dimethylaminopropyl)-3-ethylcarbodiimide hydrochloride (EDCI.HCl) provides amide 3. Hydroboration of 3 using, for example, a tetrahydrofuran solution of borane followed by work up with aqueous hydrogen peroxide gives alcohol 4. Cyclization of 4 can be achieved using Mitsunobu conditions (Mitsunobu et al., *J. Am. Chem. Soc.*, 1972, 94, 679). For example addition of 4 to a solution of triphenylphosphine and diethylazodicarboxylate gives macrocycle 5. Conversion of 5 to the corresponding carboxylic acid 6 is accomplished by acidic removal of the tert-butyl ester with, for example, trifluoroacetic acid or hydrogen chloride in dioxane. Treatment of this acid with hydroxylamine or a hydroxylamine equivalent such as O-tert-butyldimethylsilylhydroxylamine in the presence of a suitable coupling agent such as EDCI.HCl gives hydroxamate 7. O-Benzylhydroxylamine can also be employed in this coupling reaction.

The resulting O-benzylhydroxamate can then be treated with hydrogen and a palladium catalyst such as 10% palladium on carbon to produce hydroxamate 77.

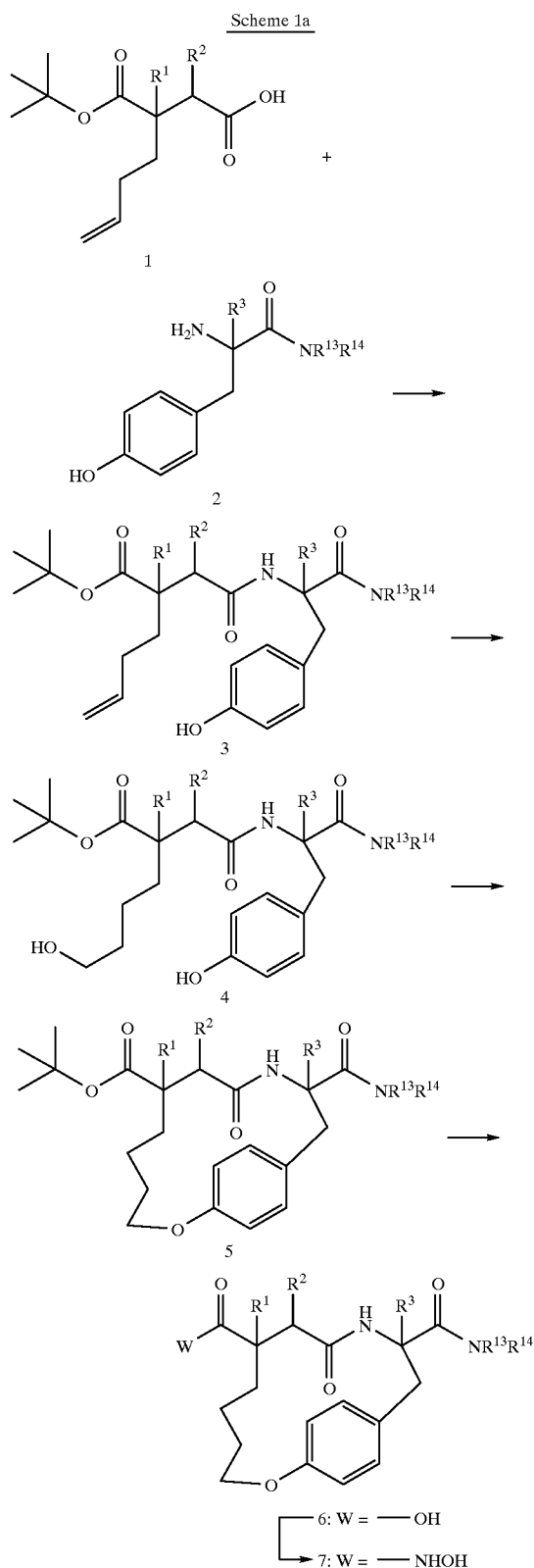

Scheme 1a

An alternative route hydroxamate 7, as outlined in Scheme 1b, involves reaction of acid 1 with the benzyl ester analog of 2 under the conditions used to prepare 3. The resulting amide 8 is subjected to the cyclization conditions described above followed by hydrogenolylic removal of the benzyl ester giving carboxylic acid 9. Treatment of 9 with EDCI.HCl. HOBt, N-methlmorpholine, and a primary or secondary amine of the formula HNR$^{13}$R$^{14}$ gives amide 5 which can be converted to hydroxamate 7 as described above.

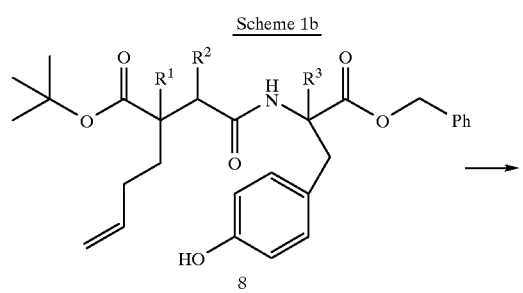

Scheme 1b

8

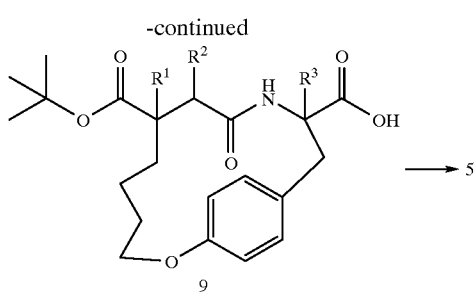

9

Preparation of intermediate 2 is accomplished by treating commercially available acid 10 with the requisite amine general formula HNR$^{13}$R$^{14}$ using, for example, EDCI.HCl, HOBt, and N-methylmorpholine as shown in Scheme 2. The resulting amide 11 is subjected to acidic removal of the N-t-butoxycarbonyl nitrogen protecting group using trifluoroacetic acid or hydrogen chloride in dioaxane giving amide 2. Amino ketones of the general formula 15 are prepared by treating acid 12 with ethereal diazomethane to produce methyl ester 13. This compound is subsequently reacted with a anion such as R$^{17}$MgX wherein X is Br, Cl or I, or R$^{17}$Li to generate ketone 14. Acidic removal of the tert-butyl protecting groups gives amino ketone 15. Alternatively, carboxylic acid 12 can be treated with a carbon anion such as phenyllithium which gives 14 directly. Amino ketone 15 can be used in place of amino amide 2 in Scheme I for the preparation of macrocyclic compounds where "Z"=— COR$^{17}$.

Scheme 2

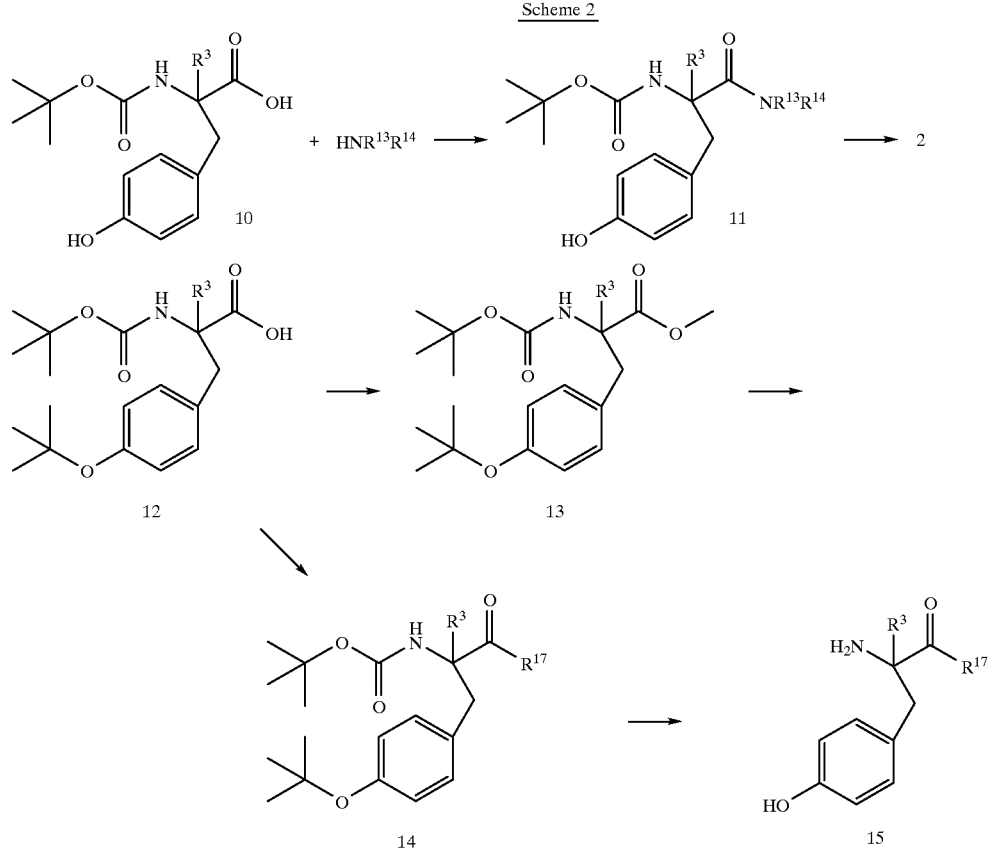

The preparation of intermediate 1 is shown in Scheme 3. Treatment of oxazolidinone 16 with a suitable base such as lithium diisopropylamide followed by addition of tert-butyl bromoacetate and basic hydrolysis gives carboxylic acid 17. This acid is treated with at least two equivalents of a strong base such as lithium diisopropylamide followed by an alkenyl halide such as 4-bromo-1-butene. The resulting dialkyl succinate 18 is again treated with a strong base such as lithium diisopropylamide followed by either methanol ($R^1$=H) or an alkyl halide ($R^1$=alkyl) such as methyl iodide giving substituted succinate 1.

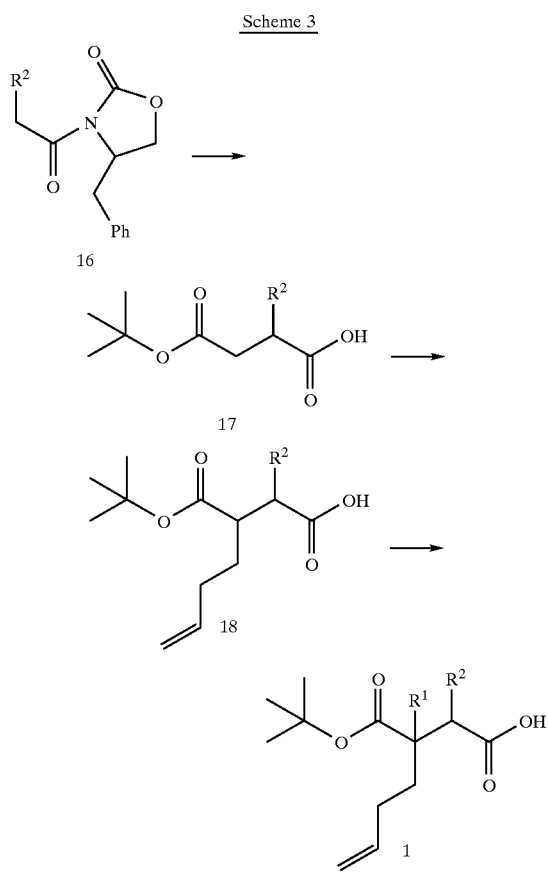

Preparation of compounds of this invention where "Y" is —O— is shown in Scheme 4. The known acetonide 19 (British Biotechnology PCT application WO 94/02446) is first treated with a base such as potassium carbonate then with an alkenyl halide such as allyl bromide. Acidic removal of the acetonide group using, for instance, aqueous hydrogen chloride gives the corresponding hydroxy acid which is subjected to treatment with a base such as potassium carbonate and benzyl bromide giving alcohol 20. O-Alkylation of 20 using sodium hydride and allyl bromide followed by palladium catalyzed ester deprotection using, for instance, tetrakis(triphenylphosphine)palladium (0) gives allyl ether 21. Coupling of 21 with 2, followed by hybroboration and cyclization as described in Scheme 1 above provides macrocycle 22. Hydrogenolylic removed of the benzyl ester using, for instance, hydrogen and 10% palladium on carbon gives acid 23 which can be converted to macrocyclic hydroxamate 24 as described above.

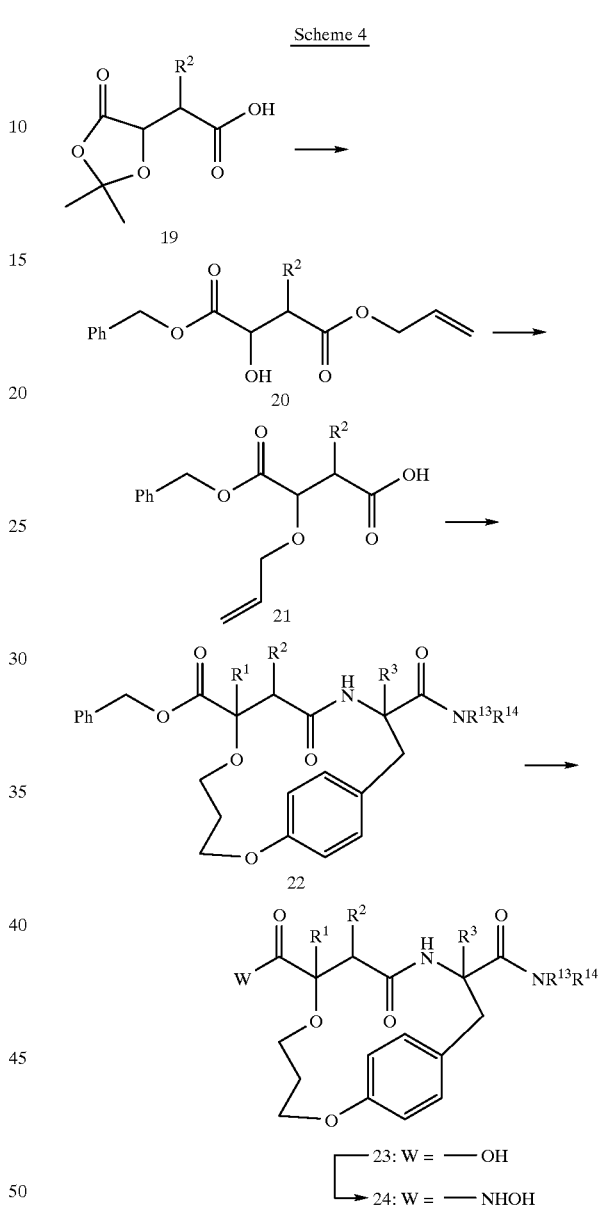

Benzimidazole-containing macrocycles are prepared according to Scheme 5. o-Amino amide 25, prepared as described in Scheme 1 wherein $HNR^{13}R^{14}$ is 1,2-phenylenediamine, is heated with an acid such as camphor sulfonic acid to generate benzimidazole 26. Conversion of this compound to the corresponding carboxylic acid 27 and hydroxamate 28 is accomplished by analogy with the sequence shown in Scheme 1.

Scheme 5

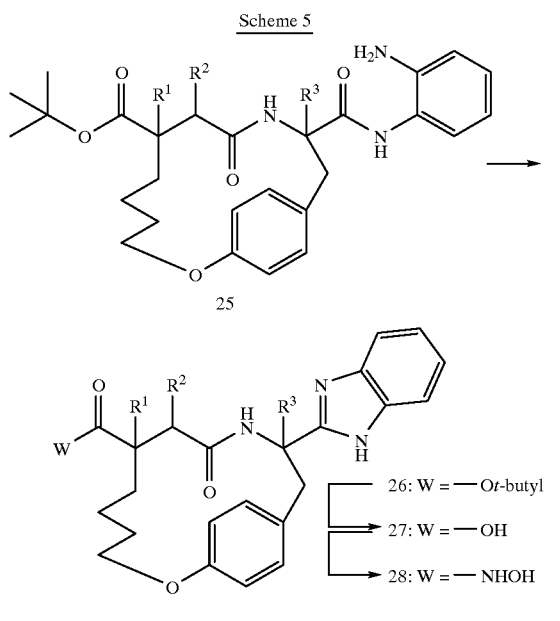

Macrocyclic olefins such as 30 are prepared by treating aryl iodide 29 with a suitable palladium catalyst, for instance tetrakis(triphenylphosphine)pallaium (0), and an amine base such as triethylamine and heating in a solvent such as acetonitrile. Olefin 30 is converted to the corresponding acid 31 and hydroxamate 32 according to the sequence outlined in Scheme 1.

Scheme 6

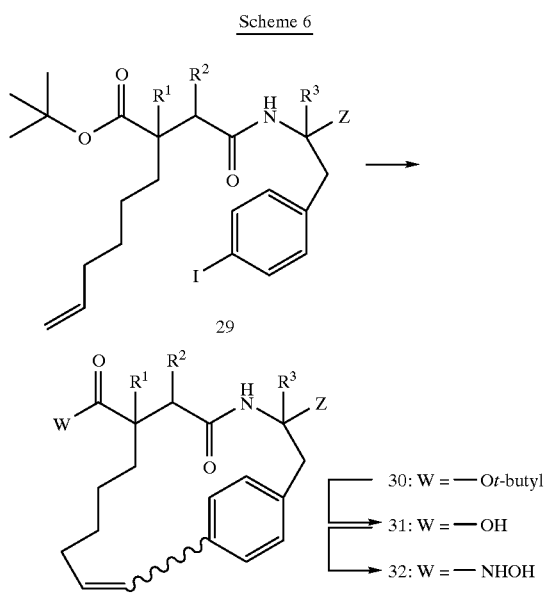

Tryptophan-derived macrocycles are prepared according to Scheme 7. Alcohol 33 is converted to a suitable leaving group, for example by reaction with p-toluenesulfonyl chloride in the presence of a tertiary base such as pyridine to give tosylate 34. This compound is subjected to phase-transfer alkylation conditions using, for example, potassium hydroxide and benzyltrimethyl ammonium chloride in a mixture of water and methylene chloride. The resulting macrocyclic ester 35 is converted to the corresponding acid 36 and hydroxamate 37 according to the sequence outlined in Scheme 1.

Scheme 7

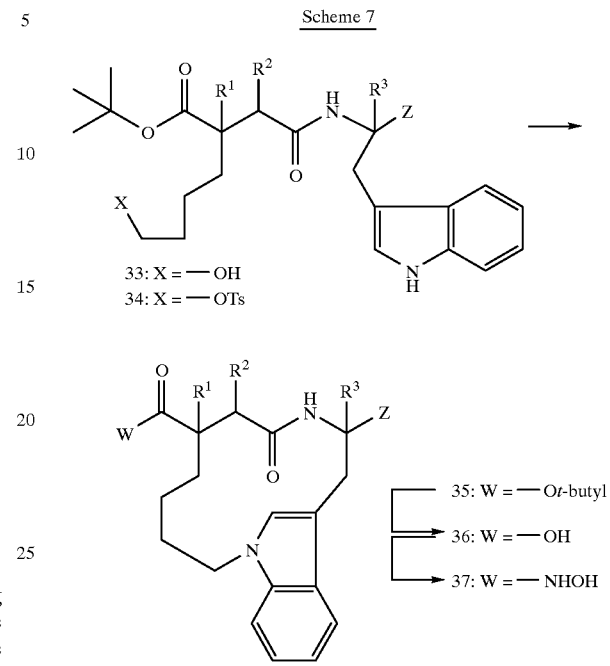

p-Aminophenylalanine-derived compounds of this invention are prepared as outlined in Scheme 8. Alcohol 38 is first converted to its mesylate using methanesulfonyl chloride and a tertiary amine base such as triethylamine. Hydrogenation of this material using 10% palladium on carbon and triethylamine in a solvent such as iso-propanol generates macrocyclic ester 39 directly. Conversion to acid 40 and hydroxamate 41 is accomplished by the reaction sequence shown in Scheme 1. Alcohol 38 can also be oxidized to acid 42 using, for example, chromic acid in sulfuric acid. Hydrogenation of the aromatic nitro group is achieved using hydrogen over a palladium catalyst. Lactam formation is completed by treatment with a coupling agent such as bis(2-oxo-3-oxazolidinyl)phosphinic chloride (BOP-Cl) in the presence of a tertiary amine base such as triethylamine giving 43 which is converted to the corresponding acid 44 and hydroxamate 45 as outlined in Scheme 1.

Scheme 8

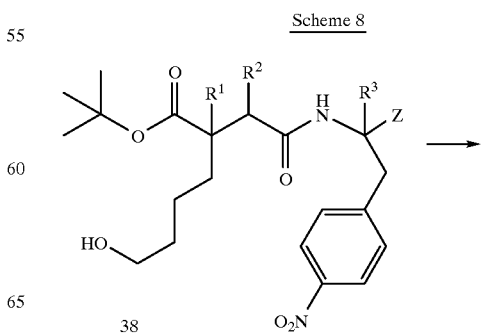

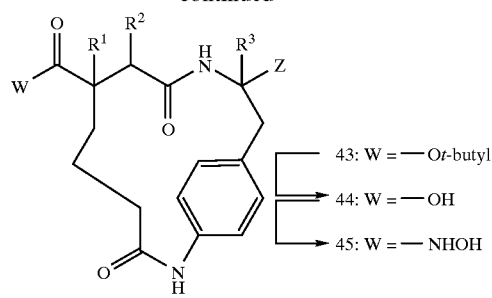
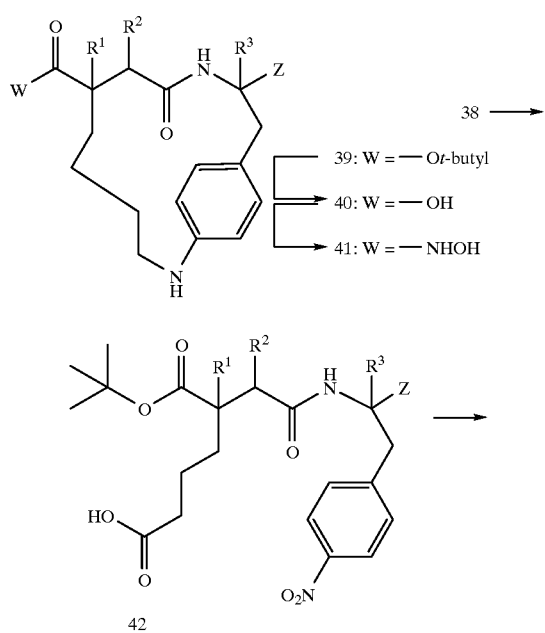

Carbamate and urea-derived macrocycles can be prepared according to Scheme 9. Alcohol 46 is treated with bromoacetyl bromide in the presence of sodium carbonate. The resulting ester 47 is subjected to hydrogenation conditions using, for example 10% palladium on carbon in the presence of a tertiary amine base such as triethylamine which gives macrocycle 48. The tert-butyl ester group of 48 can be converted to acid 49 and to hydroxamate 50 under the conditions illustrated in Scheme 1. Alcohol 46 is converted to the corresponding methanesulfonate 51 by reaction with methanesulfonyl chloride in the presence of triethylamine. Mesylate 51 is reacted with trimethylsilyl azide in the presence of tri-n-butylammonium fluoride to produce azide 52. This compound can be subjected to hydrogen over a palladium catalyst and the resulting diamine treated with a phosgene derivative such as carbonyldimidazole to generate urea 53. Conversion of this ester to the corresponding acid 54 and hydroxamate 55 is accomplished as described in Scheme 1.

Scheme 9

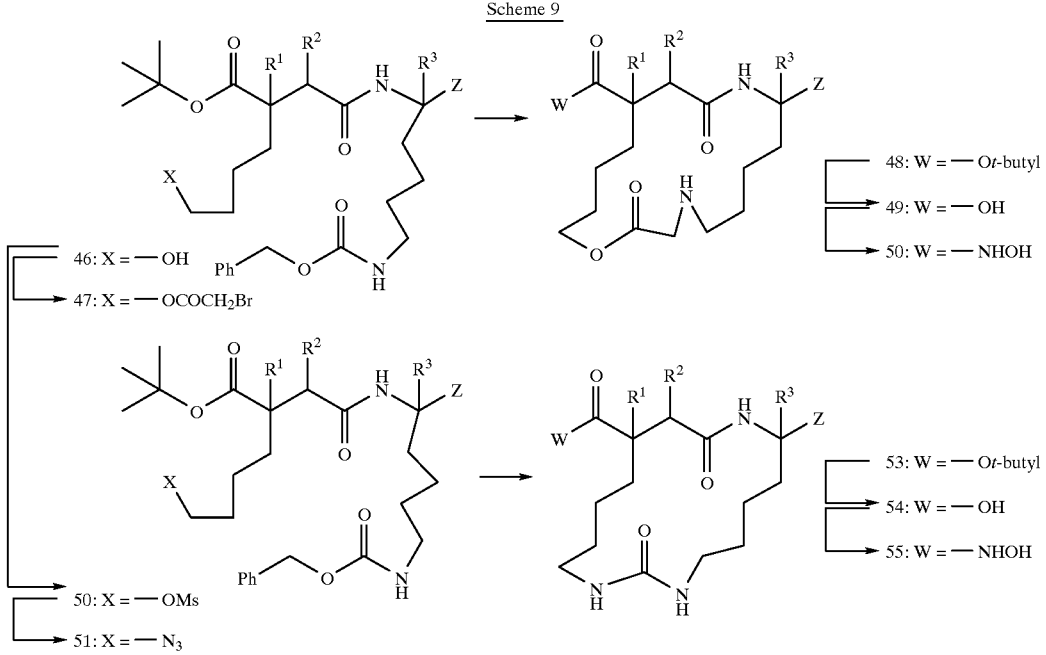

The preparation of macrocyclic lactones is shown in Scheme 10. Hydrogenolysis of the benzyl ester of 55 is achieved using hydrogen over a palladium catalyst. The resulting hydroxy acid is treated with 1,1'-(azodicarbonyl)

dipiperdine and tributylphosphine in a suitable solvent such as tetrahydrofuran to produce 56. This ester can be converted to the corresponding acid 57 and hydroxamate 58 as described in Scheme 1.

Scheme 10

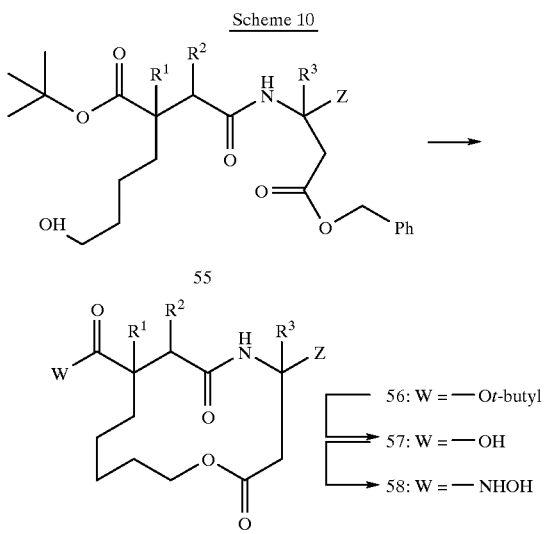

The foregoing may be better understood by reference to the following examples which are presented for illustration and are not intended to limit the scope of the invention as defined in the appended claims.

Preparation of Succinate Ester 1

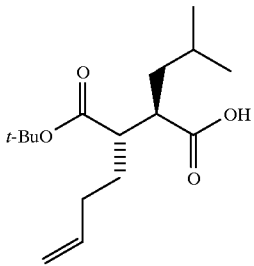

Step 1

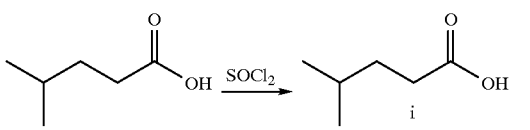

A mixture of 4-methylvaleric acid (50.7 g, 0.43 mmol) and thionyl chloride (40 mL, 65.2 g, 0.54 mole) was stirred at ambient temperature for 18 hours. The mixture was heated to distill the excess reagent through a 10 cm Vigreux column. The acid chloride was then distilled to give i (48.43 g, 84%), bp 135–138° C.

Step 2

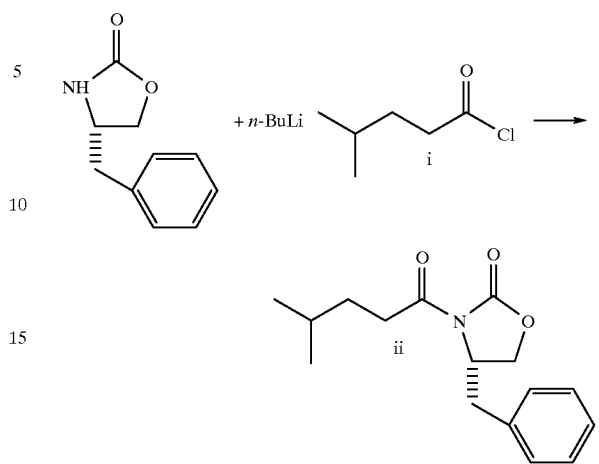

To a −78° C. solution of 4S-benzyl-2-oxazolidinone (62.2 g, 0.35 mole) in THF (600 mL) was added n-butyllithium (140 mL, 2.5 M in hexane) over 1 hour. After 30 minutes i (0.359 mole) was added over 10 minutes during which time the temperature rose to −60° C. After 1 hour the bath was removed and the reaction mixture was warmed to 0° C. The reaction was quenched with saturated ammonium chloride, the mixture was allowed to settle, and the supernatant was decanted and concentrated. The combined residues were partitioned between water and ethyl acetate. The organic layer was washed with water, 1M sodium bicarbonate, water and brine, dried over sodium sulfate, filtered and concentrated. The residue was distilled discarding a small forerun to give ii (92.9 g, 96%), bp 154–156° C./0.15 mm.

Step 3

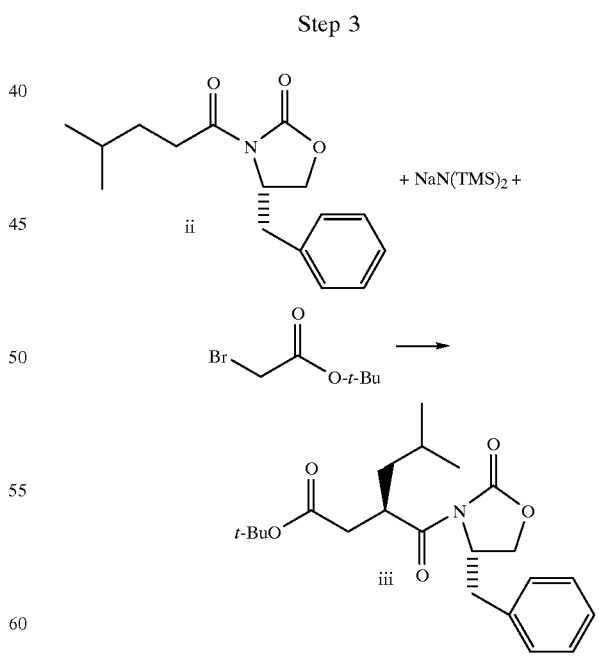

To a mechanically-stirred −78° C. solution of ii (92.9 g, 0.337 mole) in THF (1L) was added sodium bis(trimethylsilyl)amide (375 mL, 1M in THF) over 40 minutes. The reaction mixture was stirred for 30 minutes and t-butyl bromoacetate (55 mL, 72.6 g, 0.372 mole) was added over 30 minutes. The reaction mixture was stirred for 30 minutes and then the cold bath was removed and the mixture was warmed to 0° C. The reaction was quenched with saturated ammonium chloride. After mixing well, the mixture was allowed to settle and the supernatant was decanted, concentrated, and recombined with the residue. This mixture was partitioned between water and ethyl acetate. The organic layer was washed with water, 1 M sodium bicarbonate, water and brine, dried over sodium sulfate and concentrated by distillation to about 250 mL. After dilution with 750 mL hexane and cooling in an ice bath the resulting crystals were collected and washed with hexane to provide iii (104.6 g) mp 101–102° C. The mother liquors were concentrated and the residue was purified by chromatography on silica gel (5–10% ethyl acetate-hexane) and the product fraction crystallized to yield 7.6 g more for a total of 112.2 g (85%).

Step 4

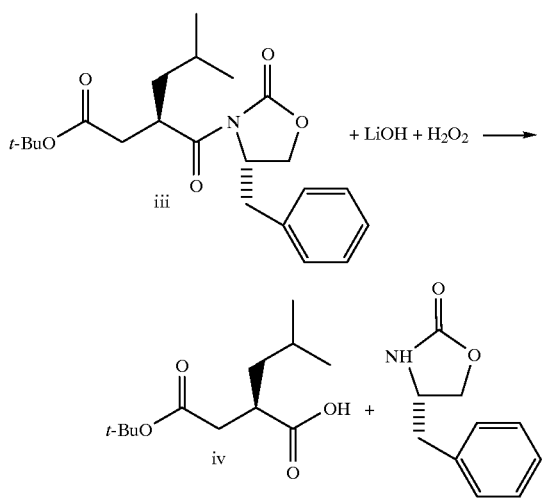

To a 0° C. solution of iii (112.2 g, 0.288 mole) in THF (1.2 L) was added water (100 mL) and 30% hydrogen peroxide (110 mL, 36.6 g, 1.08 mole). A solution of lithium hydroxide monohydrate (17.8 g, 0.424 mole) in water (400 mL) was added in portions over 25 minutes and the resulting solution was stirred for 1 hour. The mixture was concentrated under a slow nitrogen stream to about 800 mL. After seeding with the chiral oxazolidinone the mixture was chilled and filtered removing a portion of the auxiliary which was washed well with water. The filtrate was extracted with dichloromethane (3×) to remove the balance of the chiral oxazolidinone. The combined organic extracts were washed with aqueous 0.5 N sodium hydroxide. The base layers were acidified with 1M sulfuric acid to pH 3 and extracted with ethyl acetate. After washing with water and brine, drying over sodium sulfate, and evaporation of solvents the residue amounted to 64.9 g (98%) of R-2-(i-butyl)-succinic acid-4-t-butyl ester.

Step 5

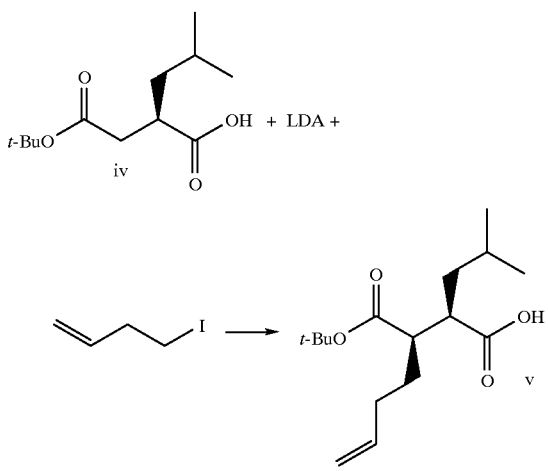

To a −78° C. solution of lithium diisopropylamide, prepared by the addition of n-butyllithium (11.4 ml, 28.4 mmol, 2.5M in hexanes) to a solution of diisopropylamine (3.7 ml, 28.4 mmol) in 60 ml THF at −78° C., was added a solution of iv (2.7 g, 11.8 mmol) in THF (20 mL) at −78° C. by cannula in a stream. The resulting clear, yellow solution was stirred at −78° C. for 1hour and then butenyl iodide (2.58 g, 14.2 mmol) was added by syringe. This mixture was allowed to warm to ambient temperature and stir overnight. The reaction mixture was poured into 1:1 ether-water and the separated aqueous layer was extracted with ether (2×). The combined organic layers were washed with aq 1M NaHSO$_4$ and brine, dried with MgSO$_4$, filtered and concentrated. Flash chromatography (2%–5% isopropanol-hexane) gave epimeric succinates v (2.30 g, >9:1 syn/anti) as a clear liquid.

Step 6

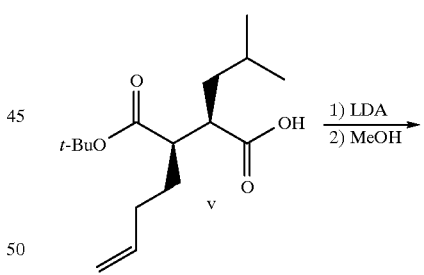

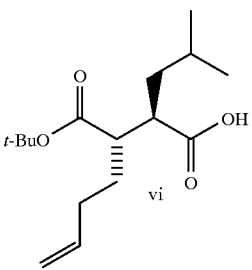

To a −78° C. solution of lithium diisopropylamide, prepared by the addition of n-butyllithium (7.8 ml, 19.5 mmol, 2.5M in hexanes) to a solution of diisopropylamine (2.6 ml, 19.5 mmol) in 30 ml THF at −78° C., was added a solution of epimeric isobutyl succinate v (2.3 g, 8.1 mmol) in THF (10 mL) at −78° C. by cannula in a stream. The resulting clear, yellow solution was stirred at −78° C. for 1 hour, warmed to 0° C. and recooled to −78° C. Methanol (1 ml) was added and the solution was warmed to 0° C. The reaction mixture was poured into 1:1 ether-water and the separated aqueous layer was extracted with ether (2×). The combined organic layers were washed with aq 1M NaHSO₄ and brine, dried with MgSO₄, filtered and concentrated to give an epimeric mixture (2:1 aniti/syn) of succinates vi which could be separated by flash chromatography (10–50% ethyl acetate-hexanes).

Preparation of Succinate Ester 2

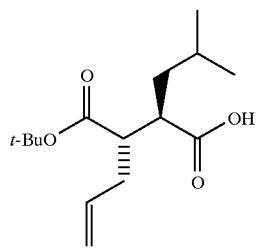

2

The desired compound was prepared according to the method used to prepare succinate ester 1, except substituting allyl bromide for 4-bromo-1-butene.

Preparation of Succinate Ester 3

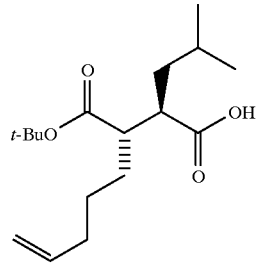

3

The desired compound was prepared according to the method used to prepare succinate ester 1, except substituting 5-bromo-1-pentene for 4-bromo-1-butene.

Preparation of Succinate Ester 4

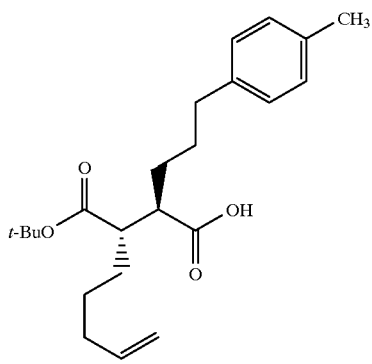

4

Step 1

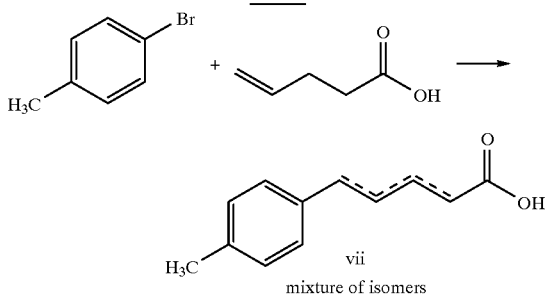

vii
mixture of isomers

A mixture under nitrogen of 4-bromotoluene (36.9 mL, 51.3 g, 0.3 mole), 4-pentenoic acid (30.6 mL, 30.0 g, 0.3 mole), acetonitrile (500 mL), triethylamine (126 mL, 91.5 g, 0.90 mole), palladium acetate (1.35 g, 6 mmole) and tri-(o-tolyl)phosphine (4.65 g, 15 mmole) was heated slowly to a gentle reflux. (A mild exotherm was observed as reflux begins.) After 18 hours at reflux, the mixture was cooled in an ice bath and the solid was removed by filtration and rinsed well with ethyl acetate. The filtrate was concentrated to a small volume and the residue was partitioned between aqueous 1 M sodium carbonate and ether. The aqueous phase was extracted with ether. The combined ether layers were extracted with aqueous 1 M sodium carbonate. The basic solution was treated with charcoal and filtered. The filtrate was acidified with 3 M hydrochloric acid. After cooling in an ice bath, the soft solid was filtered, washed with ice water, and dried over sodium hydroxide to give vii (45 g) as a mixture of isomers which was used without further purification.

Step 2

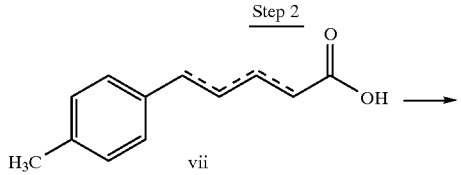

vii

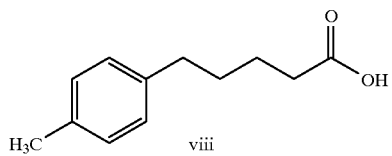

The mixture of isomers vii was hydrogenated in 600 mL THF over 9 g of 10% palladium on carbon at 4 atmospheres of hydrogen for 18 hours. After filtration and concentration of the solution, the residue was crystallized from hexane to yield 5-(4-tolyl)pentanoic acid (viii, 33 g, mp 77–78° C.).

Step 3

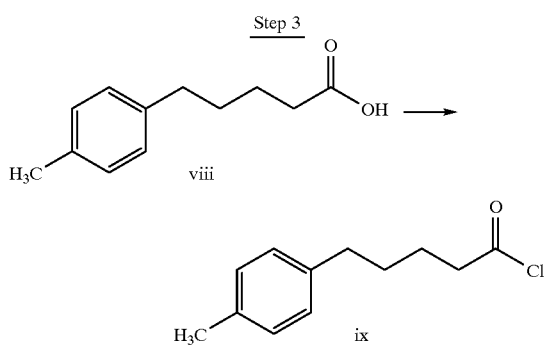

A mixture of 30b (11.02 g, 57 mmole) and 12 mL thionyl chloride was stirred at 24° C. for 18 hours and then heated to distill most of the excess thionyl chloride. Short path distillation gave 11.74 g (97%) of 5-(4-tolyl)pentanoyl chloride (30c, bp ~110° C. at 0.35 mm).

Step 4

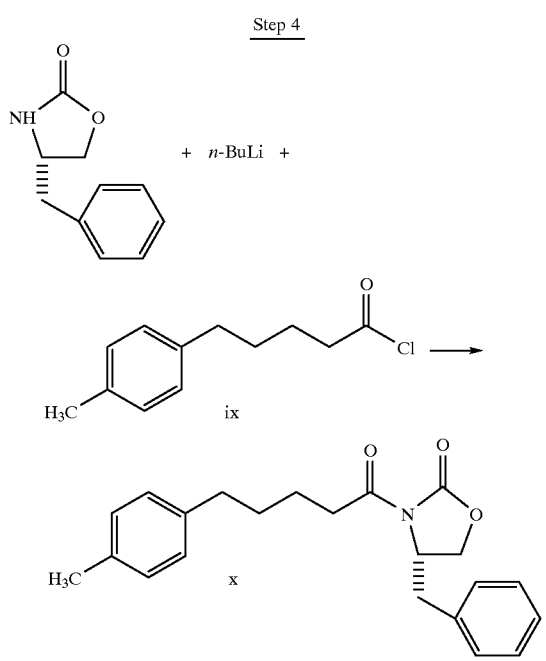

To a −78° C. solution of 4S-benzyl-2-oxazolidinone (10.36 g, 58 mmole) in THF (150 mL) was added n-butyllithium (23.5 mL 2.5 M) over 25 minutes. After 30 minutes, 30c (55.7 mmole) was added quickly, during which time the reaction temperature rose to −45° C. The reaction mixture was warmed to 0° C. and the reaction was quenched with saturated aqueous ammonium chloride. The mixture was allowed to settle and the supernatant was decanted and concentrated. The residue was partitioned between water and ethyl acetate. The organic layer was washed with water, aqueous 1M sodium bicarbonate, water and brine. After drying over sodium sulfate the solution was concentrated and the residue was chromatographed (10–20% ethyl acetate-hexane) to give 30d (17.83 g, 89%).

Step 5

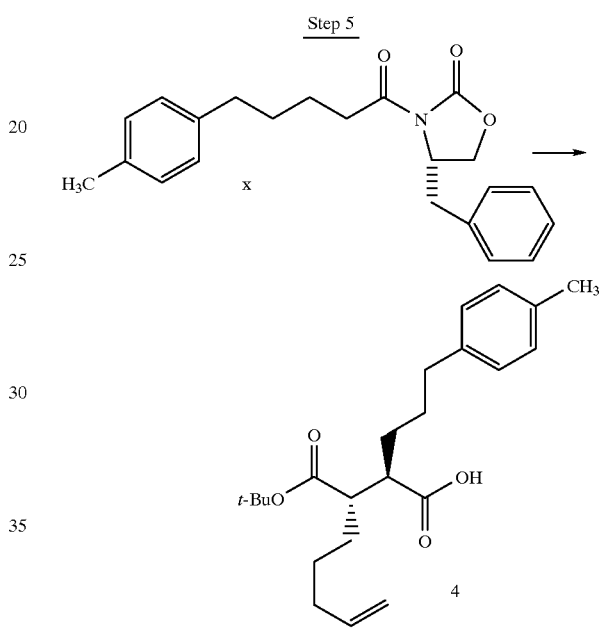

The desired compound was prepared using Steps 4, 5 and 6 of the preparation of succinate ester 1, except substituting x for iii and substituting 5-bromo-1-pentene for 4-bromo-1-butene.

Preparation of Succinate Ester 5

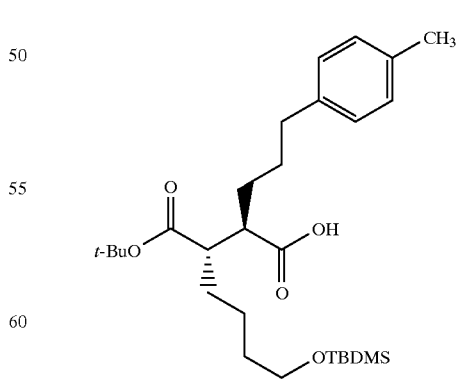

The desired compound was prepared using step 5 of the procedure for the preparation of succinate ester 4, except substituting TBDMSO(CH$_2$)$_4$I (10.8 g, 34.5 mmol), prepared as described by Heiquist et al., *Tetrahedron Lett.*, 1985, 26, 5393, for 5-bromo-1-pentene.

Preparation of Succinate Ester 6

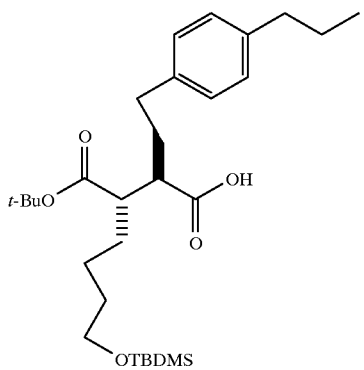

Step 1

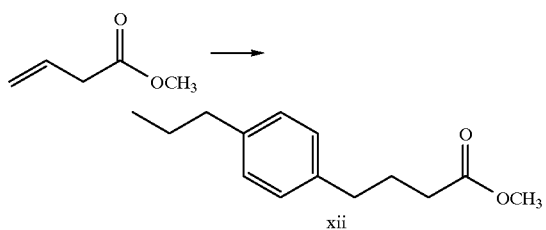

To a 0° C. solution in anhydrous THF (100 mL) of methyl 3-butenoate (97%, 10.0 g, 96.9 mmol) was added 9-BBN (0.5 M in THF, 194 mL, 97 mmol) dropwise via dropping funnel. After the addition was completed, the reaction mixture was stirred at ambient temperature for 5 hours. To the resulting solution was added anhydrous THF (300 mL), tetrakis(triphenylphosphine)palladium(0) (3.03 g, 2.62 mmol), 1-bromo-4-propylbenzene (98%, 13.8 mL, 87 mmol), and powdered sodium methoxide (95%, 7.72 g, 136 mmol). The reaction mixture was stirred at reflux for 16 hours. The reaction mixture was cooled to ambient temperature and ported into saturated aqueous ammonium chloride. The mixture was extracted twice with ether. The combined organic extracts were washed with brine, dried with $MgSO_4$ and concentrated to afford crude product as a light brown oil. Flash chromatography ($CH_2Cl_2$-hexane, 1:4) afforded xii (6.4 g).

Step 2

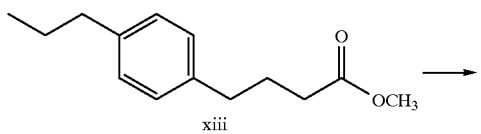

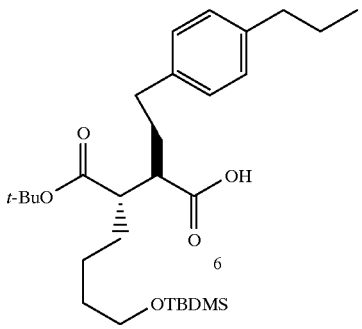

The desired compound was prepared by hydroysis of ester xiii, followed by conversion of the carboxylic acid to succinate ester 6 according to steps 3, 4 and 5 of the preparation of succinate ester 4, substituting $TBDMSO(CH_2)_4I$, for 5-bromo-1-pentene.

Preparation of Succinate Ester 7

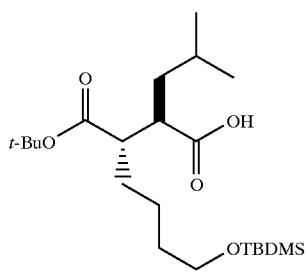

The desired compound was prepared according to the procedure used to prepare succinate ester 1, except substituting $TBDMSO(CH_2)_4I$, for 4-bromo-1-butene.

Preparation of Succinate Ester 8

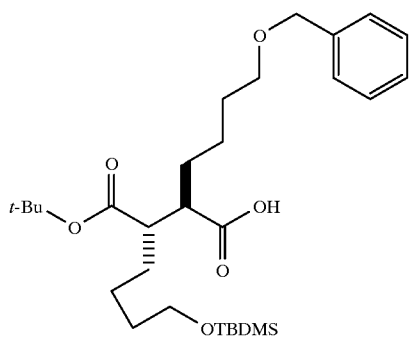

The desired compound was prepared in the same manner as succinate ester 5, except replacing acid viii with 6-benzyloxy hexanoic acid.

Preparation of Succinate Ester 9

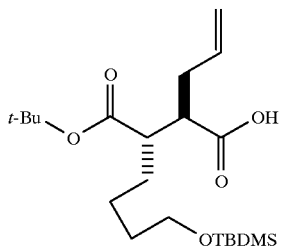

The desired compound was prepared in the same manner as succinate ester 5, except replacing acid viii with 4-pentenoic acid.

EXAMPLE 1

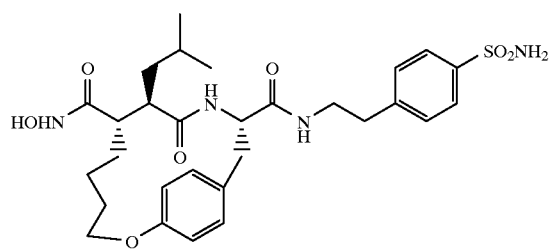

EXAMPLE 1A

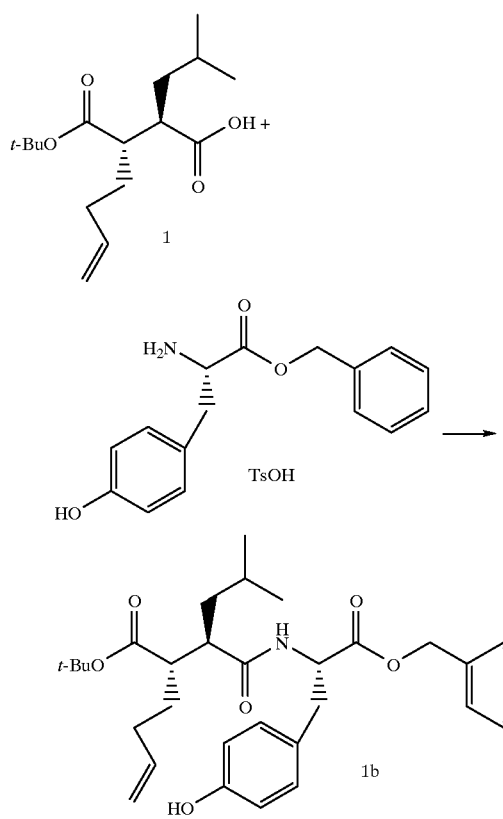

EXAMPLE 1B

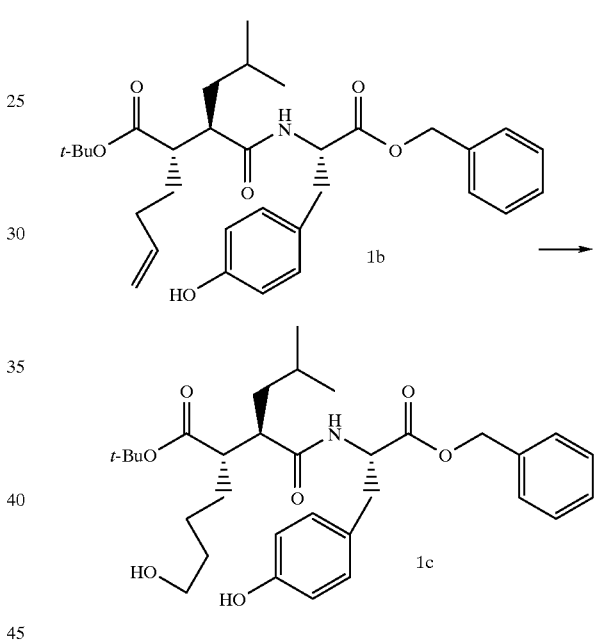

To a solution of succinate ester 1, benzyltyrosine tosylate salt (8.1 g, 18.4 mmol, Aldrich Chemical Co.), HOBT (2.5 g, 18.4 mmol) and NMM (4 mL, 36.8 mmol) in 80 mL DMF at 0° C. was added EDC (3.5 g, 18.4 mmol) in a single portion. The resulting solution was allowed to slowly warm to ambient temperature and was stirred for 3 days at which time it was poured into a sepratory funnel containing water and ethyl acetate. The separated aqueous layer was extracted with ethyl acetate (3×) and the combined organic layers were washed with aqueous 1M NaHSO$_4$, aqueous 1M NaHCO$_3$ and brine, dried over MgSO$_4$, filtered and concentrated in vacuo. The residue was flash chromatographed (CH$_2$Cl$_2$ to 2% methanol-CH$_2$Cl$_2$) to afford 8.26 g of intermediate 1b as a white foam.

To a solution of 1b (8.25 g, 15.4 mmol) dissolved in 77 mL THF at 0° C. was added BH$_3$ solution (1 M in THF, 51.3 mL, 51.3 mmol) dropwise by syringe over 10 minutes. The resulting solution was stirred at 0° C. for 1.5 hours. Ethanol (15.4 mL) was added over 5 minutes followed by pH 7 buffer (30 mL) and 30% H$_2$O$_2$ solution (30 mL). After 10 minutes, the cooling bath was removed and the cloudy mixture was stirred at ambient temperature for 2.5 hours at which time it was concentrated to half the original volume and added to a mixture of brine and and ethyl acetate. The separated aqueous layer was extracted with ethyl acetate (3×) and the combined organic layers were washed with brine, dried with MgSO$_4$, filtered and concentrated in vacuo. Flash chromatography (2% methanol-CH$_2$Cl$_2$ then 5% methanol-CH$_2$Cl$_2$) gave 7.62 g of intermediate Ic as a white foam.

EXAMPLE 1C

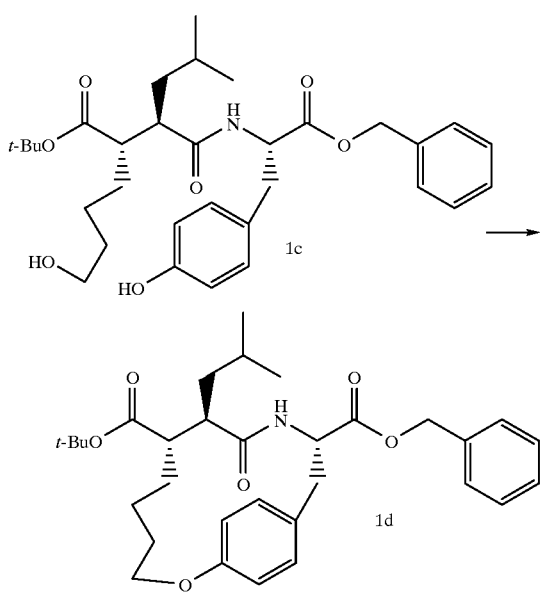

To a solution of 1c (4.54 g, 8.19 mmol) and Bu₃P (4.1 mL, 16.4 mmol) in 800 mL benzene at ambient temperature was added ADDP (4.13 g, 16.4 mmol) in a single portion. The solution was stirred at ambient temperature for 2 hours and then concentrated in vacuo. The residue was suspended in a minimal amount of CH₂Cl₂ and flash chromatographed (30% ethyl acetate-hexane) to give cyclic intermediate 1d (3.1 g) as a white solid.

EXAMPLE 1D

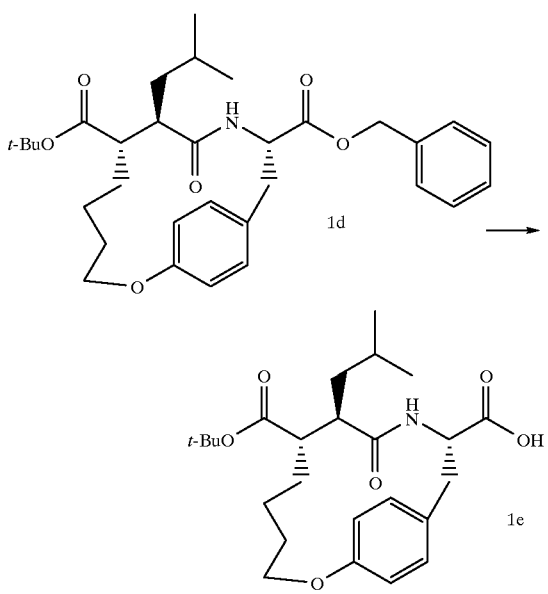

A mixture of 1d (3.1 g, 5.77 mmol) and 10% Pd/C catalyst (620 mg) in 30 mL methanol was stirred under a positive hydrogen pressure for 3 hours. The reaction mixture was then filtered through Celite with methanol washings. The filtrate was concentrated in vacuo to give cyclic intermediate 1e (2.54 g) as a white solid which was used without further purification.

EXAMPLE 1E

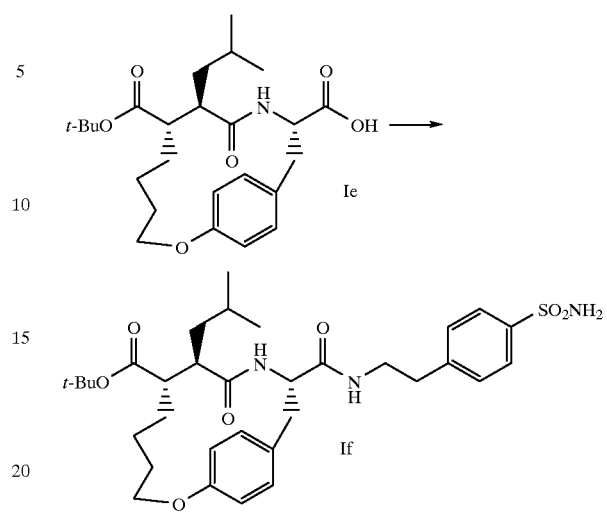

To a solution of 1e (510 mg, 1.14 mmol) dissolved in 6 mL DMF at 0° C. was added NMM (150 µL, 1.37 mmol), HOBT (185 mg, 1.37 mmol), EDC (263 mg, 1.37 mmol) and 4-(2-aminoethyl)benzenesulphonamide (274 mg, 1.37 mmol, Aldrich Chemical Co.). The resulting clear solution was stirred overnight at ambient temperature and then poured into a mixture of water and ethyl acetate. The separated aqueous layer was extracted twice with ethyl acetate and the combined organic layers were washed with brine, dried with MgSO₄, filtered and concentrated in vacuo. Flash chromatography (3% methanol-CH₂Cl₂) afforded 1f (758 mg) as a white solid.

EXAMPLE 1F

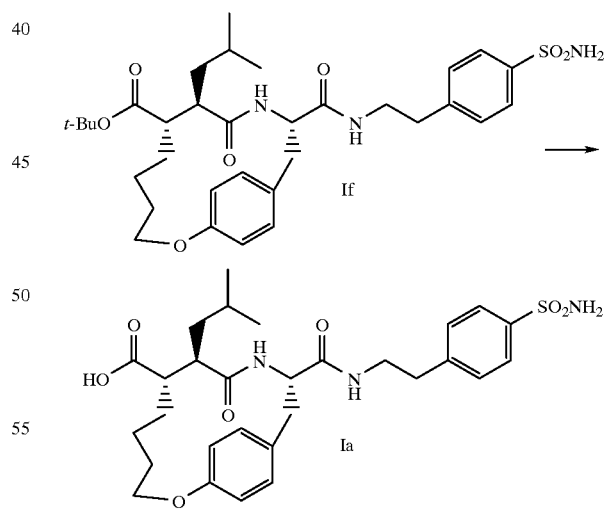

A mixture of 1f (717 mg, 1.14 mmol), trifluoroacetic acid (5 mL) and CH₂Cl₂ (1 mL) was stirred at ambient temperature for 1 hour and then concentrated under a stream of nitrogen. The residue was dissolved in 1:1 mix of CH₂Cl₂-methanol and concentrated in vacuo. This was repeated until a white solid formed to give 630 mg 1a which was used without purification.

EXAMPLE 1G

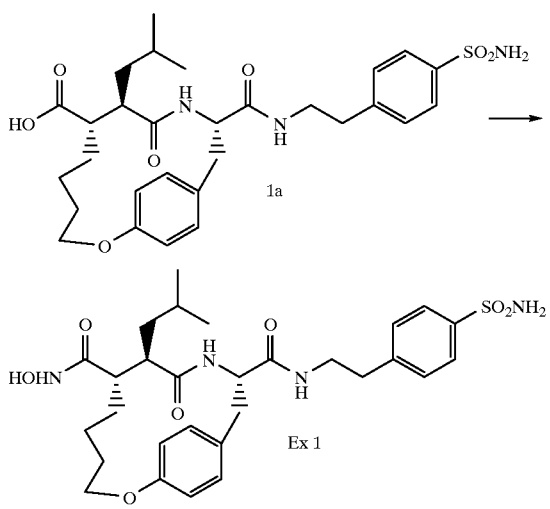

To a 0° C. solution in DMF (8 mL) of 1a (630 mg, 1.1 mmol) was added NMM (242 μL, 2.2 mmol). HOBT (178 mg, 1.32 mmol) and EDC (253 mg, 1.32 mmol). After 15 minutes at 0° C., O-(tert-butyldimethylsilyl)hydroxyl amine (194 mg, 1.32 mmol) was added in a single portion and the mixture was allowed to warm to ambient temperature and stir overnight. The solution was then poured into a mixture of brine and $CH_2Cl_2$. The aqueous layer was extracted twice with $CH_2Cl_2$ and the combined organic layers were washed with brine, dried with $Na_2SO_4$, filtered and concentrated in vacuo. The crude solid was flash chromatographed (5% methanol-$CH_2Cl_2$) to give 183 mg of the desired compound as a white solid. mp>270° C. $^1$H NMR (DMSO) δ -0.6-(-0.4) (m, 1H), 0.6-1.0 (m, 5H), 0.71 (d, 3H, J=6.3 Hz), 0.80 (d, 3H, J=6.3 Hz), 1.1-1.4 (m, 2H), 1.5-1.7 (m, 3H), 2.1 (dt, 1H, J=10.8, 2.7 Hz), 2.5-2.6 (m, 1H), 2.75-2.85 (m, 2H), 3.02 (dd, 1H, J=12.9,4.8 Hz), 3.3-3.4 (m, 2H), 3.9-4.1 (m, 2H), 4.5-4.7 (m, 1H), 6.90 (d, 2H, J=8.7 Hz), 7.21 (t, 2H, J=8.7 Hz), 7.29 (br s, 2H), 7.40 (d, 2H, J=8.1 Hz), 7.75 (d, 2H, J=8.1 Hz), 7.80 (d, 1H, J=9.6 Hz), 7.89 (t, 1H, J=5.7 Hz), 8.66 (s, 1H), 10.3 (s, 1H). $^{13}$C NMR (DMSO) δ 21.9, 24.5, 25.0, 25.3, 28.4, 28.7, 35.1, 37.0, 39.8, 41.1, 46.3, 46.9, 53.8, 73.2, 121.3, 121.5, 125.9. 129.0, 129.4, 132.4, 132.7, 142.4, 143.8, 157.4, 170.4, 171.5, 173.0. MS (CI) m/e 589 (M+1). Anal. Calcd for: $C_{29}H_{40}N_4O_7S \cdot 0.4H_2O$: C, 58.45; H, 6.90; N, 9.40. Found: C, 58.49; H, 6.94; N, 9.20. [α]+55° (c 0.5, DMF).

EXAMPLE 2

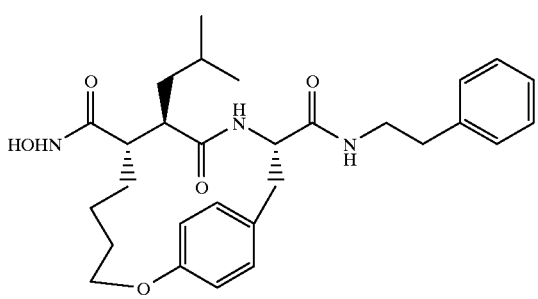

The desired compound was prepared according to the method of Examples 1E–G, except substituting phenethy- lamine for 4-(2-aminoethyl)benzenesulphonamide. mp>270° C. $^1$H NMR (DMSO) δ -0.6-(-0.4) (m, 1H), 0.6-1.0 (m, 4H), 0.70 (d, 3H, J=6.3 Hz), 0.80 (d, 3H, J=6.3 Hz), 1.1-1.4 (m, 2H), 1.5-1.7 (m, 3H), 2.0-2.1 (m, 1H), 2.5-2.6 (m, 1H), (m, 1H), 2.7-2.8 (m, 2H), 3.0-3.1 (m, 1H), 3.2-3.4 (m, 2H), 3.9-4.1 (m, 2H), 4.55-4.65 (m, 1H), 6.90 (d, 2H, J=8.4 Hz), 7.15-7.35 (m, 7H), 7.8-7.9 (m, 2H), 8.68 (s, 1H), 10.3 (s, 1H). $^{13}$C NMR (DMSO) δ 21.6, 24.2, 24.7, 24.9, 28.0, 28.4, 35.1. 36.7, 40.0, 40.8, 46.0, 46.6, 53.5, 72.9, 120.9, 121.1, 126.0, 128.2, 128.5, 128.7, 132.0, 132.4, 139.2, 157.0, 170.0, 171.1, 172.7. MS (CI) m/e 510(M+1). Anal. Calcd for: $C_{29}H_{39}N_3O_5$: C, 68.34; H, 7.71; N, 8.24. Found: C, 68.00; H, 7.78; N, 8.05. [α]+18° (c 0.5, DMF).

EXAMPLE 3

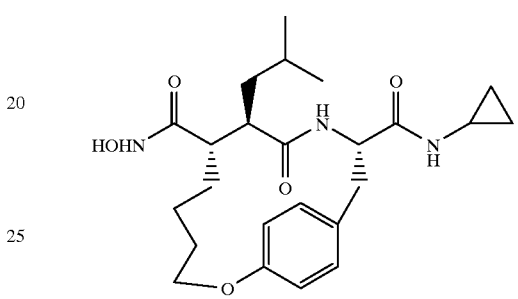

The desired compound was prepared according to the method of Examples 1E–G, except substituting cyclopropy- lamine for 4-(2-aminoethyl)benzenesulphonamide. mp>270° C. $^1$H NMR (DMSO) δ -0.6-(-0.4) (m, 1H), 0.3-0.4 (m, 2H), 0.6-0.7 (m, 2H), 0.71 (d, 3H, J=6 Hz), 0.8 (d, 3H, J=6 Hz), 0.7-1.0 (m, 5H), 1.1-1.3 (m, 2H), 1.5-1.7 (m, 3H), 2,04 (apparent t, 1H, J=12 Hz), 2.5-2.7 (m, 2H), 3.04 (dd, 1H, J=12.8,4.1 Hz), 3.9-4.1 (m, 2H), 4.5-4.6 (m, 1H), 6.90 (d, 2H, J=8.4 Hz), 7.15-7.25 (m, 2H), 7.7-7.85 (m, 2H), 8.69 (s, 1H), 10.3 (s, 1H), $^{13}$C NMR (DMSO) δ 5.60, 5.83, 21.6, 22.2, 24.2, 24.7, 24.9, 28.0, 28.4, 36.5, 40.8, 46.0, 46.5, 53.4, 72.9, 120.9, 121.2, 128.6, 132.0, 132.4, 157.0, 170.0, 172.2, 172.6. MS (CI) m/e 446 (M+1). Anal. Calcd for $C_{24}H_{35}N_3O_5 \cdot 0.3H_2O$: C, 63.92; H, 7.96; N, 9.32. Found: C, 63.86; H, 7.96; N, 9.39. [α]+17° (c 0.5, DMF).

EXAMPLE 4

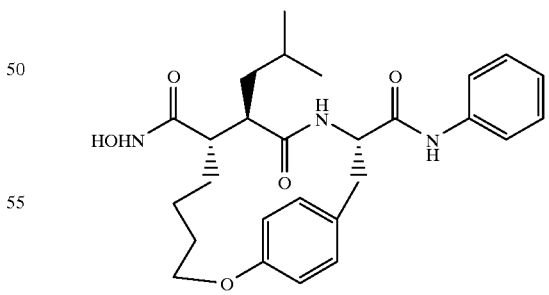

The desired compound was prepared according to the method of Examples 1E–G, except substituting aniline for 4-(2-aminoethyl)benzenesulphonamide. mp>270° C. $^1$H NMR (DMSO) δ -0.5-(-0.4) (m, 1H), 0.6-1.0 (m, 4H), 0.67 (d, 3H, J=6.3), 0.81 (d, 3H, J=6.3 Hz), 1.1-1.4 (m, 2H), 1.5-1.65 (m, 2H), 1.69 (dt, 1H, J=10.8, 2.4 Hz), 2.12 (dt, 1H, J=10.5, 2.7 Hz), 2.69 (br t, 1H, J=12.6 Hz), 3.9-4.0 (m, 1H), 4.0–4.1 (m, 1H), 4.75–4.90 (m, 1H), 6.9–7.0 (m, 2H), 7.07 (t, 1H, J=7.2 Hz), 7.25–7.40 (m, 4H), 7.60 (d, 2H, J=7.8 Hz), 7.98 (d, 1H, J=9.6 Hz), 8.70 (s, 1H), 10.0 (s, 1H), 10.3 (s, 1H). $^{13}C$ NMR (DMSO) δ 21.6, 24.2, 24.7, 25.0, 28.1, 28.4, 36.7, 40.8, 46.0, 46.6, 54.4, 73.0, 119.1, 121.0, 121.3, 123.3, 128.8, 132.1, 132.3, 138.8, 157.1, 170.0, 170.1, 172.9. MS (CI) m/e 482 (M+1). Anal. Calcd for $C_{27}H_{35}N_3O_5 \cdot H_2O$: C, 64.91; H, 7.46; N, 8.41. Found: C, 64.85; H, 7.16; N, 8.29. [α]+38° (c 0.4, MeOH).

EXAMPLE 5

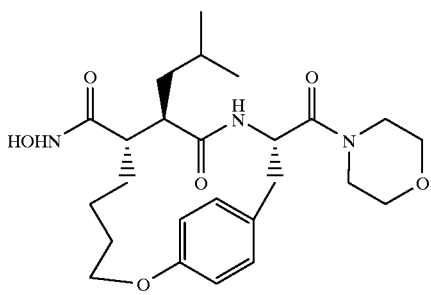

The desired compound was prepared according to the method of Examples 1E–G, except substituting morpholine for 4-(2-aminoethyl)benzenesulphonamide. mp>270° C. $^1H$ NMR (DMSO) δ –0.6–(–0.4) (m, 1H), 0.6–1.0 (m, 4H), 0.71 (d, 3H, J =6.3 Hz), 0.78 (d, 3H, J=6.3 Hz),1.14 (dt, 1H, J=10.8, 2.7 Hz), 1.2–1.4 (m, 1H), 1.45–1.55 (m, 2H), 1.68 (dt, 1H, J=11.1, 3.0 Hz), 2.10 (dt, 1H, J=11.4, 3.3 Hz), 2.79 (t, 1H, J=12.6 Hz), 2.9–3.0 (m, 1H), 3.4–3.8 (complex m, 8H), 3.9–4.1 (m, 2H), 5.0–5.1 (m, 1H), 6.89 (d, 2H, J=8.4 Hz), 7.27 (t, 2H, J=7.3 Hz),8.00 (d, 1H, J=9.6 Hz), 8.67 (s, 1H), 10.3 (s, 1H). $^{13}C$ NMR (DMSO) δ 21.6, 24.0, 24.8, 25.0, 28.2, 28.5, 40.3, 40.9, 45.7, 46.5, 48.9, 66.1, 72.8, 120.7, 120.8, 129.1, 131.9, 132.2, 157.1, 169.7, 170.0, 172.5. MS (CI) m/e 476 (M+1). Anal. Calcd for $C_{25}H_{37}N_3O_6 \cdot 0.5H_2O$: C, 61.96; H, 7.90; N, 8.67. Found: C, 61.86; N, 7.24. [α]+65° (c 0.4, MeOH).

EXAMPLE 6

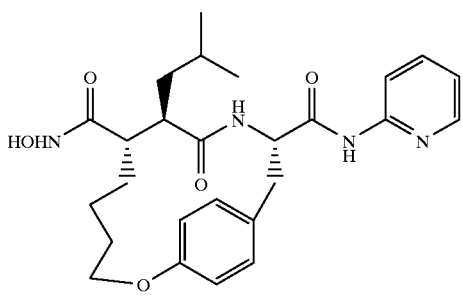

The desired compound was prepared according to the method of Examples 1E–G, except substituting 2-aminopyridine for 4-(2-aminoethyl)benzenesulphonamide. mp>270° C. $^1H$ NMR (DMSO) δ –0.6–(–0.4) (m, 1H), 0.6–1.0 (m, 4H), 0.68 (d, 3H, J=6.3 Hz), 0.83 (d, 3H, J=6.3 Hz), 1.1–1.4 (m, 2H), 1.5–1.8 (m, 3H), 2.13 (dt, 1H, J=10.8, 2.7 Hz), 2.66 (t, 1H, J=12.0 Hz), 3.28 (dd, 1H, J=12.3, 6.0 Hz), 3.9–4.0 (m, 1H), 4.0–4.1 (m, 1H), 4.8–5.0 (m, 1H), 6.9–7.0 (m, 2H), 7.1–7.2 (m, 1H), 7.25–7.40 (m, 2H), 7.83 (dt, 1H, J=8.1, 1.8 Hz), 7.99 (d, 1J=9.6 Hz), 8.06 (d, 1H, J=8.4 Hz), 8.35 (dd, 1H, J=5.4, 2.1 Hz), 10.3 (br s, 1H), 10.5 (s, 1H). $^{13}C$ NMR (DMSO) δ 21.6, 24.2, 24.8, 25.0, 28.1, 28.4, 36.3, 40.8, 46.1, 46.7, 54.6, 73.1, 113.6, 119.6, 121.1, 121.6, 128.8, 132.2, 132.4, 139.0, 147.4, 151.4, 157.3, 170.0, 171.1, 173.2. MS (CI) m/e 483 (M+1). Anal. Calcd for $C_{26}H_{34}N_4O_5 \cdot H_2O$: C, 62.38; H, 7.24; N, 11.19. Found: C, 62.04; H, 7.44; N, 9.70. [α]+34° (c 0.6, MeOH).

EXAMPLE 7

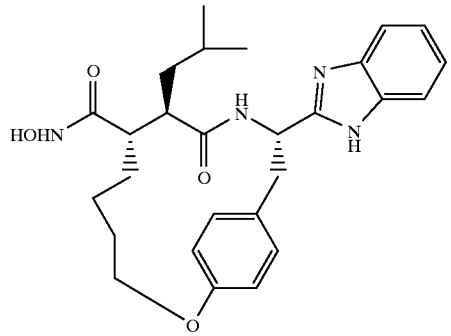

EXAMPLE 7A

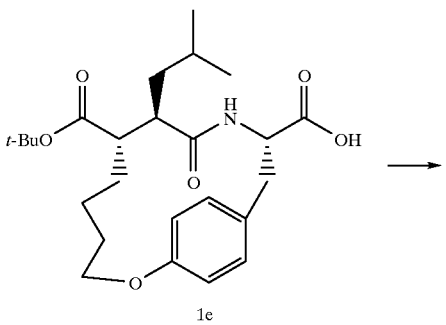

The desired compound was prepared using the procedure described for example 1E, except substituting 1,2-phenylenediamine for 4-(2-aminoethyl)benzenesulphonamide.

EXAMPLE 7B

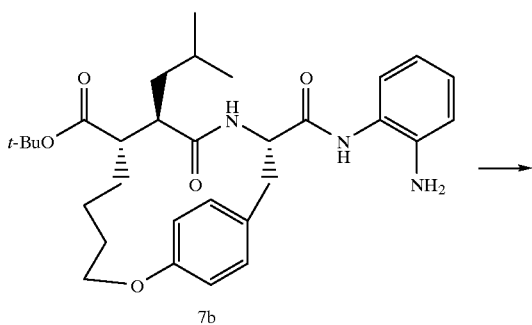

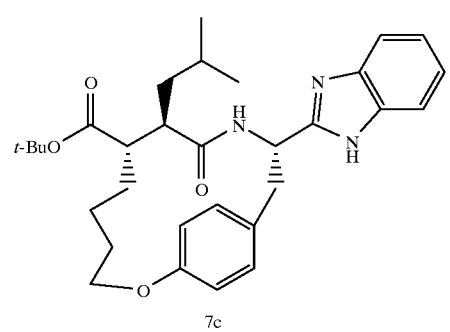

A solution of 7b and camphorsulfonic acid (60 mg) in 15 mL toluene and 5 mL THF was stirred at reflux for 3 hours. The resulting brown solution was cooled, concentrated and flash chromatographed (3% methanol-$CH_2Cl_2$) to afford 7c (1.0 g) as a light tan solid.

EXAMPLE 7C

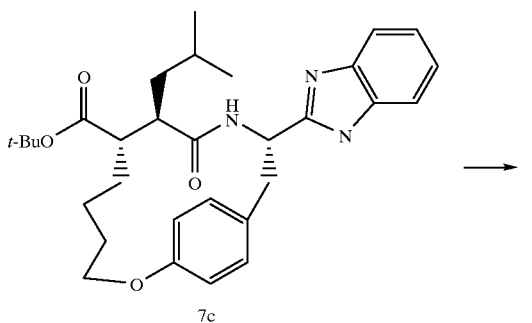

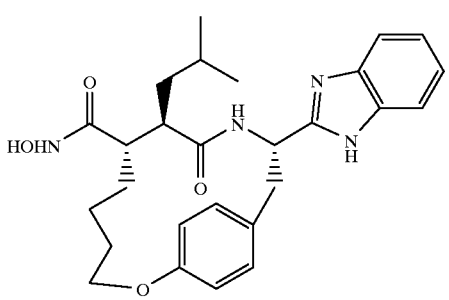

The desired compound was prepared from 7c according to the method of Examples 1F and G. mp>270° C. $^1$H NMR (DMSO) δ −0.5–(−0.3) (m, 1H), 0.6–1.0 (m, 4H), 0.59 (d, 3H, J=6.3 Hz), 0.64 (d, 3H, J=6.3 Hz), 1.1–1.4 (m, 2H), 1.6–1.8 (m, 3H), 2.0–2.1 (m, 1H), 3.07 (t, 1H, J=12.9 Hz), 4.0–4.2 (m, 2H), 5.4–5.5 (m, 1H), 6.96 (apparent d, 2H, J=6.3 Hz), 7.1–7.2 (m, 2H), 7.32 (br t, 2H, J=6.9 Hz), 7.4–7.5 (m, 2H), 8.18 (d, 1H, J=9.0 Hz), 8.69 (s, 1H), 10.3 (s, 1H), 12.2 (s, 1H). $^{13}$C NMR (DMSO) δ 21.6, 24.1, 24.7, 28.1, 28.5, 38.0, 40.9, 46.1, 46.6, 47.9, 72.9, 111.3, 118.5, 121.1, 121.2, 121.9, 128.8, 132.2, 132.5, 154.9, 157.2, 170.1, 172.6. MS (CI) m/e 479 (M+1). Anal. Calcd for $C_{27}H_{34}N_4O_4 \cdot 1.4H_2O$: C, 64.37; H, 7.36; N, 11.12. Found: C, 64.47; H, 7.41; N, 10.35. [α]−39° (c 0.5, DMF).

EXAMPLE 8

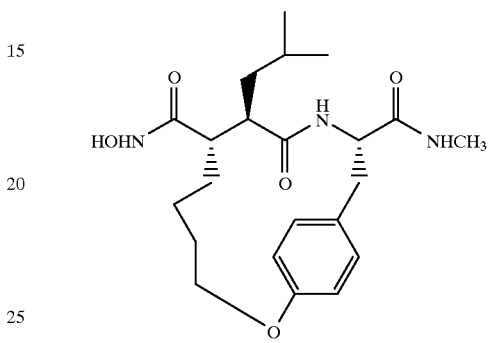

EXAMPLE 8A

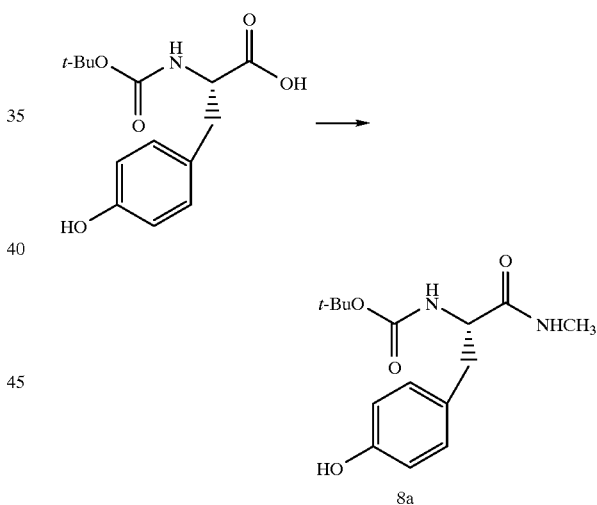

To a 0° C. solution in DMF (40 mL) of BOC-L-tyrosine (2.81 g, 10 mmol) and HOBT (3.70 g, 27 mmol) was added methylamine hydrochloride (675 mg, 10 mmol) and NMM (3.16 mL, 2.9 mmol) and the mixture was stirred for 30 minutes. EDC (2.76 g, 14 mmol) was added and stirring was continued for 2 hours in the ice bath and then at room temperature for 3 days. The reaction mixture was diluted with saturated aqueous ammonium chloride and was extracted twice with ethyl acetate. The organic extracts were combined, dried over sodium sulfate, filtered and the filtrate concentrated to a yellow oil. A minimum amount of ethyl acetate was added and the suspension heated until a solution resulted. Crystallization was allowed to occur at room temperature and 8a as a white solid was collected by filtration (1.97 g, 67% yield).

EXAMPLE 8B

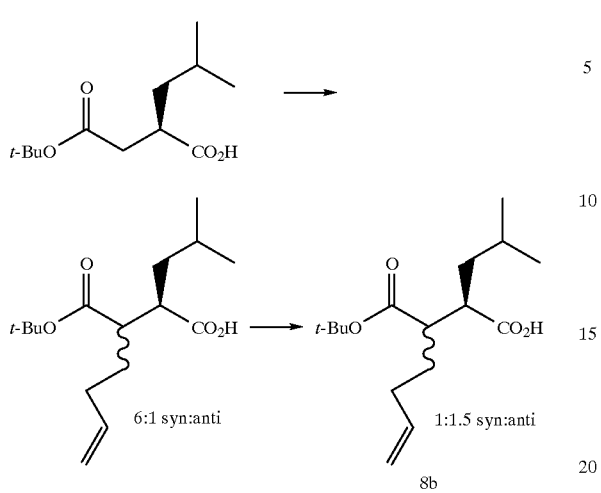

Step 1: To a −78° C. solution in THF (8 mL) of diisopropylamine (541 mg, 5.35 mmol) was added butyllithium (2 ml, 5 mmol, 2.5M in hexanes) dropwise and the solution was stirred for 15 minutes. A mixture of (R)-iso-butylsuccinic acid tert-butylester (0.5 g, 2.17 mmol) in DMPU (1 mL) and THF (3 mL) was added dropwise. The resulting yellow solution was stirred for one hour at −70° C. and a solution of 4-bromo-1-butene (354 mg, 2.62 mmol) in THF (3 mL) was added dropwise over 8 minutes. The reaction mixture was stirred for 1hour at −70° C. and a solution of LiI (35 mg, 2.62 mmol) in THF (1 mL) was added dropwise. The cold bath was removed and stirring was continued overnight at ambient temperature. The reaction mixture was poured into saturated aqueous ammonium chloride and ethyl acetate and the organic layer set aside. The aqueous layer was washed once with ethyl acetate and the organics combined, dried over MgSO4, filtered and the filtrate concentrated to a yellow oil which was purified by flash chromatography on silica gel (15% ethyl acetate-hexanes) to yield 244 mg of 8b as a yellow gum(40% yield). Isomer ratio approximately 6:1.

Step 2: To a −78° C. solution in THF (7 mL) of diisopropylamine (523 mg, 5.17 mmol) was added butyllithium (1.93 ml, 4.83 mmol, 2.5M in hexanes) dropwise and the solution was stirred for 15 minutes. A solution of 8b (611 mg, 2.15 mmol) in THF (8 mL) was added dropwise. The reaction mixture was warmed to −20° C. and stirred for 15 minutes before being cooled to −78° C. and quenched with a solution of methanol(356 mg, 11 mmol) in 2 ml THF. The reaction mixture was warmed to room temperature and mixed with saturated aqueous ammonium chloride and the pH was adjusted to 4 with added dilute HCl. The solution was extracted twice with ethyl acetate and the organic extracts were combined, dried over MgSO4, filtered and the filtrate concentrated to a to give 8b (594 mg) as a yellow gum having an isomer ratio determined by CMR to be 1:1.5 syn:anti.

EXAMPLE 8C

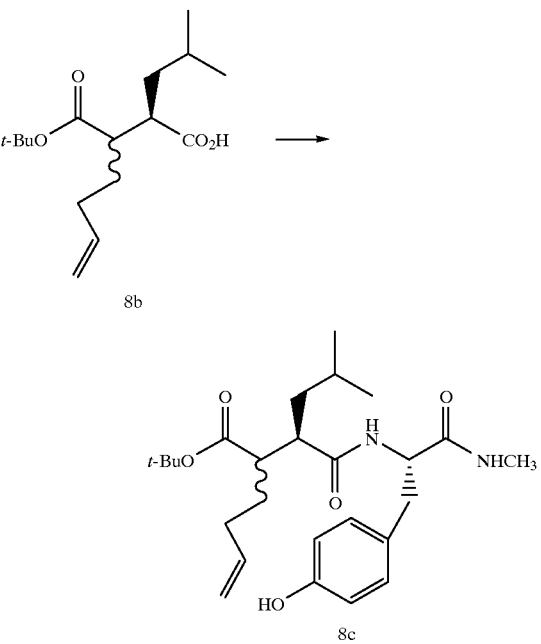

To a solution of BOC-L-tyrosine-N-methyl amide (8a, 627 mg, 2.13 mmol) in THF (2 ml) was added 4M HCl-dioxane (6 mL) dropwise. The resulting yellow solution was stirred for 4 hours at ambient temperature and then concentrated to dryness. The residue was azeotroped twice with toluene and once with ether leaving an off-white solid which was added to an ice-bath-cooled flask containing compound 8b (561 mg, 1.97 mmol), HOBT (716 mg, 5.3 mmol), NMM (562 mg, 5.6 mmol) and DMF (8 mL). The resulting orange solution was stirred for 30 and EDC (534 mg, 2.79 mmol) was added as a solid. Stirring in the ice bath was continued for 2 hours and then at room temperature overnight. The reaction mixture was diluted with saturated aqueous ammonium chloride and extracted 3 times with ethyl acetate. The organic extracts were combined, dried, filtered and the filtrate concentrated to a yellow oil which was purified by flash chromatography(4% methanol-methylene chloride) to give 8c (783 mg, 86% yield) as a white powder.

EXAMPLE 8D

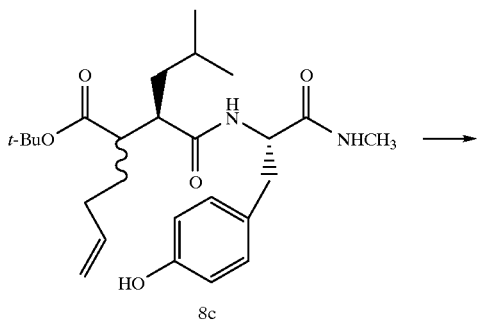

-continued

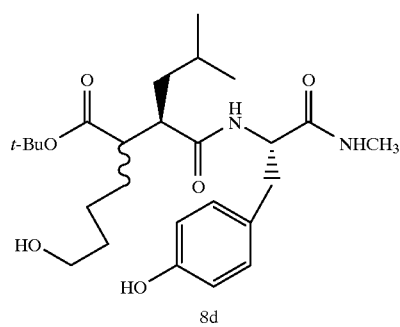

8d

The desired compound 8d was prepared from 8c by hydroboration/oxidation according to the method of Example 1C.

EXAMPLE 8E

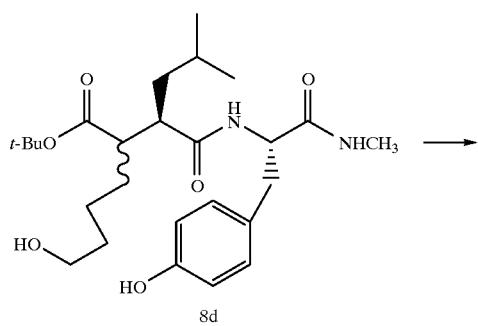

8d

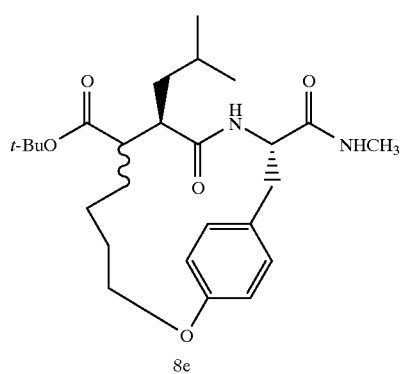

8e

To a −5° C. solution of triphenylphosphine (419 mg, 1.6 mmol) in methylene chloride (20 mL) was added dropwise a solution of diethylazodicarboxylate (249 mg, 1.43 mmol) in methylene chloride (20 mL) and the solution stirred for 30 minutes. A solution of 8d (465 mg, 0.97 mmol) in methylene chloride (120 mL) was added dropwise and the solution was stirred for 1 hour. The reaction mixture was poured into brine and the organic layer set aside. The aqueous phase was washed with ethyl acetate and the organic layers were combined, dried and concentrated to a yellow gum which was purified by flash chromatography (50% ethyl acetate-hexanes) to give the desired compound 8e (75 mg).

EXAMPLE 8F

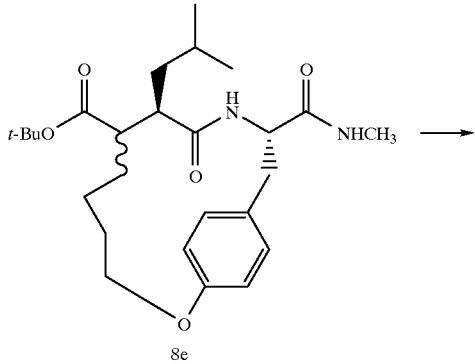

8e

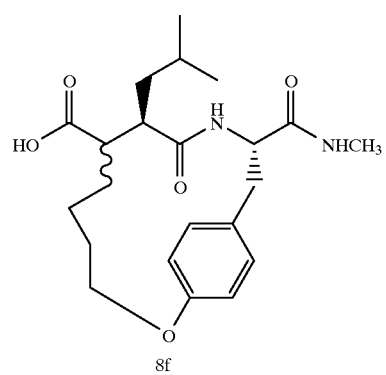

8f

The desired compound 8f was prepared by saponification of 8e using trifluoroacetic acid in dichloromethane according to the method of Example 1F.

EXAMPLE 8G

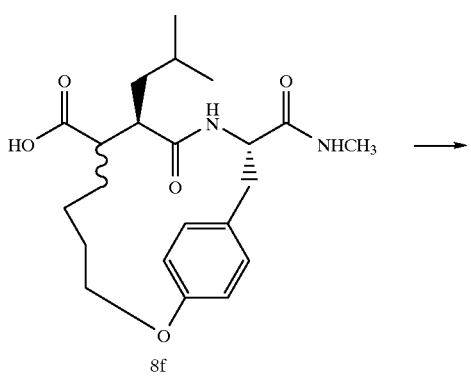

8f

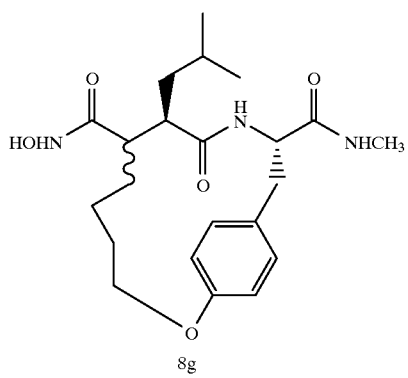

8g

To a 0° C. solution of 8g (50 mg, 0.125 mmol) in DMF (0.8 mL) was added NMM(19 mg, 0.19 mmol), a solution of HOBT (19 mg, 0.14 mmol) in DMF (0.2 mL) and EDC (27 mg, 0.14 mmol). After stirring for 15 minutes, a solution of O-tert-butyldimethylsilylhydroxylamine (21 mg, 0.14 mmol) in DMF (0.2 mL) was added and stirring was continued for 30 minutes in the ice bath and then at ambient temperature for 3 days. The reaction mixture was diluted with saturated aqueous ammonium chloride and was extracted twice with ethyl acetate. The combined organic extracts were dried and concentrated to a clear gum. The gum was mixed with diethyl ether and the resulting suspension filtered to give 32 mg of a white solid (61% yield). A portion (9.8 mg) of this material was dissolved in a mixture of 1.5 ml acetonitrile, 0.5 ml methanol and 2.0 ml water and loaded onto a C-18 reverse phase HPLC column and eluted with a gradient from 10% acetonitrile/90% water to 70% acetonitrile/30% water. The faster eluting peak was collected and concentrated to give the anti compound as a white powder (3.1 mg) and the slower eluting peak was collected and concentrated to give the syn compound as a white powder (3.4 mg).

Anti: $^1$H NMR (300 MHz, DMSO-d6) δ 10.41 (s, 1H), 8.69 (s, 1H), 7.79–7.87 (c, 1H), 7.69–7.76 (c, 1H), 7.51–7.67 (c, 1H), 7.16–7.28 (c, 1H), 6.87–6.96 (c, 2H), 4.53–4.64 (c, 1H), 3.88–4.13 (c, 2H), 3.01–3.11 (c, 1H), 2.54–2.69 (c, 4H), 2.00–2.13 (c, 1H), 1.51–1.73 (c, 3H), 1.12–1.36 (c, 2H), 0.84–0.95 (c, 1H), 0.80 (d, 3H, J=6Hz), 0.71 (d, 3H, J=6 Hz), 0.50–0.67 (c, 1H). $^{13}$C NMR (300 MHz, DMSO-d6) δ 172.68, 172.65, 171.56, 157.03, 132.05, 128.64, 121.26, 120.99, 97.75, 72.97, 53.49, 46.61, 45.97, 40.83, 36.75, 28.38, 28.04, 25.45, 24.93, 24.75, 24.22, 21.60. IR, (KBr) 3300, 2950, 2940, 1640, 1530, 1510, 1210, 1190 cm$^{-1}$. MS (DCI/NH$_3$) m/e 420(m+H)$^+$.

Syn:$^1$H NMR (300 MHz, DMSO-d6) δ 9.90 (bs 1H), 7.94–8.01 (c, 1H), 7.40 (d, 1H, J=6 Hz), 7.05 (dd, 1H, J=1.5, 4.5 Hz), 6.73–6.79 (c, 2H), 6.66–6.71 (c, 1H), 5.66–5.74 (c, 1H), 3.96–4.03 (c, 1H), 3.81–3.90 (c, 1H), 2.91 (dd, 1H, J=3, 9 Hz), 2.45 (d, 3H, J=3H), 2.23–2.29 (c, 1H), 1.94 (d, 1H, J=6 Hz), 1.60–1.70 (c, 1H), 1.21–1.31 (c, 2H), 1.00–1.10 (c, 1H), 0.88–1.00 (c, 2H), 0.72–0.82 (c, 1H), 0.49 (d, 3H, J=3 Hz), 0.43 (d, 3H, J=3 Hz), −0.01–(−0.09) (c 1H). 13C NMR (300 MHz, DMSO-d6) d 171.8, 171.2, 170.5, 159.5, 130.8, 130.6, 130.0, 119.2, 119.1, 70.3, 52.0, 49, 45.7, 38.5, 33.4, 30.2, 25.9, 25.4, 23.4, 22.5, 21.5, 21.4. MS (DCI/NH$_3$) m/e 420 (M+H)$^+$.

EXAMPLE 9

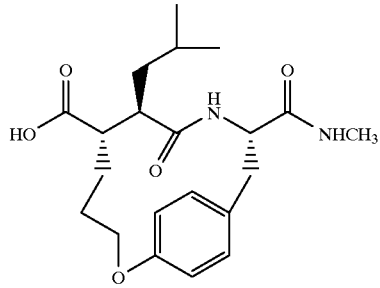

The desired compound was prepared according to the method of Examples 8C–F, except substituting allyl bromide for 4-bromo-1-butene in Example 8B.

EXAMPLE 10

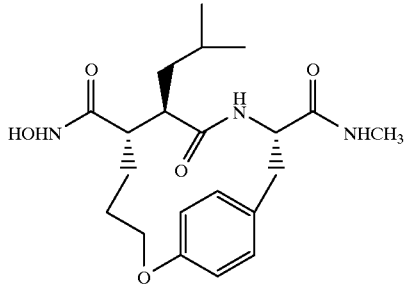

The desired compound was prepared from the compound of Example 9 according to the method of Example 8G. $^1$H NMR (300 MHz, DMSO-d6) δ 10.30 (s, 1H), 8.69 (bs, 1H), 7.81 (d, 1H, J=6 Hz), 7.62 (dd, 1H, J=3, 3 Hz), 7.05–7.17 (c, 3H), 6.81 (dd, 1H, J=4.5, 1.5 Hz), 4.65–4.73 (c, 1H), 4.08–4.15 (c, 1H), 3.98–4.05 (c, 1H), 3.15 (dd, 1H, J=3, 4.5 Hz), 2.62 (d, 3H, J=3 Hz), 2.54 (d, 1H, J=7.5 Hz), 2.00 (dt, 1H, J=6, 1.5 Hz), 1.59 (dt, 2H, J=7.5, 1.5 Hz), 1.10–1.27 (c, 4H), 0.73–0.79 (c, 7H), 0.70 (d, 2H, J=3 Hz), 0.57–0.68 (c, 1H), 0.61–72 (c, 1H). $^{13}$C NMR (300 MHz, DMSO-d6) d 172.7, 171.5, 169.6, 158.3, 132.7, 132.5, 128.9, 122.0, 120.0, 72.9, 53.0, 46.7, 46.1, 39.9, 36.7, 29.9, 29.3, 25.4, 25.1, 24.0, 21.2. IR (KBr) 3300, 2960, 2920, 1660, 1640, 1530, 1510, 1220 cm$^{-1}$. MS(FAB(+)) m/e 42(M+Na)$^+$, 406(M+H)$^+$.

EXAMPLE 11

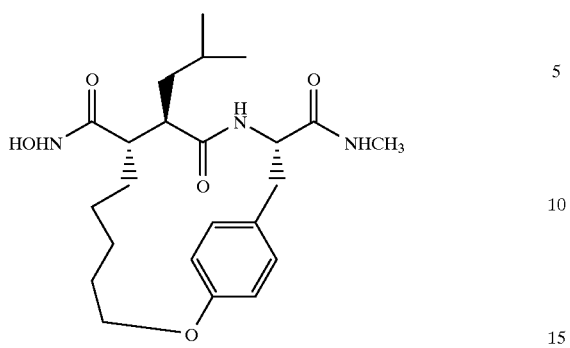

The desired compound was prepared according to the method of Example 1A–C, F and G, except substituting succinate ester 3 for succinate ester 1, and substituting 8e for benzyltyrosine tosylate salt. mp>300° C. $^1$H NMR (300 MHz, DMSO-d6) δ –0.25–(–0.1) (m, 1H), 0.6–0.71 (m, 1H), 0.72 (d, 3H, J=6.9 Hz), 0.82 (d, 3H, J=6.3 Hz), 0.85–1.39 (m, 8H), 1.4–1.59 (m, 1H), 1.6–1.75 (m, 1H), 2.14–2.24 (m, 1H), 2.58–2.60 (m, 1H), 2.61 (d, 3H, J=4.8 Hz), 2.86–2.91 (m, 1H), 4.08–4.22 (m, 2H), 4.4–4.55 (m, 1H), 6.81 (d, 1H, J=8.1 Hz), 6.92 (1, 8.1H), 7.2–7.24 (m, 2H), 7.71 (d, 1H, J=4.8 Hz), 7.93 (d, 1H, J=9 Hz), 8.69 (s, 1H), 10.3 (s, 1H). MS (DCI/NH$_3$) m/e 434 (M+H)$^+$. Anal. calcd for $C_{23}H_{35}N_3O_5 \cdot 0.5H_2O$: C, 62.42; H, 8.19; N, 9.49. Found: C, 62.69; H, 8.12; N, 9.45. [α]+31° (c 0.3, DMF).

EXAMPLE 12

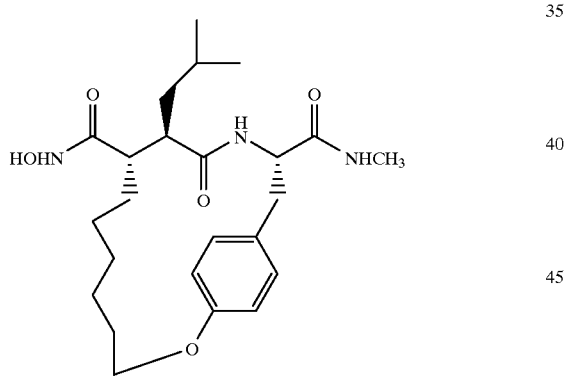

EXAMPLE 12A

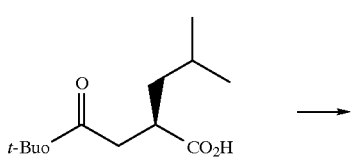

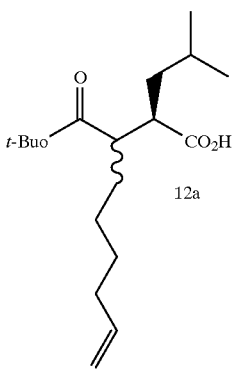

The desired compound 12a was prepared according to the method of Example 8B, except substituting 6-bromo-1-hexene for 4-bromo-1-butene.

EXAMPLE 12B

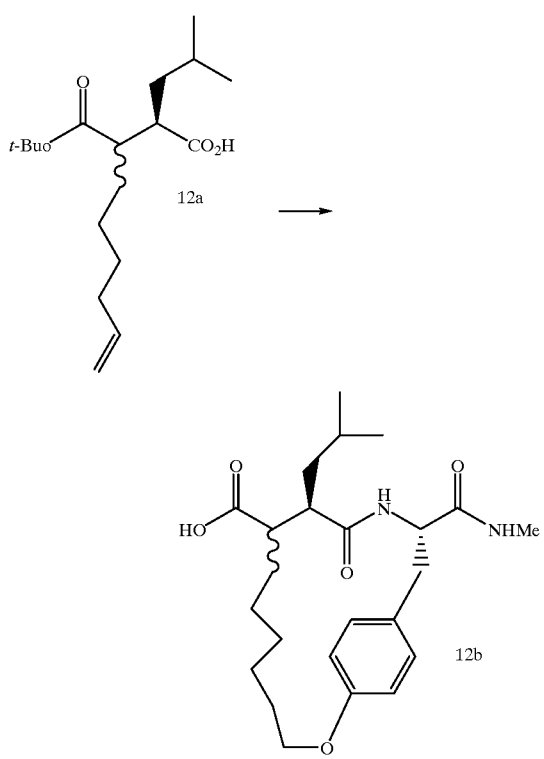

The desired compound was prepared according to the method of Examples 1A–F, except substituting 12a for succinate ester 1.

EXAMPLE 12C

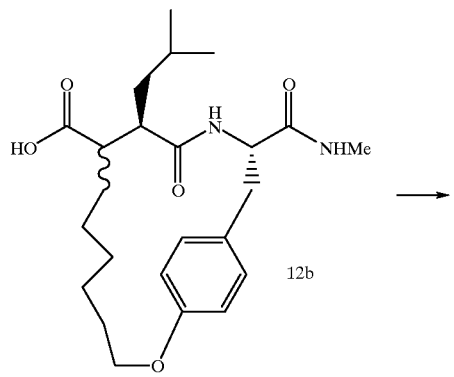

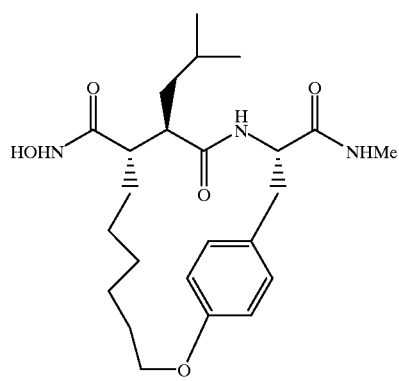

To a 0° C. solution of 12b (0.21, 0.49 mmol) in DMF (4 mL), was added NMM (200 μl, 1.8 mmol), HOBT (80mg, 0.59 mmol) and EDC (113 mg, 0.59 mmol). After 15 minutes at 0° C. O-benzylhydroxylamine hydrochloride (95 mg, 0.59 mmol) was added in a single portion and the mixture was allowed to warm to room temperature with stirring overnight. The turbid solution was added to water and 5% methanol/$CH_2Cl_2$. The aqueous layer was extracted twice with $CH_2Cl_2$ and the combined organic layers were concentrated. The crude material was triturated in 5:1 ether/methanol and the solid collected by filtration to give 109 mg of the O-benzylhydroxamate. This material was dissolved in 75 ml of 70:30 THF/MeOH and treated with 10 mg of 10% Pd/C under 1 atm of $H_2$ for 2 hours. The catalyst was filtered off and the solution concentrated to give the desired anti isomer (35 mg) as a white solid. $^1$H NMR (DMSO) δ 0.–0.2 (m, 1H), 0.73 (d, 3H, J=6.6 Hz), 0.75–1.15 (m, 6H), 0.85 (d, 3H, J=6.3 Hz), 1.2–1.44 (m, 3H), 1.5–1.8 (m, 4H), 2.2–2.32 (m, 1H), 2.60 (d, 3H, J=4.8 Hz), 2.62–2.73 (m, 1H), 2.80–2.90 (m,1H), 4.15–4.23 (m, 2H), 4.33–4.50 (m, 1H), 6.92 (d, 2H, J=8.1 Hz), 7.23 (d, 2H, J=8.4 Hz), 7.93 (d, 1H, J=4.2 Hz), 8.10 (d, 1H, J=8.4 Hz), 8.72 (s, 1H), 10.38 (s, 1H). MS (DCI/$NH_3$) m/e 448 (M+H)$^+$. Anal. calcd for $C_{24}H_{37}N_3O_5 \cdot 0.25H_2O$: C, 63.76; H, 8.36; N, 9.29. Found C, 6.74; H, 8.32; N, 8.43. [α]+2° (c 0.2, DMF).

EXAMPLE 13

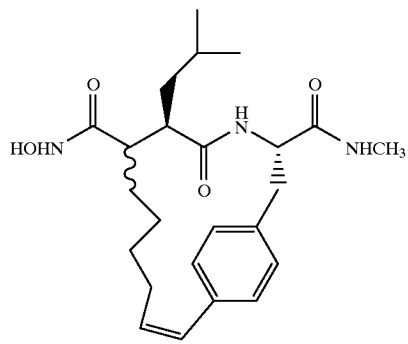

EXAMPLE 13A

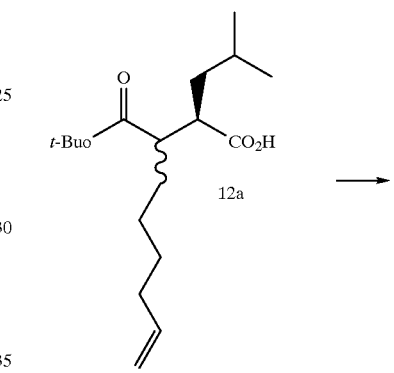

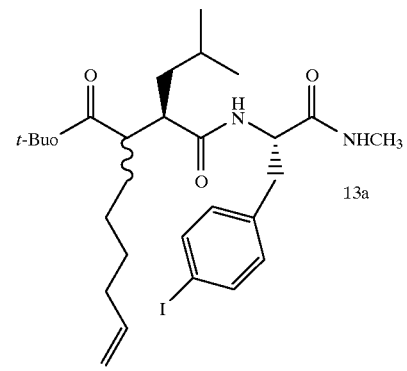

The desired compound 13a was prepared by coupling of 12a and p-iodo-phenylalanine-N-methylamide hydrochloride using the described above for the preparation of 1a.

EXAMPLE 13B

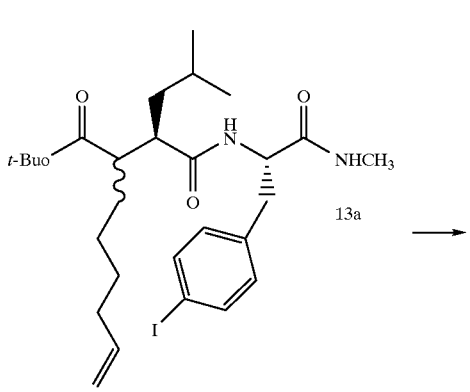

13a

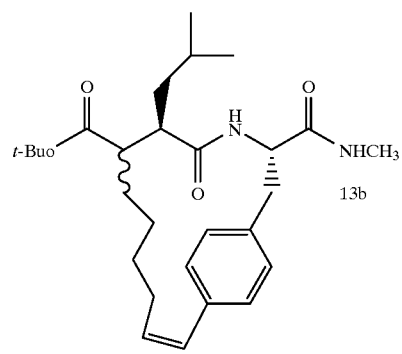

13b

To a solution of the compound of 13a (0.65 g, 1.93 mmol) in acetonitrile (25 mL) in a glass bomb was added triethylamine (1.63 ml, 16 mmol). Argon was bubbled through the solution for five minutes followed by rapid addition of tetrakis(triphenylphosphine)palladium(0) (127mg, 10 mol%). The bomb was then sealed and heated at 80° C. for 2hours. After cooling, the solution was concentrated and purified by flash chromatography (40% ethyl acetate-hexanes) to give the desired compound 13b (146 mg) as a white solid.

EXAMPLE 13C

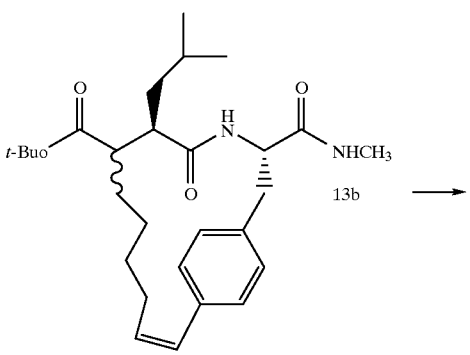

13b

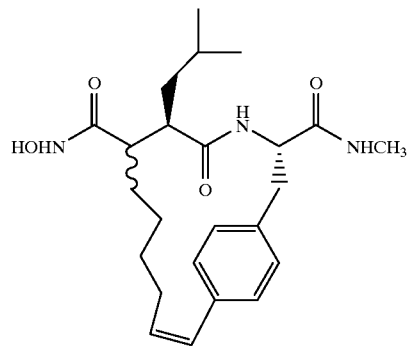

The desired compound was prepared from 13b according to the method of Examples 1F and G. $^1$H NMR (DMSO) δ −0.7–(−0.4) (m, 1H), 0.42–2.2 (series of m, 12H), 0.6–0.7 (narrow m, 3H), 0.8–0.9 (narrow m, 3H), 2.6–2.7 (narrow m, 3H), 3.0–3.2 (m, 3H), 4.2–5.0 (m, 3H), 7.0–8.0 (m, 6H), 8.6–8.7 (m, 1H). MS (DCI/NH$_3$) m/e 430 (M+H)$^+$.

EXAMPLE 14

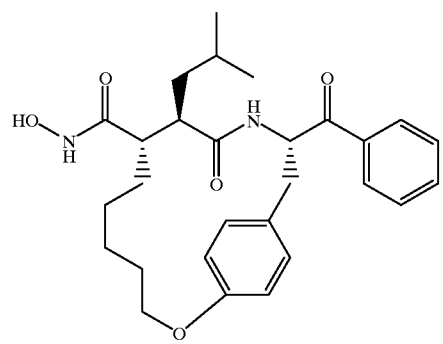

EXAMPLE 14A

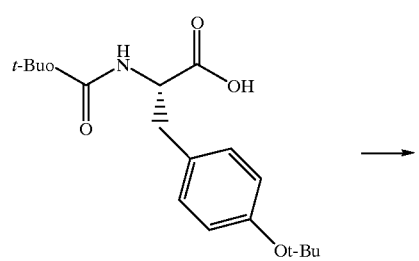

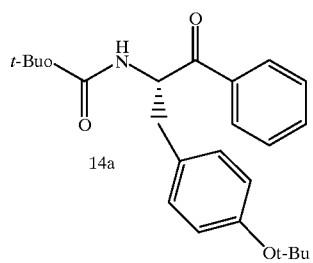

14a

To a 0° C. solution of nBuLi (2.5M/Hexanes, 14.25 mL) in diethyl ether (5 mL) was added bromobenzene (5.55 g, 35.6 mmol) over a few minutes. The resulting yellow solution allowed to stir cold for 45 minutes and then was cannulated into a −78° C. solution of N-Boc-O-tBu-L-tyrosine (3.0 g, 8.9 mmol) in diethyl ether (75 mL). The reaction mixture was warmed to 0° C. over 1.5 hours and then was quenched with 2N citric acid. The aqueous layer was extracted twice with diethyl ether and the combined organic extracts were washed with saturated aqueous NaHCO₃ and brine, dried (MgSO₄) and concentrated in vacuo. Flash chromatography (hexane-ethyl acetate 9:1) afforded the desired compound 14a (1.84 g) which was carried on without further purification.

EXAMPLE 14B

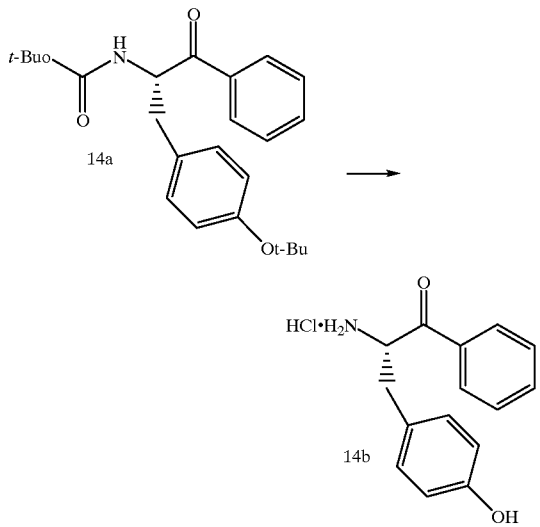

A solution of the 14a (1.8 g, 4.7 mmol) in trifluoroacetic acid was stirred at 0° for 30 minutes. The excess trifluoroacetic acid was evaporated in vacuo. The residue was taken up in 1N HCl in ether and stirred for 30 minutes. The mixture was diluted with diethyl ether (70 mL) and the resulting solid filtered. The extremely hygroscopic solid was dried in a vacuum oven for several hours, transferred into a round bottom flask and dried under high vacuum for 16 hours to give the desired compound 14b (0.48 g) as a hygroscopic, white HCl salt.

EXAMPLE 14C

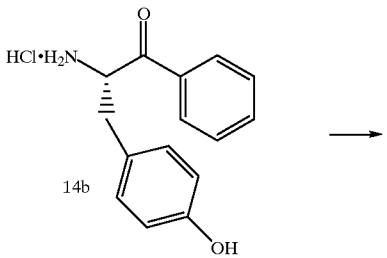

-continued

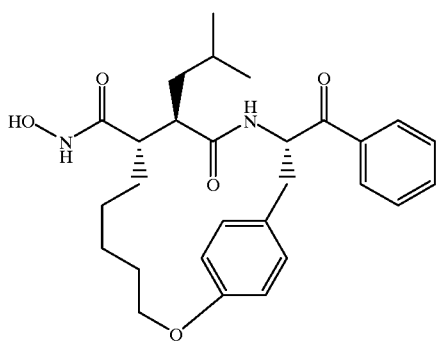

The desired compound was prepared from 14b and succinate ester 3 according to the method of Examples 1A–C. mp 210–220° (Dec). ¹H NMR (300 MHz, DMSO-d6) δ 10.30 (s, 1H), 8.63 (s, 1H), 8.17–8.14 (d, 9.2H), 8.10–8.07 (d, 2H, J=8.5 Hz), 7.66–7.63 (t, 1H, J=7.3 Hz), 7.56–7.51 (t, 2H, J=7.8 Hz), 7.43–7.40 (d, 1H, J=8.5 Hz), 7.25–7.22 (d, 1H, J=8.4 Hz), 6.96–6.94 (d, 1H, J=8.5 Hz), 6.85–6.83 (d, 1H, J=8.5 Hz), 5.68–5.61 (m, 2H), 3.09–3.03 (m, 1H), 2.77–2.68 (m, 1H), 2.17–2.13 (m, 1H), 1.71–1.69 (m, 1H), 1.50–1.49 (m, 1H), 1.34–1.31 (m, 2H), 1.16–1.05 (m, 3H), 0.78–0.62 (m, 5H), 0.47–0.45 (d, 3H, J=7.3 Hz), 0.00–(−) 0.08 (m, 1H). MS (DCI/NH₃) m/e 481 (M+H)⁺. Anal calcd for $C_{28}H_{36}N_2O_5 \cdot 0.5H_2O$: C, 68.68; H, 7.61; N, 5.72. Found: C, 68.88; H, 7.88; N, 5.10. [α]$_D$: +21.3° (c=0.46, DMF).

EXAMPLE 15

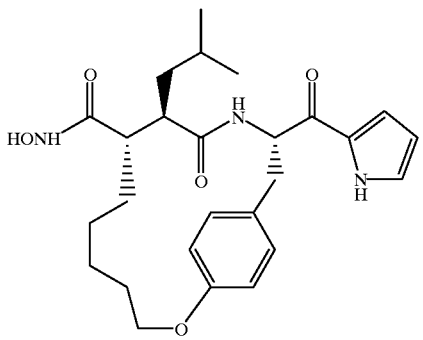

EXAMPLE 15A

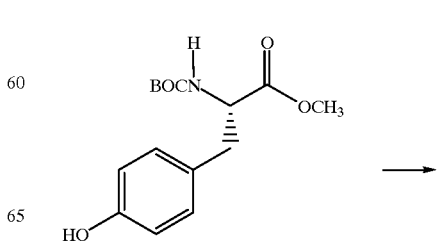

-continued

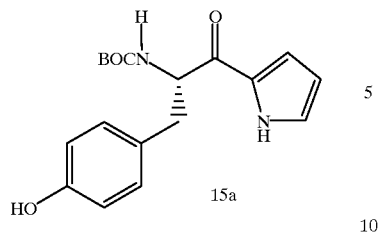

To a solution of methylmagnesium bromide (35 ml, 3.0M in Et₂O, 105.6 mmol) in dry toluene (140 ml) was added pyrrole (12 ml, 171.9 mmol) dropwise at −40° C. under nitrogen. The resulting solution was then stirred at −10° C. for 10 minutes and then was cannulated into a solution of BOC-L-tyrosine methyl ester (3.9 g, 13.2 mmol) in dry toluene (40 ml) at −65° C. The temperature was allowed to warm to −10° C. over 4 hours and the reaction was quenched by addition of 2N citric acid. The reaction mixture was extracted with CH₂Cl₂ (3×), dried over Na₂SO₄, filtered and the solvent was evaporated. The crude product was purified by flash chromatography (30% ethyl acetate-hexanes) to give the desired compound 15a (2.46 g, 56%) as a light brown foam.

EXAMPLE 15B

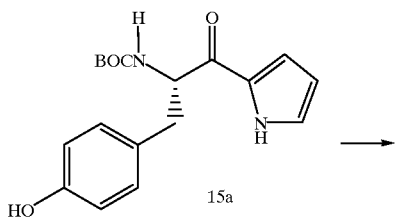

Compound 15a (720 mg, 2.18 mmol) was dissolved in trifluoroacetic acid (5 ml) and stirred at room temperature for 5 minutes. The solvent was evaporated to give 15b (900 mg) as a brown oil which was used without further purification.

EXAMPLE 15C

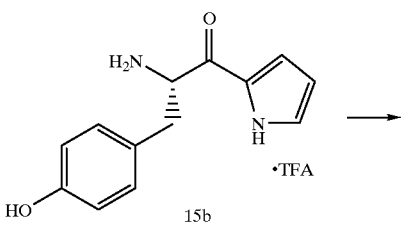

-continued

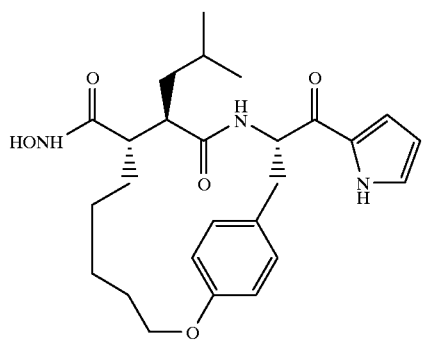

The desired compound was prepared according to the method of Example 14C, except substituting 15b for 14b. m.p. 242° C. (dec). 1H NMR (300 MHz, DMSO-d6) δ −0.02–(−0.15) (m, 1H), 0.53–0.88 (m, 4H), 0.61 (d, 3H, J=3 Hz), 0.79 (d, 3H, J=3 Hz), 0.90–1.04 (m, 1H), 1.07–1.40 (m, 5H), 1.42–1.60 (broad, 1H), 1.65–1.76 (dt, 1H, J=3, 9 Hz), 2.19–2.30 (dt, 1H, J=3, 12 Hz), 2.65–2.78 (1H), 3.0–3.1 (dd, 1H, J=3, 15 Hz), 4.04–4.07 (m, 2H), 5.21–5.32 (m, 1H), 6.24–6.28 (m, 1H), 6.81–6.88 (dd, 1H, J=3, 9 Hz), 6.91–6.99 (dd, 1H, J=3, 9 Hz), 7.14 (1H), 7.25–7.34 (m, 2H), 7.39–7.46 (dd, 1H, J=3, 9 Hz), 8.12 (d, 1H, J=9 Hz), 8.69 (s, 1H), 10.31 (s, 1H), 11.93 (s, 1H). MS (DCI/NH₃) m/e 470 (M+H)⁺. Anal calcd for C₂₆H₃₅N₃O₅·H₂O: C, 64.04; H, 7.64; N, 8.61. Found: C, 64.00; H, 7.61; N, 8.44. [α]_D: +97.3° (c=0.26, EtOH).

EXAMPLE 16

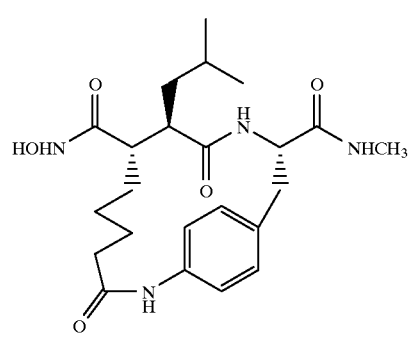

EXAMPLE 16A

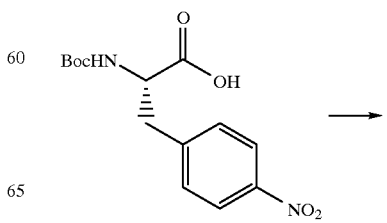

-continued

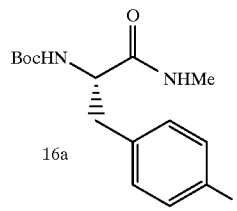

To a solution of N-tert-butoxycarbonyl p-nitro-phenylalanine (Sigma) (0.78 g, 2.51 mmol) in DMF (12.5 mL) was added EDC (0.53 g, 2.77 mmol), HOBT (0.37 g, 2.77 mmol), NMM (0.30 g, 2.77 mmol) and methylamine hydrochloride (0.19 g, 2.77 mmol) and the reaction mixture was stirred at room temperature for 2 hours. The reaction mixture was partitioned between ethyl acetate and brine. The aqueous layer was separated and extracted twice with ethyl acetate. The combined ethyl acetate extracts were washed with brine, dried over MgSO$_4$, filtered and evaporated to dryness. The crude material was purified by flash chromatography (60% ethyl acetate-hexanes) to give 16a (0.8 g, 98%).

EXAMPLE 16B

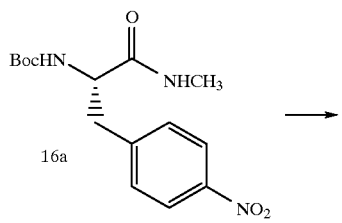

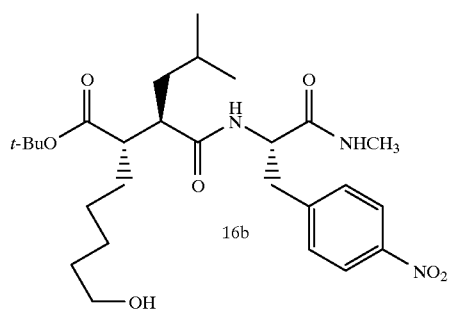

The desired compound was prepared by deprotection of 16a by treatment with trifluoroacetic acid according to the procedure of Example 15B, followed by coupling with succinate ester 3 and hydroboration/oxidation using the method of Examples 1A and B.

EXAMPLE 16C

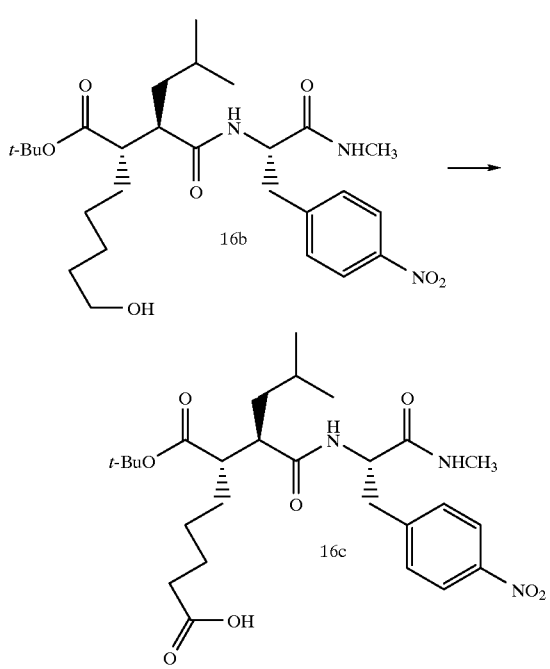

To a solution of the compound 16b (207 mg, 0.397 mmol) in CH$_2$Cl$_2$ was added Jones' reagent dropwise until the orange color of the reagent was preserved, then ethyl alcohol was added dropwise to quench the excess Jones' reagent (the color changed to green). The mixture was evaporated to a small volume and partitioned between CH$_2$Cl$_2$ and brine. The aqueous phase pH was adjusted to 2. The aqueous phase was extracted with CH$_2$Cl$_2$ (3×). The combined CH$_2$Cl$_2$ extracts were dried (MgSO$_4$), filtered and evaporated to give the desired compound 16c (209 mg) which was used without further purification.

EXAMPLE 16D

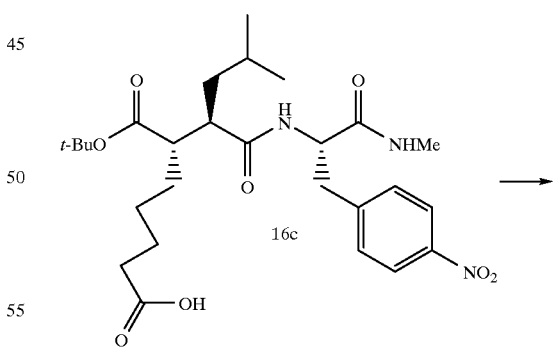

-continued

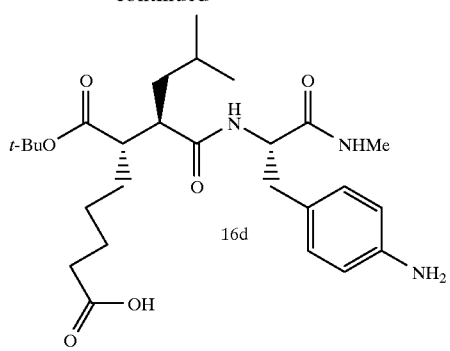

16d

A mixture of 16c (205 mg, 0.383 mmol) and 10% Pd/C (40 mg) in EtOH was stirred under H₂ (1 atm) for 2 hours. The reaction mixture was filtered through Celite and the residue was washed thoroughly with 10% methanol-CH₂Cl₂. The filtrate and washings were collected and evaporated to dryness to give 16d (193 mg) as a pale brown solid which was used without further purification.

EXAMPLE 16E

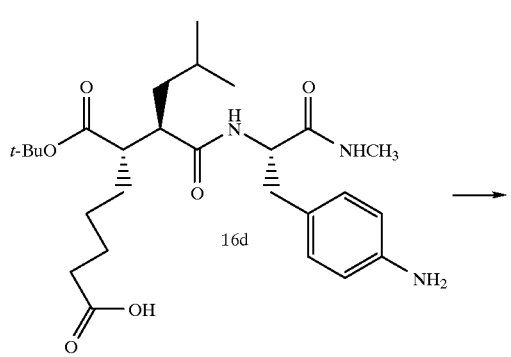

16d

16e

To a solution of 16d (190 mg, 0.376 mmol) in CH₂Cl₂ (4 mL) was added triethylamine (156.9 mL, 1.13 mmol) followed by bis(2-oxo-3-oxazolidinyl)phosphinic chloride (143.7 mg, 0.564 mmol). After stirring at room temperature for 2 hours, the mixture was poured into CH₂Cl₂ and washed with saturated aqueous NaHCO₃ and brine. The aqueous layer was then extracted twice with CH₂Cl₂. The combined CH₂Cl₂ layers were dried (MgSO₄), filtered and evaporated to dryness. Flash chromatography (2%–5% methanol—CH₂Cl₂) gave 16e (87.7 mg).

EXAMPLE 16F

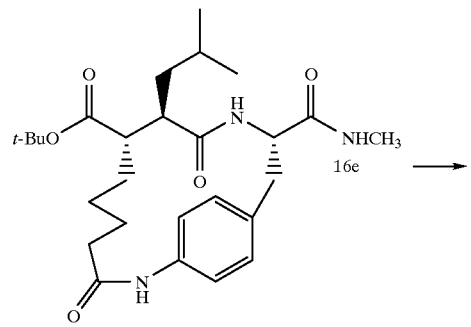

16e

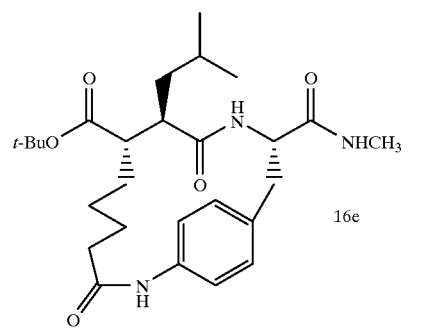

The desired compound was prepared from 16e according to the method of Examples 1F and G. mp: >250° C. ¹H NMR (300 MHz, DMSO-d6) δ -0.09 (m, 1H), 0.78 (d, 3H, J=6.2 Hz), 0.85 (d, 3H, J=6.2 Hz), 0.78–0.85 (m, 2H), 1.10–1.40 (m, 6H), 1.60–1.75 (m, 2H), 2.12 (m, 1H), 2.22 (m, 1H), 2.63 (d, 3H, J=4.5 Hz), 2.74 (t, 1H, J=13.2 Hz), 2.99 (dd, 1H, J=13.2, 3 Hz), 4.5 (m, 1H), 7.10 (m, 2H), 7.37 (m, 2H), 7.84 (bs, 1H), 8.08 (bs, 2H), 9.09 (s, 1H), 10.15 (bs, 1H). MS (DCI-NH₃) 447 (M+H)⁺, 429, 403, 283. [α]=+50.0° (c=0.11, CH₃OH).

EXAMPLE 17

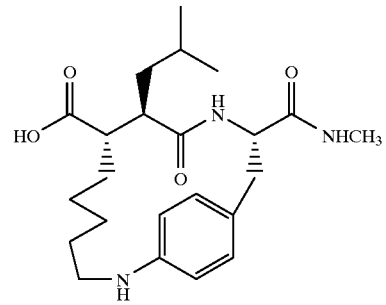

EXAMPLE 17A

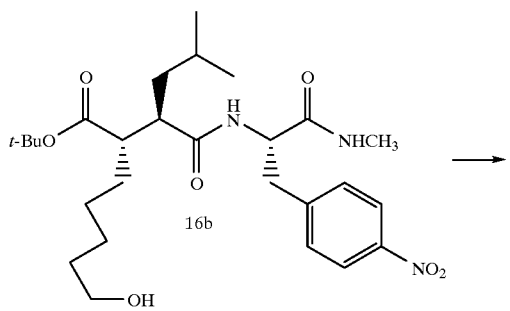

To a solution of 16b (449 mg, 0.863 mmol) in CH$_2$Cl$_2$ was added triethylamine (0.18 mL, 1.29 mmol) and methanesulfonyl chloride (0.080 mL, 1.04 mmol). After stirring at room temperature for 0.5 hours, the mixture was poured into CH$_2$Cl$_2$ and washed with NaHCO$_3$ and brine. The CH$_2$Cl$_2$ was dried (MgSO$_4$), filtered and evaporated to dryness. Flash chromatography (40–80% ethyl acetate-hexanes) gave 17a (428 mg, 83%) as white crystals.

EXAMPLE 17B

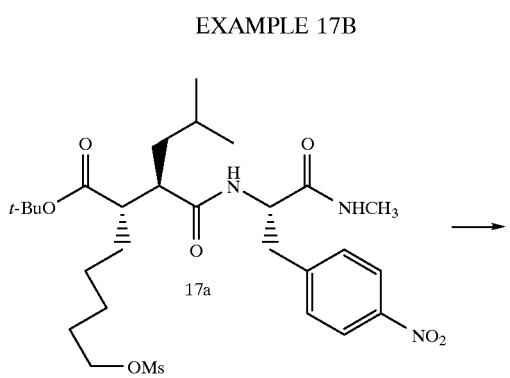

A mixture of 17a (420 mg, 0.701 mmol), 10% Pd/C (50 mg) and triethylamine (0.098 mL, 0.701 mmol) in isopropanol (4 mL) was stirred under H$_2$ (1 atm) for 10 hours. The reaction mixture was filtered through Celite and the residue was washed thoroughly with 10% methanol-CH$_2$Cl$_2$. The filtrate and washings were combined and evaporated to dryness. Flash chromatography (2–5% methanol-CH$_2$Cl$_2$) provided 17b (280.4 mg, 84.4%) as white crystals.

EXAMPLE 17C

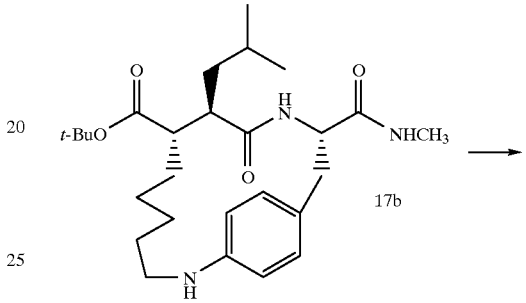

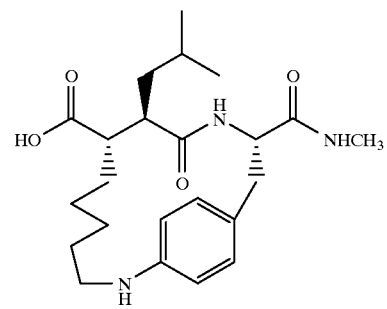

The desired compound was prepared from 17b according to the method of Example 1F. mp 194–196° C. (dec). $^1$H NMR (500 MHZ, DMSO-d6, 30° C.) δ 0.03 (t, 1H, J=11 Hz), 0.74 (d, 3H, J=6.1 Hz), 0.67–0.84 (m, 3H), 0.85 (d, 3H, J=6.1 Hz), 1.03–1.08 (m, 4H), 1.32–1.38 (m, 3H), 1.89 (dt, 1H, J=11.2, 3.4 Hz), 3.0 (dt, 1H, J=11.1, 3.4 Hz), 2.62 (d, 3H, J=4.8 Hz), 2.66 (t, 1H, J=12.5 Hz), 2.98 (dd, 1H, J=12.5, 4.2 Hz), 3.17 (m, 2H), 4.5 (m, 1H), 7 (bs, 1H), 7.09 (bs, 1H), 7.18 (bs, 1H), 7.31 (bs, 1H), 7.76 (q, 1H, J=4.8 Hz), 8.05 (d, 1H, J=9.1 Hz), 12.07 (bs, 1H). MS (DCI-NH$_3$) 418 (M+H)$^+$, 401, 229. Anal calcd for C$_{23}$H$_{35}$N$_3$O$_4$.1.8CF$_3$COOH.1.8H$_2$O: C, 48.83; H, 6.22; N, 6.42. Found: C, 48.68; H, 6.30; N, 6.73. [α]=−10.7° (c=0.14, CH$_3$OH)

EXAMPLE 18

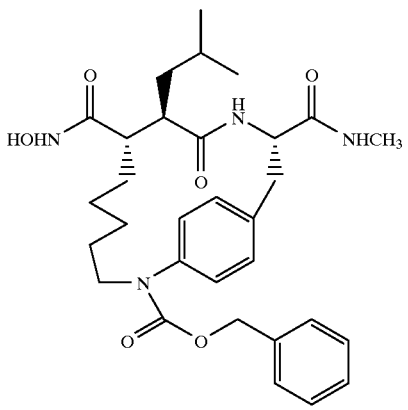

EXAMPLE 18A

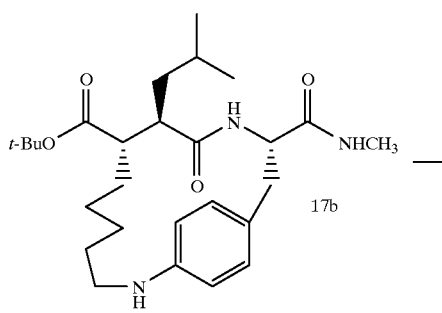

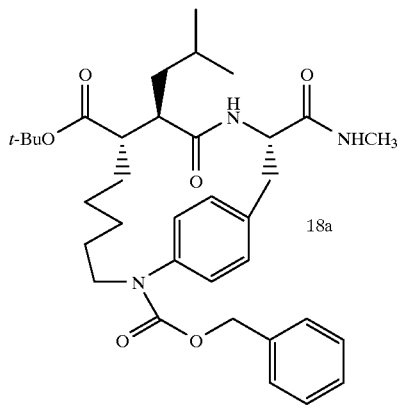

To a solution of 17b (230 mg, 0.486 mmol) in THF (4 mL) was added saturated NaHCO₃ (3 mL) followed by benzyl chloroformate (0.083 mL, 0.583 mmol). The mixture was stirrined at ambient temperature for 2 hours and then was evaporated to a small volume. The residue was partitioned between CH₂Cl₂ and brine. The aqueous layer was separated and extracted with twice with CH₂Cl₂ and the combined CH₂Cl₂ layers were dried, filtered and evaporated to dryness. Flash chromatography (60%–80% ethyl acetate-hexanes) yielded 18a (264 mg, 89.7%) as a white solid.

EXAMPLE 18B

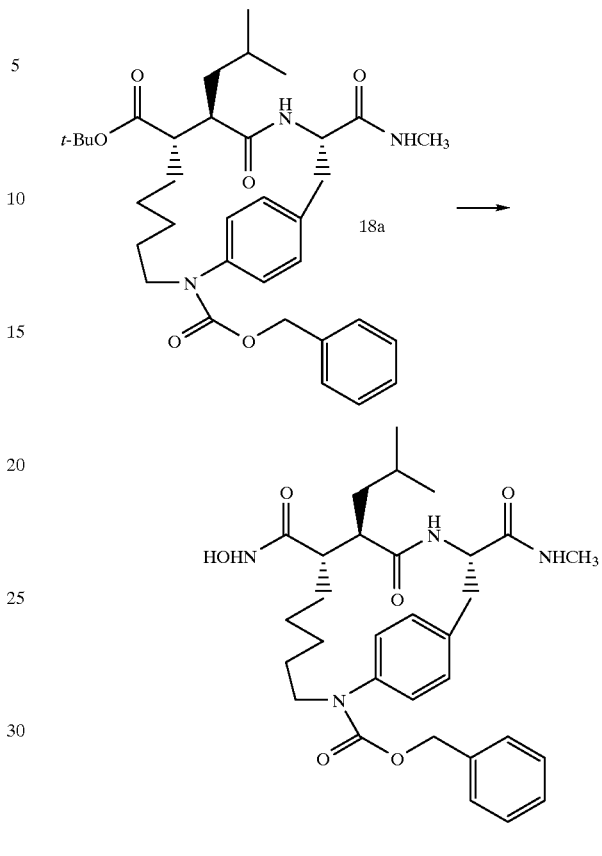

The desired compound was prepared from 18a according to the procedure of Examples 1F and G. mp: >250° C. $^1$H NMR (DMSO) δ 0.0 (m, 1H), 0.65–0.90 (m, 3H), 0.79 (d, 3H, J=6.2 Hz), 0.89 (d, 3H, J=6.2 Hz), 1.02–1.40 (m, 7H), 1.73 (dt, 1H, J=11.4, 3.0 Hz), 2.30 (dt, 1H, J=11.5, 3.0 Hz), 2.68 (d, 3H, J=4.8 Hz), 2.77 (d, 1H, J=13.2 Hz), 3.02 (dd, 1H, J=13.2, 3 Hz), 3.71 (m, 1H), 3.93 (m, 1H), 4.57 (m, 1H), 5.14 (s, 2H), 7.16 (dd, 1H, J=7.5, 0.6 Hz), 7.26 (m, 1H), 7.37–7.41 (m, 7H), 7.83 (q, 1H, J=4.8 Hz), 8.13 (d, 1H, J=9 Hz, 8.76 (s, 1H), 10.36 (s, 1H). MS (DCI-NH₃) m/e 567 (M+H)⁺, 523, 356. Anal. calcd for $C_{31}H_{42}N_4O_6 \cdot 0.4H_2O$: C, 64.87; H, 7.51; N, 9.76. Found: C, 64.79; H, 7.32; N, 9.8. [α]=−42.4° (c=0.13, CH₃OH)

EXAMPLE 19

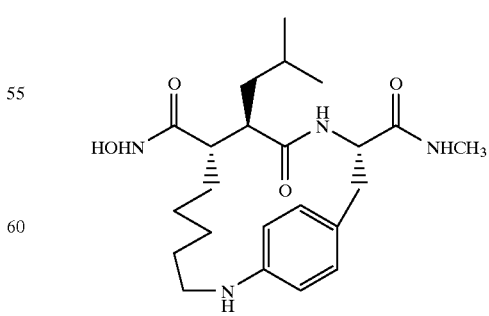

A mixture of the compound of Example 18 (27.0 mg, 0.048 mmol) and 10% Pd/C (5 mg) in THF-MeOH (10:1, 22 mL) was stirred under H₂ (1 atm) for 4 hours. The mixture was filtered through Celite, and the residue was washed thoroughly with 10% MeOH/CH₂Cl₂. The filtrate and washings were combined and evaporated to dryness. Flash chromatography (5%–8%–10% methanol-CH₂Cl₂) gave the desired compound (10.3 mg, 50%). mp 258–260° C. (dec). $^1$H NMR (500 MHz, DMSO-d6) δ −0.06 (t, 1H, J=11 Hz), 0.72 (d, 3H, J=6.5 Hz), 0.82 (d, 3H, J=6.5 Hz), 0.72–0.82 (m, 4H), 0.88–1.10 (m, 3H), 1.18–1.32 (m, 2H), 1.52 (bs, 1H), 1.52 (bs, 1H), 1.69 (m, 1H), 2.18 (m, 1H), 2.53 (d, 1H, J=13 Hz), 2.60 (d, 3H, J=4.5 Hz), 2.17 (dd, 1H, J=13, 2.5 Hz), 3.08 (bs, 2H), 4.42 (m, 1H), 5.11 (m, 1H), 6.50 (d, 1H, J=7.5 Hz), 6.59 (d, 1H, J=7.5 Hz), 7.02 (t, 2H, J=5.5 Hz), 7.60 (q, 1H, J=4.5 Hz), 7.81 (d, 1H, J=9 Hz), 8.64 (s, 1H), 10.27 (s, 1H). MS (DCI-NH₃) m/e 433 (M+H)⁺, 415, 389. Anal calcd for C₂₃H₃₆N₄O₄. 0.8 CF₃COOH.0.8 CH₃COOH.0.8 THF: C, 56.60; H, 7.70; N, 9.23. Found: C, 56.37; H, 7.79; N, 9.09.

EXAMPLE 20

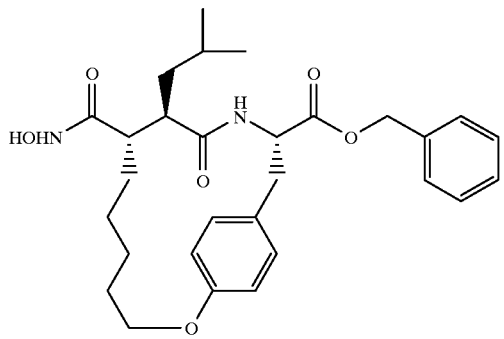

EXAMPLE 20A

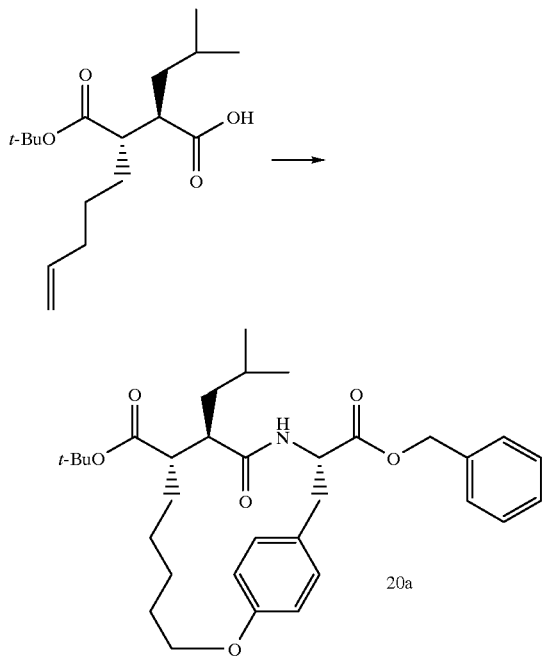

20a

The desired compound was prepared according to the method of Examples 1A–C, F and G, except substituting succinate ester 3 for succinate ester 1. mp>270° C. $^1$H NMR (DMSO) δ −0.3–(−0.1) (m, 1H), 0.6–0.9 (m, 3H), 0.63 (d, 3H, J=6.6 Hz), 0.72 (d, 3H, J=6.6 Hz), 0.9–1.0 (m, 1H), 1.0–1.6 (m, 6H), 0.6–0.7 (m, 1H), 2.19 (dt, 1H, J=11.1, 3.3 Hz), 2.67 (t, 1H, J=13.2 Hz), 3.2 (dd, 1H, J=13.2, 3.3 Hz), 4.1–4.3 (m, 2H), 4.7–4.8 (m, 1H), 5.15 (apparent AB, 2H, J=12.6 Hz), 6.8–7.0 (m, 2H), 7.22 (d, 2H, J=8.4 Hz), 7.3–7.4 (m, 5.15H), 8.12 (d, 1H, J=9.0 Hz), 8.69 (s, 1H), 10.3 (s, 1H). MS (DCI/NH₃) 511 (M+H)⁺. Anal calcd for C₂₉H₃₈N₂O₆.0.5H₂O: C, 67.03; H, 7.56; N, 5.39. Found: C, 67.18; H, 7.5; N, 5.32. [α]+9° (c 0.4, MeOH).

EXAMPLE 21

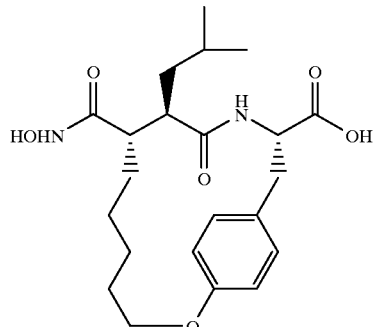

The desired compound was prepared by hydrogenation of the compound of Example 20 using the procedure of Example 1D except substituting THF for methanol. mp>250° C. $^1$H NMR (DMSO) δ −0.2–(−0.1) (m, 1H), 0.6–1.4 (m, 9H), 0.72 (d, 3H, J=6.6 Hz), 0.83 (d, 3H, J=6.6 Hz), 1.4–1.6 (m, 2H), 1.6–1.75 (m, 1H), 2.15–2.3 (m, 1H), 2.62 (t, 1H, J=12.9 Hz), 3.1–3.2 (m, 1H), 4.1–4.25 (m, 2H), 4.5–4.6 (m, 1H), 6.8–7.0 (m, 2H), 7.20 (apparent t, 2H, J=8.4 Hz), 7.99 (d, 1H, J=9.3 Hz), 8.70 (s, 1H), 10.3 (s, 1H). $^{13}$C NMR (DMSO) δ 21.45, 21.53, 22.0, 22.1, 24.1, 24.3, 24.5, 25.4, 28.1, 35.7, 40.9, 46.1, 46.2, 53.3, 65.9, 114.7, 117.7, 118.5, 128.3, 129.7, 130.4, 131.1, 154.0, 170.0, 173.0, 173.1. MS (DCI/NH₃) m/e 421 (M+H)⁺. Anal calcd for C₂₂H₃₂N₂O₆.1.4H₂O: C, 59.28; H, 7.87; N, 6.28. Found C, 59.36; H, 7.51; N, 6.13. [α]+28° (c 0.3, MeOH).

EXAMPLE 22

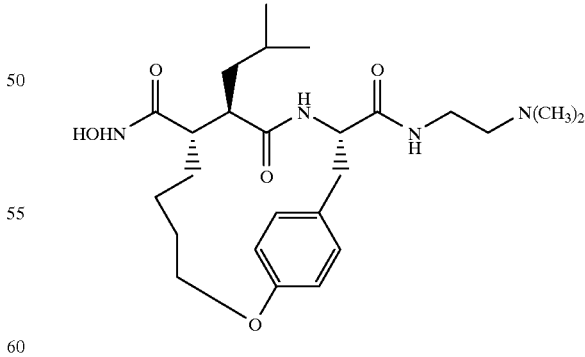

The desired compound was prepared according to the method of Examples 1E, F and G, except substituting N,N-dimethylethylenediamine for 4-(2-aminoethyl) benzenesulphonamide. mp 121–124° C. $^1$H NMR (DMSO) δ −0.6–(−0.4) (m, 1H), 0.6–1.0 (m, 3H), 0.71 (d, 3H, J=6.6 Hz), 0.79 (d, 3H, J=6.6 Hz), 1.1–1.4 (m, 3H), 1.5–1.7 (m, 3H), 2.0–2.2 (m, 1H), 2.62 (t, 1H, J=13.5 Hz), 3.0–3.2 (m, 3H), 3.3–3.6 (m, 2H), 3.9–4.1 (m, 2H), 4.4 (br s, 1H), 4.6–4.7 (m, 1H), 6.92 (d, 2H, J=8.4 Hz), 7.15–7.30 (m, 2H), 7.84 (d, 1H, J=9.3 Hz), 8.15 (t, 1H, J=5.7 Hz), 9.50 (br s, 1H). MS (DCI/NH$_3$) m/e 477 (M+H)$^+$. Anal calcd for $C_{25}H_{40}N_4O_5 \cdot 1.5$ TFA$\cdot 0.3H_2O$: C, 51.50; H, 6.50; N, 8.58. Found: C, 51.53; H, 6.62; N, 8.39. [α]+41° (c 0.3, H$_2$O).

EXAMPLE 23

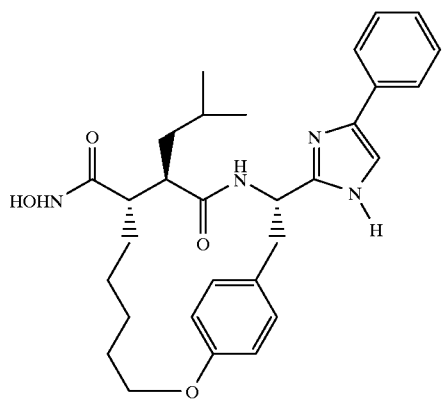

EXAMPLE 23A

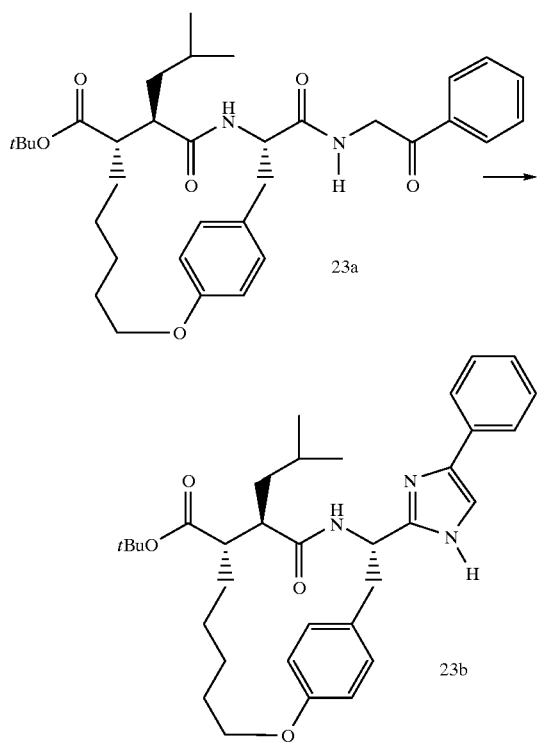

A solution of 23a (1.19 g, 2.06 mmol, prepared according to the method of Examples 1A–E, except substituting succinate ester 3 for succinate ester 1, and substituting commercially available 2-amlnoacetophenone hydrochloride for 4-(2-aminoethyl)benzenesulphonamide) and ammonium acetate (4.56 g, 59.4 mmol) in 10 mL acetic acid at 115° C. was stirred for 6 hours and then cooled to ambient temperature. The acetic acid was removed under vacuum and the orange solid was redissolved in 100 mL ethyl acetate and 50 mL H$_2$O. The aqueous layer was extracted with ethyl acetate (2×) and the combined organic layers were washed with saturated aqueous NaHCO$_3$ and brine, dried with MgSO$_4$, filtered and concentrated. This material was flash chromatographed (CH$_2$Cl$_2$ then 2% MeOH/CH$_2$Cl$_2$) to give 23b (856 mg) as a brick-red foam.

EXAMPLE 23B

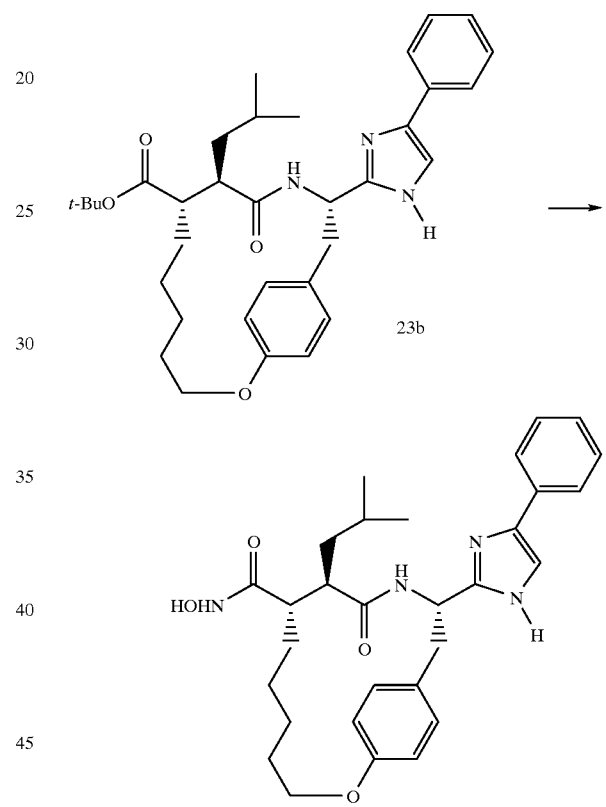

The desired compound was prepared as a white solid from 23b using the procedure of Examples 1F and G. mp>250° C. $^1$H NMR (DMSO) δ −0.1–0 (m, 1H), 0.6–0.9 (m, 1H), 0.68 (d, 3H, J=6.3 Hz), 0.85 (d, 3H, J=6.3 Hz), 0.9–1.4 (m, 7H), 1.4–1.8 (m, 3H), 2.22–2.3 (m, 1H), 2.88 (t, 1H, J=12.9 Hz), 3.22 (dd, 1H, J=13.5, 4.2 Hz), 4.1–4.3 (m, 2H), 5.1–5.3 (m, 1H), 6.8–7.0 (m, 2H), 7.1–7.2 (m, 1H), 7.25–7.35 (m, 4H), 7.53 (d, 1H, J=1.8 Hz), 7.76 (d, 2H, J=6.9 Hz), 8.01 (d, 1H, J=9.3 Hz), 8.66 (s, 1H), 10.3 (s, 1H), 11.8 (s, 1H). MS (DCI/NH$_3$) m/e 519 (M+H)$^+$. Anal calcd for $C_{30}H_{38}N_4O \cdot 1.3H_2O$: C, 66.47; H, 7.55; N, 10.34. Found: C, 66.60; H, 7.60; N, 10.23. [α]−35° (c 0.8, MeOH).

EXAMPLE 24

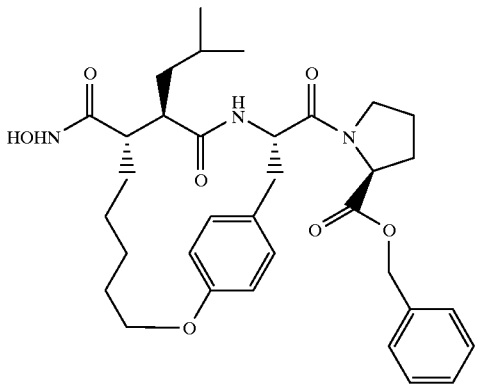

The desired compound was prepared according to the method of Examples 1A–C, F and G, except substituting commercially succinate ester 3 for succinate ester 1, and substituting commercially-available O-benzyl-(L)-proline hydrochloride for 4-(2-aminoethyl)benzenesulphonamide. mp>250° C. $^1$H NMR (DMSO) δ −0.3–(−) (m, 1H), 0.6–0.9 (m, 3H), 0.70 (d, 3H, J=6.6 Hz), 0.81 (d, 3H, J=6.6 Hz), 0.9–1.0 (m, 1H), 1.0–1.4 (m, 5H), 1.4–1.6 (m, 1H), 1.6–1.7 (m, 1H), 1.8–2.1 (m, 3H), 2.1–2.3 (m, 2H), 2.60 (t, 1H, J=13.2 Hz), 2.8–2.9 (m, 1H), 3.75–3.85 (m, 2H), 4.1–4.3 (m, 2H), 4.37 (dd, 1H, J=8.7, 5.1 Hz), 4.7–4.8 (m, 1H), 5.13 (AB pattern, 2H), 6.8–7.0 (m, 2H), 7.26 (d, 2H, J=9.0 Hz), 7.3–7.4 (m, 5H), 8.07 (d, 1H, J=9.0 Hz), 8.69 (s, 1H), 10.3 (s, 1H). MS (DCI/NH$_3$) m/e 608 (M+H)$^+$. Anal calcd for: C$_{34}$H$_{45}$N$_3$O$_7$.0.8H$_2$O: C, 65.64; H, 7.55; N, 6.75. Found: C, 65.69; H, 7.09; N, 6.68. [α]−9° (c 0.3, MeOH).

EXAMPLE 25

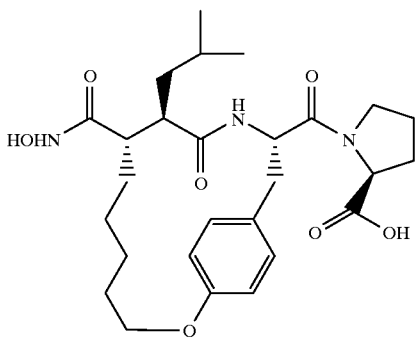

The desired compound was prepared as an off-white solid from the compound of Example 24 using the hydrogenolysis procedure of Example 21. mp>250° C. $^1$H NMR (DMSO) δ −0.2–(−0.1) (m, 1H), 0.6–0.8 (m, 3H), 0.70 (d, 3H, J=6.6 Hz), 0.81 (d, 3H, J=6.6 Hz), 0.9–1.0 (m, 1H), 1.0–1.4 (m, 5H), 1.4–1.6 (m, 1H), 1.6–1.7 (m, 1H), 1.8–2.1 (m, 3H), 2.1–2.3 (m, 2H), 2.65 (t, 1H, J=13.2 Hz), 2.9–3.0 (m, 1H), 3.7–3.9 (m, 2H), 4.1–4.3 (m, 3H), 4.6–4.7 (m, 1H), 6.8–7.0 (m, 2H), 7.2–7.3 (m, 2H), 8.06 (d, 1H, J=9.3 Hz), 8.68 (s, 1H), 10.3 (s, 1H), 12.1–12.4 (br s, 1H). $^{13}$C NMR (DMSO) δ 21.7, 22.2, 24.2, 24.7, 24.9, 25.5, 28.3, 28.7, 35.1, 40.8, 46.1, 46.3, 46.6, 52.4, 58.7, 66.1, 117.9, 118.6, 128.7, 130.4, 131.4, 154.1, 169.8, 170.1, 173.0, 173.4. MS (DCI/NH$_3$) m/e 518 (M+H)$^+$. Anal calcd for C$_{27}$H$_{39}$N$_3$O$_7$.1.0H$_2$O: C. 60.54,;H, 7.71; N, 7.84. Found: C, 60.53; H, 7.73; N, 7.51. [α]+16° (c 0.3, MeOH).

EXAMPLE 26

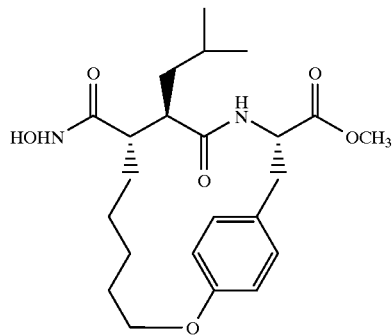

The desired compound was prepared as an off-white solid according to the method of Examples 1A–E, except substituting succinate ester 3 for succinate ester 1 and omitting 4-(2-aminoethyl)benzenesulphonamide and substituting methanol for DMF in Example 1E. mp>250° C. $^1$H NMR (DMSO) δ −0.25–(−0.1) (m, 1H), 0.6–1.0 (m, 4H), 0.75 (d, 3H, J=6.6 Hz), 0.84 (d, 3H, J=6.6 Hz), 1.0–1.2 (m, 2H), 1.2–1.4 (m, 2H), 1.4–1.6 (m, 1H), 2.22 (dt, 1H, J=11.4, 3.3 Hz), 2.64 (t, 1H, J=13.2 Hz), 3.1–3.2 (m, 1H), 3.65 (s, 3H), 4.1–4.3 (m, 2H), 4.6–4.7 (m, 1H), 6.8–7.0 (m, 2H), 7.2–7.25 (m, 2H), 8.10 (d, 1H, J=9.6 Hz), 8.71 (s, 1H), 10.33 (s, 1H). $^{13}$C NMR (DMSO) δ 6 21.4, 22.1, 24.0, 24.3, 24.6, 25.4, 28.1, 35.4. 40.9, 46.15, 46.24, 51.8, 52.9, 65.9, 117.8, 118.6, 128.3, 129.9, 131.2, 154.1, 169.9, 172.0, 173.2. MS (DCI/NH$_3$) m/e 435 (M+H)$^+$. Anal calcd for C$_{23}$H$_{34}$N$_2$O$_6$.0.4H$_2$O: C, 62.54; H, 7.94; N, 6.34. Found: C, 62.59; H, 7.81; N, 6.22. [α]+24° (c 0.3, MeOH).

EXAMPLE 27

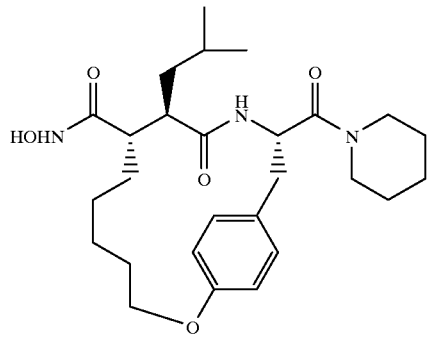

The desired compound was prepared as a white solid according to the method of Example 1, except substituting succinate ester 3 for succinate ester 1 and substituting piperidine for 4-(2-aminoethyl)benzenesulphonamide. mp>250° C. $^1$H NMR (DMSO) δ −0.2–0 (m, 1H), 0.6–0.8 (m, 1H), 0.71 (d, 3H, J=6.6 Hz), 0.81 (d, 3H, J=6.3 Hz), 0.9–1.05 (m, 1H), 1.05–1.8 (m, 14H), 2.1–2.2 (m, 1H), 2.7–2.8 (m, 2H), 3.2–3.3 (m, 1H), 3.5–3.7 (m, 3H), 3.75–3.85 (m, 1H), 4.0–4.3 (m, 2H), 4.9–5.0 (m, 1H), 6.8–6.9 (m, 1H), 6.9–7.0 (m, 1H), 7.2–7.3 (m, 2H), 8.03 (d, 1H, J=9.0 Hz), 8.67 (d, 1H, J=1.5 Hz), 10.29 (d, 1H, J=1.5 Hz). $^{13}$C NMR (DMSO) δ 21.7, 22.1, 24.1. 24.2, 24.9, 25.3, 25.5, 26.3, 28.2, 35.9, 40.9, 42.5, 46.0, 46.3, 49.8, 66.0, 17.9, 118.3, 118.4, 128.8, 130.5, 131.4. 154.1, 169.5, 170.1, 172.7. MS (DCI/NH$_3$) m/e 488 (M+H)$^+$. Anal calcd for C$_{27}$H$_{41}$N$_3$O$_5$.0.4H$_2$O: C, 65.54; H, 8.51; N. 8.49. Found C, 65.64; H, 8,49; N. 8.39. [α]+78° (c 0.25, MeOH).

EXAMPLE 28

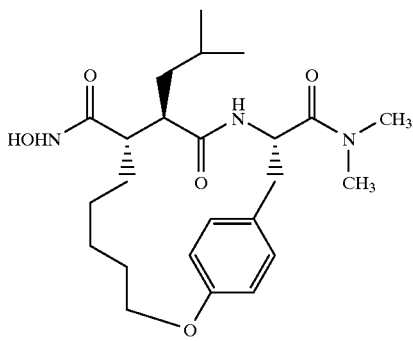

The desired compound was prepared as a white solid according to the method of Example 1, except substituting succinate ester 3 for succinate ester 1 and substituting dimethylamine hydrochloride for 4-(2-aminoethyl) benzenesulphonamide. mp>250° C. $^1$H NMR (DMSO) δ −0.2–0.0 (m, 1H), 0.6–0.8 (m, 2H), 0.71 (d, 3H, J=6.6 Hz), 0.81 (d, 3H, J=6.3 Hz), 0.9–1.0 (m, 1H), 1.1–1.6 (m, 6H), 1.65–1.75 (m, 1H), 2.20 (dt, 1H, J=11.1, 3.0 Hz), 2.66 (t, 1H, J=12.9 Hz), 2.84 (s, 3H), 2.8–2.9 (m, 1H), 3.19 (s, 3H), 4.05–4.25 (m, 2H), 4.9–5,0 (m, 1H), 6.8–7.0 (m, 2H), 7.2–7.3 (m, 2H), 8.03 (d, 1H, J=9.3 Hz), 8.67 (d, 1H, J=2.1 Hz), 10.30 (d, 1H, J=1.5 Hz). MS (DCI/NH$_3$) m/e 448 (M+H)$^+$. Anal calcd for $C_{24}H_{37}N_3O_5 \cdot 0.7H_2O$: C, 62.64; H, 8.41; N, 9.13. Found: C, 62.80; H, 8.30; N, 8.87. [α]+53° (c 0.3, MeOH).

EXAMPLE 29

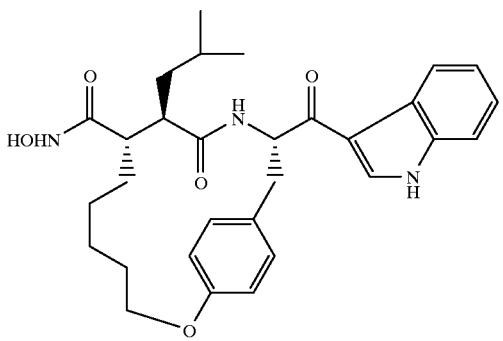

EXAMPLE 29A 1-tert-butyldimethylsilyl-3-bromoindole

To a cold (−78°) solution of indole (4.0 g, 34 mmol) in THF (120 mL) was added nBuLi (2.5M/Hexanes) over 5 minutes. The solution was warmed to −10° (ice/salt bath) for 15 minutes, re-cooled to −78° and TBDMS-Cl (5.8 g, 38 mmol) was added in THF (30 mL). The solution was held at 0° for 3 hours, cooled to −78° and N-Bromosuccinimide (6.0 g, 34 mmol) was added in one portion. The solution was stirred coldfor 2 hours and then was allowed to warm to ambient temperature at which time hexane/pyridine (100 mL) was added to the solution and the resulting suspension was filtered over Celite. The organics were evaporated and the residue quickly purified by flash chromatography (hexanes/methylene chloride 2:1) giving 8.5 g of the desired compound as a slightly purple solid.

EXAMPLE 29B

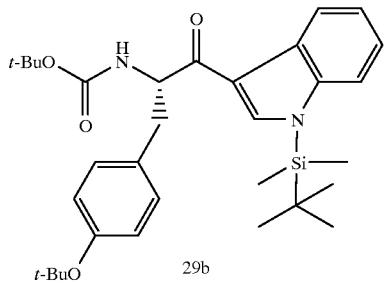

To a 0° C. solution of nBuLi (2.5M/hexanes, 9.6 mL) in diethyl ether (10 mL) was added 1-tert-butyldimethylsilyl-3-bromoindole (7.4 g, 24 mmol) in diethyl ether (5 mL). The resulting pale yellow solution was stirred cold for 25 minutes then was added to a −78° C. solution of N-tert-butoxycarbony-O-tert-butyl-L-tyrosine (2.0 g, 6 mmol) in diethyl ether (150 mL). The solution was warmed to 0°, held for 1 hour, and quenched with saturated aqueous NH$_4$Cl (25 mL). The aqueous layer was extracted with diethyl ether (3×), and the combined organics washed with saturated aqueous NaHCO$_3$ and brine, dried (MgSO$_4$) and concentrated. Flash chromatography (gradient elution; 0.5–2% acetone/hexane) gave 0.5 g of 29b as a reddish foam.

EXAMPLE 29C

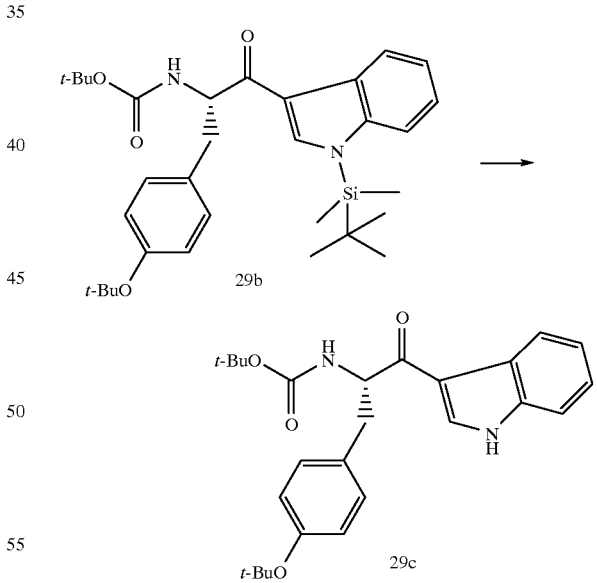

To a solution of 29b (1.41 g, 2.56 mmol) in 30 mL dry THF was added 2.6 mL tetrabutylammonium fluoride (1M in THF) over 1 minute. The greenish solution was stirred at ambient temperature for 1 hour and diluted with diethyl ether. The organics were washed with water (2×) and brine, dried (MgSO$_4$), filtered and concentrated in vacuo to give 29c (1.3 g) as a reddish foam.

EXAMPLE 29D

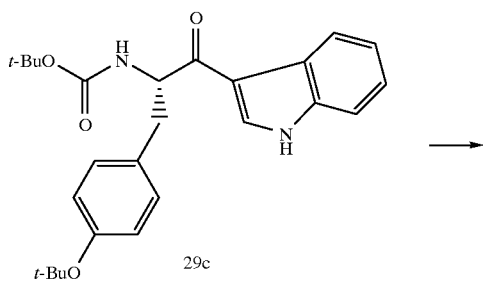

The desired compound was prepared according to the method of Examples 14B and C, except substituting 29c for 14a. mp 250° (dec). $^1$H NMR (DMSO-d$_6$) δ 12.00 (s, 1H), 10.28 (s, 1H), 8.65 (s, 1H), 8.59 (s, 1H), 8.21–8.15 (m, 2H), 7.48–7.44 (m, 2H), 7.29–7.16 (m, 3H), 6.91–6.82 (m, 2H), 5.41–5.38 (m, 1H), 4.31–4.05 (m, 2H), 3.06–3.01 (m, 1H), 2.88–2.80 (m, 1H), 2.25–2.17 (m, 1H), 1.72–1.71 (m, 1H), 1.81–1.67 (m, 1H), 1.35–1.23 (m, 1H), 1.16–106 (m, 4H), 0.77–0.43 (m, 8H), 0.01–(−)0.06 (m, 1H). MS (DCI/NH$_3$) m/e 520 (M+H)$^+$. [α]$_D$: +12.5°(c=0.12, DMF).

EXAMPLE 30

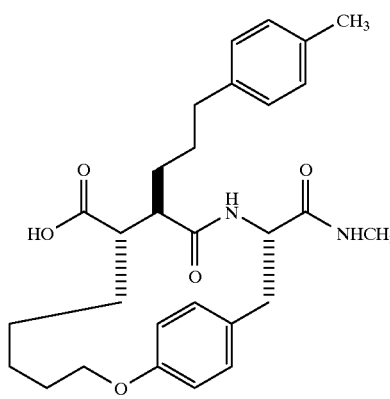

The desired compound was prepared according to the method of Examples 1A, B, C and F, except substituting succinate ester 4 for succinate ester 1, and substituting L-tyrosine N-methylamide hydrochloride for benzyltyrosine tosylate salt. mp>270° C. $^1$H NMR (300 MHz, DMSO-d6) δ 0.02–(−0.11) (complex, 1H), 0.56–0.85 (complex, 2H), 0.91–1.56 (complex, 10H), 1.86–1.97 (m, 1H), 2.08–2.19 (m, 1H), 2.24 (s, 3H), 2.30–2.64 (complex, 3H), 2.57 (d, 3H, J=5.1 Hz), 2.95 (dd, 1H, J=12.9, 3.0 Hz), 4.05–4.16 (m, 1H), 4.16–4.26 (m, 1H), 4.50 (m, 1H), 6.81 (dd, 1H, J=2.1, 8.4 Hz), 6.93 (dd, 1H, J=2.1, 8.4 Hz), 6.98–7.07 (complex, 4H), 7.15 (m, 1H), 7.22 (m, 1H), 7.75 (m, 1H), 8.12 (d, 1H, J=9.0 Hz), 12.08 (s, 1H). MS (DCI/NH$_3$) 495 (M+H)$^+$, 391. Anal calcd for C$_{29}$H$_{38}$N$_2$O$_5$: C, 70.41; H, 7.74; N, 5.66. Found: C, 70.19; H, 7.66; N, 5.85.

EXAMPLE 31

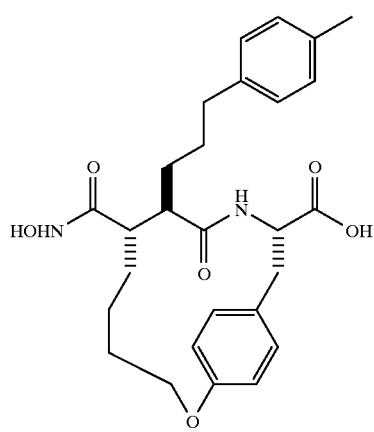

The desired compound was prepared from the compound of Example 30 according to the procedure of Example 1G. mp>270° C. $^1$H NMR (300 MHz, DMSO-d6) δ −0.22–(−0.12) (complex, 1H), 0.62–0.73 (complex, 2H), 0.88–1.57 (complex, 9H), 1.68–1.79 (complex, 1H), 2.14 (m, 1H), 2.23–2.37 (m, 1H), 2.25 (s, 3H), 2.41–2.64 (m, 2H), 2.54 (d, 3H, J=4.2 Hz), 2.94 (m, 1H), 4.06–4.26 (m, 2H), 4.47 (m, 1H), 6.81 (dd, 1H, J=2.4, 7.8 Hz), 6.92 (dd, 1H, J=2.7, 8.1 Hz), 6.99–7.07 (complex, 4H), 7.16 (dd, 1H, J=2.4, 8.7 Hz), 7.22 (dd, 1H, J=2.4, 8.7 Hz), 7.66 (m, 1H), 8.05 (d, 1H, J=9.0 Hz), 8.70 (s, 1H), 10.33 (s, 1H). MS (APCI) 510 (M+H)$^+$, 492, 477, 461. Anal. Calcd for C$_{29}$H$_{39}$N$_3$O$_5$: C, 68.34; H, 7.71; N, 8.24. Found: C, 68.07; H, 8.00; N, 8.16.

EXAMPLE 32

EXAMPLE 32A

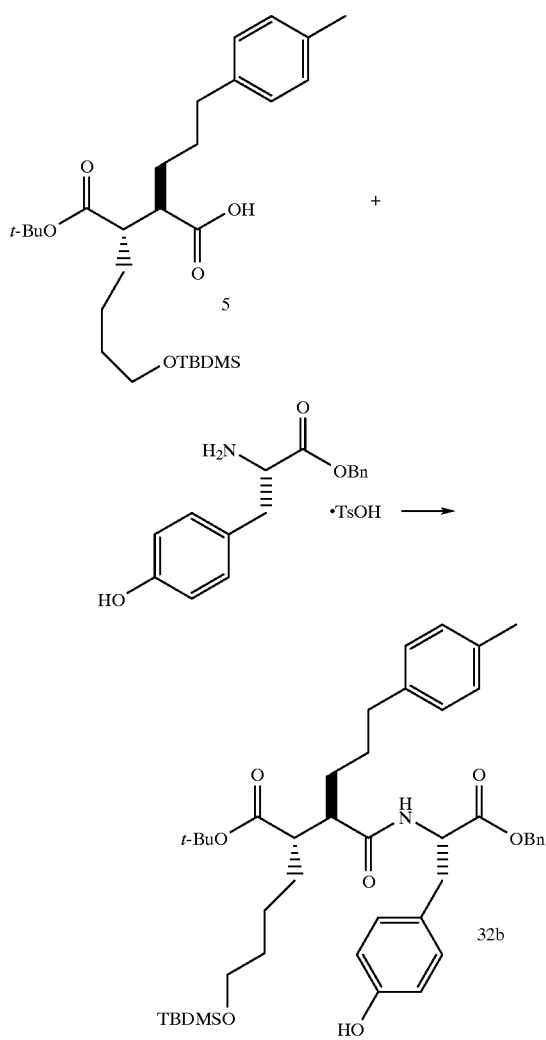

The desired compound was prepared according to the method of Example 1A, except substituting succinate ester 5 for succinate ester 1.

EXAMPLE 32B

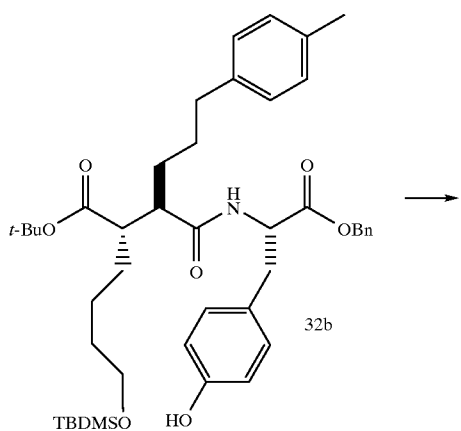

EXAMPLE 32D

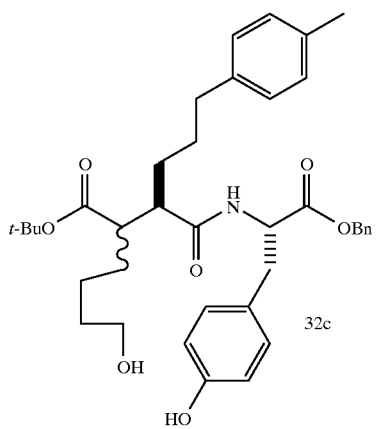

To a 0° C. solution of epimeric amides 32b (1.67 g, 2.24 mmol) in THF (15 mL) was added tetrabutylammonium fluoride (1.0M in THF, 6.5 mL, 6.5 mmol) dropwise via syringe over 5 minutes. After 30 minutes the cooling bath was removed and the reaction mixture was stirred at room temperature for 1.5 hours at which time it was poured into a separatory funnel containing $H_2O$ and ethyl acetate. The aqueous phase was extracted with ethyl acetate and the combined organic layers were dried with $Na_2SO_4$, filtered and concentrated. Flash chromatography (50–80% EtOAc-hexanes) afforded 32c (1.23 g) as an epimeric mixture of diols as a colorless foam.

EXAMPLE 32D

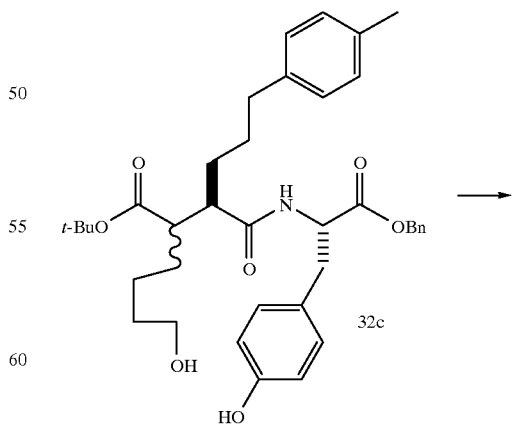

-continued

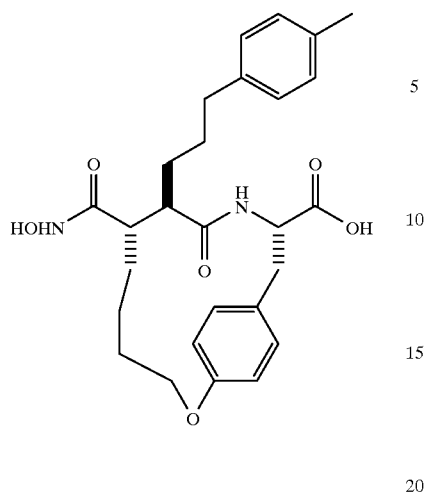

The desired compound was prepared from 32c by ring closure, hydrolysis of the tert-butyl ester, conversion to the hydroxamic acid and debenzylation according to the method of Examples 1C, F, G and D. $^1$H NMR (300 MHz, DMSO-d6) δ −0.4–(−0.51) (m, 1H), 0.52–0.93 (m, 3H), 1.12–1.20 (m, 2H), 1.30–1.42 (m, 1H), 1.44–1.63 (m, 3H), 1.68–1.80 (m, 1H), 1.98–2.08 (m, 1H), 2.22 (s, 3H), 2.31–2.39 (m, 1H), 2.40–2.51 (m, 1H), 2.52–2.63 (m, 1H), 3.24 (dd, 2H, J=4.5, 4.8 Hz), 3.91–4.14 (m, 2H), 4.58–4.7 (m, 1H), 6.89 (d, 2H, J=8.1 Hz), 7.01 (s, 4H), 7.18 (d, 2H, J=8.4 Hz), 7.96 (d, 1H, J=9.9 Hz), 8.70 (bs, 1H), 10.4 (s, 1H). MS (DCI/NH$_3$) m/e 483 (m+H)$^+$. [α] (MeOH)=+24° (MeOH).

EXAMPLE 33

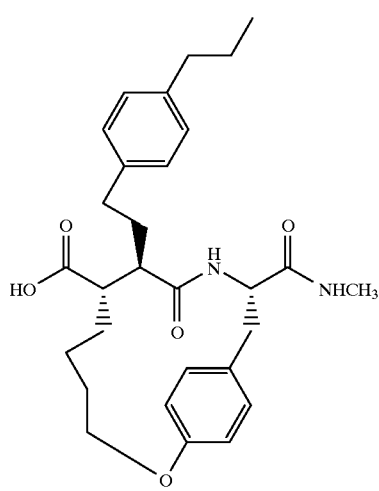

EXAMPLE 33A

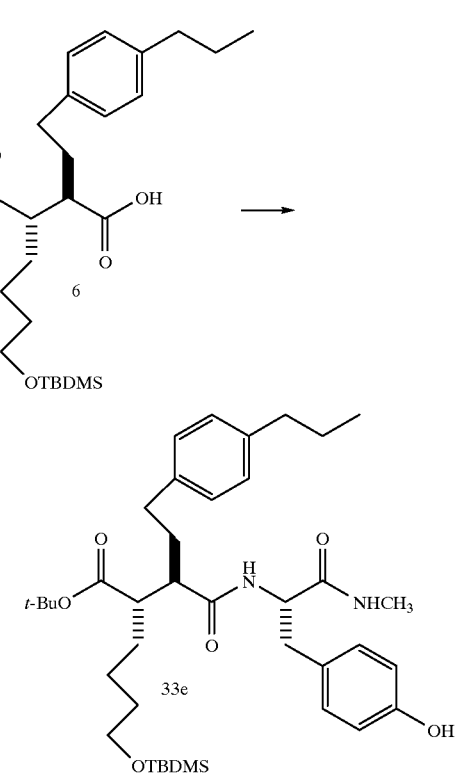

The desired compound was prepared according to the method of Example 1A, except substituting succinate ester 6 for succinate ester 1, and substituting L-tyrosine N-methylamide hydrochloride for benzyltyrosine tosylate salt.

EXAMPLE 33B

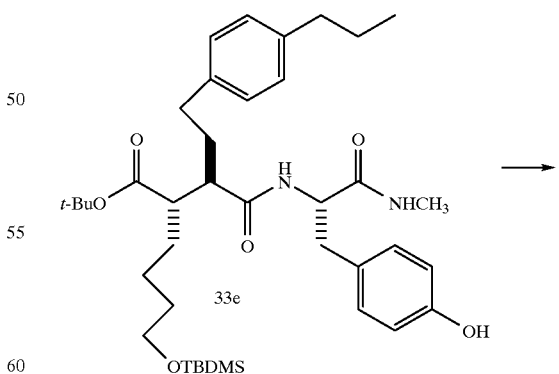

89

-continued

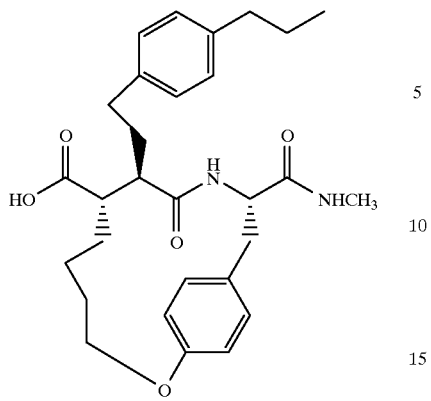

The desired compound was prepared from 33e by desilylation according to the method of Example 32D, followed by ring closure and saponification of the tert-butyl ester according to the method of Examples 1C and F. mp 193–195° C. $^1$H NMR (DMSO-d6) δ −0.30–(−0.17) (complex, 1H), 0.61–0.78 (complex, 1H), 0.79–0.98 (complex, 2H), 0.96 (t, 3H, J=7.4 Hz), 1.30–1.66 (complex, 6H), 1.96–2.17 (complex, 2H), 2.37 (m, 2H), 2.44–2.60 (complex, 3H), 2.64 (d, 3H, J=5.1 Hz), 3.10 (m, 1H), 4.05 (m, 2H), 4.66 (m, 1H), 6.89–6.96 (complex, 4H), 7.05 (d, 2H, J=8.4 Hz), 7.20 (m, 2H), 7.89 (m, 1H), 8.02 (d, 1H, J=9.6 Hz), 12.07 (s, 1H). MS (ESI+) 495 (M+H), 464, 436. Anal calcd for $C_{29}H_{38}N_2O_5 \cdot 0.75 H_2O$: C, 68.54; H, 7.83; N, 5.51. Found: C, 68.63; H, 7.73; N, 5.40.

EXAMPLE 34

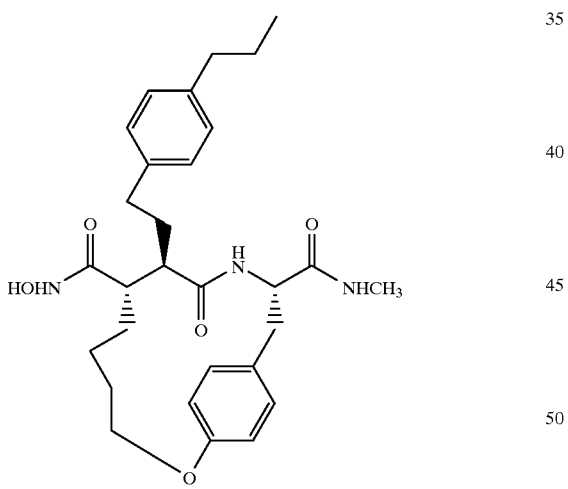

The desired compound was prepared from the product of Example 33 according to the method of Example 1G. mp>260° C. $^1$H NMR (DMSO-d6) δ −0.30–(0.17) (complex, 1H), 0.61–0.95 (complex, 3H), 0.86 (t, 3H, J=7.5 Hz), 1.28–1.40 (complex, 2H), 1.47–1.63 (complex, 4H), 1.73–1.85 (m, 1H), 2.06–2.16 (complex, 1H), 2.26–2.40 (complex, 2H), 2.24–2.59 (complex, 3H), 2.63 (d, 3H, J=4.7 Hz), 3.09 (m, 1H), 3.91–4.18 (m, 2H), 4.62 (m, 1H), 6.89–6.96 (m, 4H), 7.05 (d, 2H, J=8.1 Hz), 7.18–7.24 (complex, 2H), 7.88 (m, 1H), 8.01 (d, 1H, J=9.1 Hz), 8.66 (s, 1H), 10.33 (s, 1H). MS (ESI+) m/e 510 (M+H)$^+$, 477. Anal calcd for $C_{29}H_{39}N_3O_5$: C, 68.34; H, 7.71; N, 8.24. Found: C, 68.06; H, 7.41; N, 8.14.

90

EXAMPLE 35

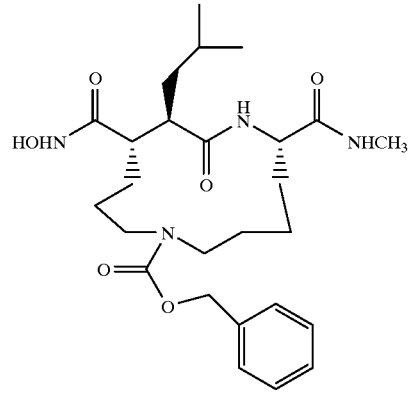

EXAMPLE 35A

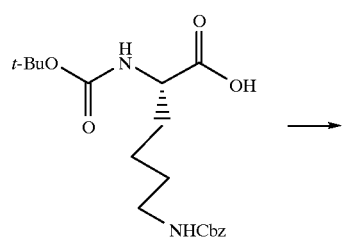

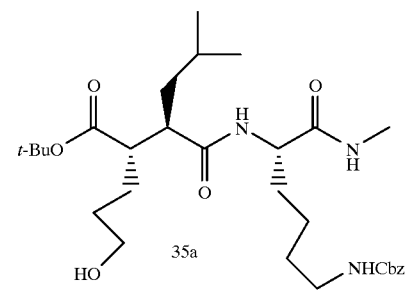

The desired compound was prepared according to the method of Examples 8A, C and D except substituting N-α-t-BOC-N-ε-Cbz-L-lysine for BOC-L-tyrosine in Example 8A and substituting succinate ester 2 for 8b.

EXAMPLE 35B

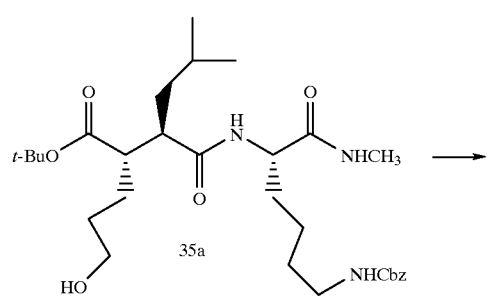

-continued

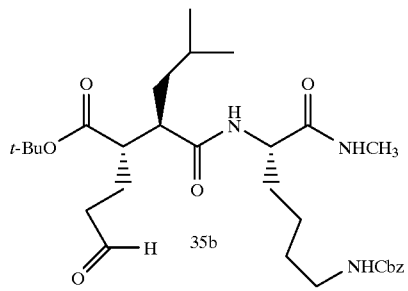

To a −78° C. solution of oxalyl chloride (154 ul, 224 mg, 1.765 mmol) in anhydrous CH₂Cl₂ (3 mL) was added a solution of anhydrous DMSO (251 ul, 276 mg, 3.54 mmol) in anhydrous CH₂Cl₂ (3 mL) dropwise. The suspension was stirred for 1 hour at −70° C. and a solution of 35a (500 mg, 0.887 mmol) in anhydrous CH₂Cl₂ (3 mL) was added dropwise. The reaction mixture was stirred for 6 hours at −70° C. and triethylamine (390 ul, 283 mg, 2.80 mmol) was added and the resulting yellow solution was stirred for 1 hour at ambient temperature. The reaction mixture was diluted with saturated aqueous NH₄Cl and CH₂Cl₂. The aqueous phase was washed with 10% isopropanol-CHCl₃. the combined organic layers were dried over MgSO₄ and filtered and the filtrate was concentrated leaving a yellow gum which was purified using flash chromatography (3% methanol-CH₂Cl₂) to give 35b (411 mg) as a foamy white solid (82% yield).

EXAMPLE 35C

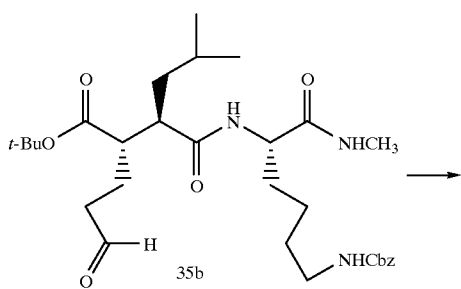

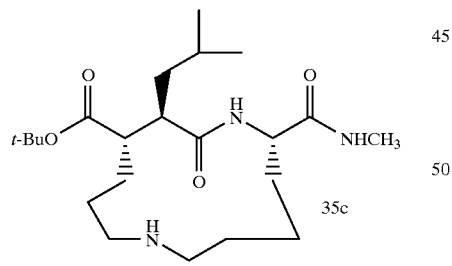

The desired compound was prepared by catalytic hydrogenation of 35b (methanol, palladium hydroxide on carbon, 1 atm. H₂) for 3 days.

EXAMPLE 35D

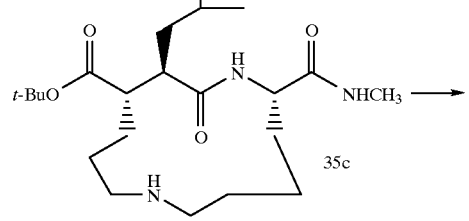

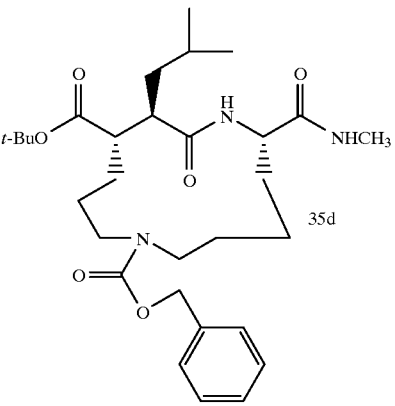

The desired compound was prepared according to the method of Example 18, except substituting 35c for the compound of Example 17.

EXAMPLE 35E

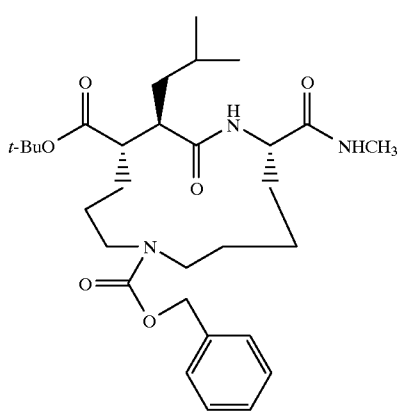

93

-continued

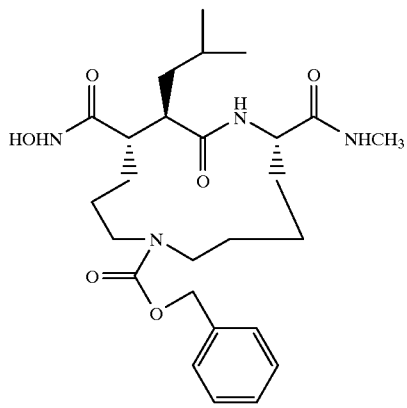

The desired compound was prepared according to the method of Examples 1F and G, except substituting 35d for 8e. $^{1}$H NMR (300 MHz, DMSO-d6) δ 10.55 (s, 1H), 8.80 (s, 1H), 8.31 (d, 1H, J=12 Hz), 7.65 (d, 1H, J=12 Hz), 7.24–7.39 (c, 5H), 4.91–5.04 (c, 2H), 4.20–4.30 (c, 1H), 2.99–3.35 (c, 5H), 2.76–2.85 (c, 1H), 2.73 (d, 3H, J=3 Hz), 1.94–2.04 (c, 1H), 1.06–1.72 (c, 12H), 0.72–0.95 (c, 6H). $^{13}$C NMR (DMSO-d6): 173.1, 172.0, 169.7, 155.1, 136.2, 127.7, 127.0, 126.7, 65.4, 49.9, 49.4, 48.8, 48.7, 45.0. 28.8, 28.5, 27.1, 26.8, 26.6, 24.71, 24.70, 23.4, 22.1, 20.9. MS (ESI) m/e 527(M+Na), 522(M+NH$_4$), 505(M+H). IR (KBr) 3420, 2940, 1630, 1540 cm$^{-1}$. HRMS (ESI) Theory: 505.3026. Found: 505.3023.

EXAMPLE 36

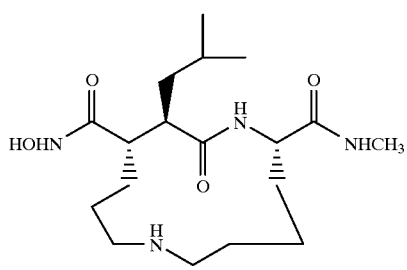

The desired compound was prepared according to the method of Example 19, except substituting the compound of Example 35 for the compound of Example 18.

94

EXAMPLE 37

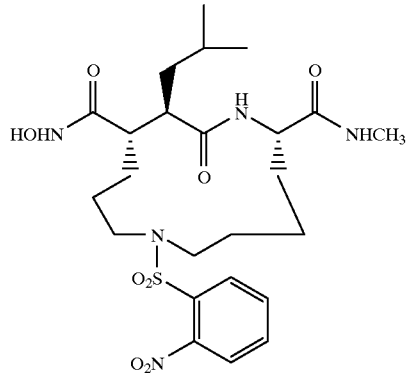

EXAMPLE 37A

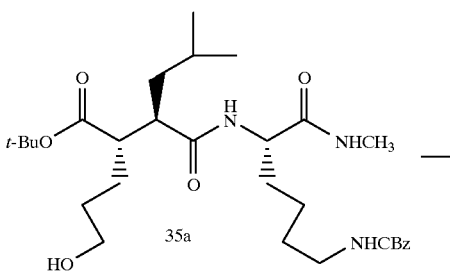

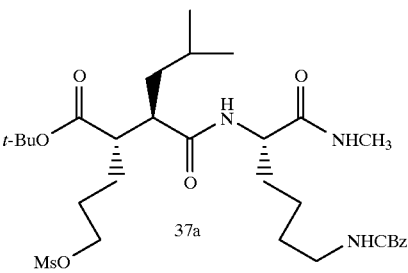

To a 0° C. solution in dichloromethane (18 mL) of 35a (1.0 g, 1.77 mmol) was added triethylamine (697 μl, 506 mg, 5.0 mmol) followed by the dropwise addition of methanesulfonyl chloride (310 μl, 458 mg, 4.0 mmol). The reaction mixture was stirred at 0° C. for 30 minutes and then at ambient temperature for 2 hours. The reaction mixture was diluted with CH$_2$Cl$_2$ and water The aqueous phase was washed once with CH$_2$Cl$_2$. The combined organic layers were dried over MgSO$_4$, filtered and concentrated in vacuo to give 37a as a yellow gum (1.13 g) which was used without further purification.

EXAMPLE 37B

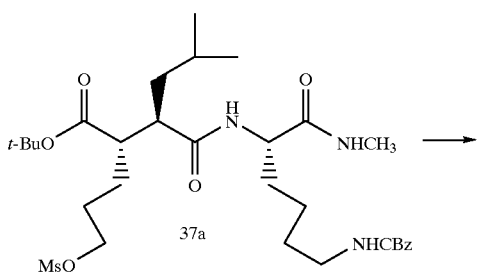

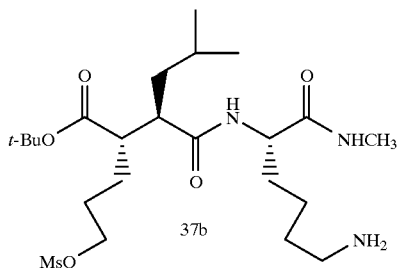

The desired compound was prepared by hydrogenation of 37a (methanol, 10% palladium on carbon, 1 atm $H_2$) for 3 days.

EXAMPLE 37C

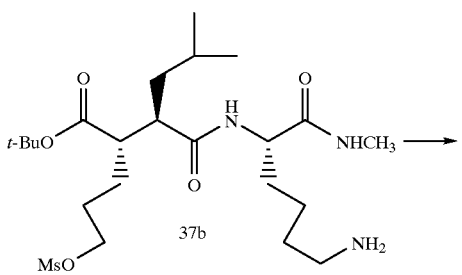

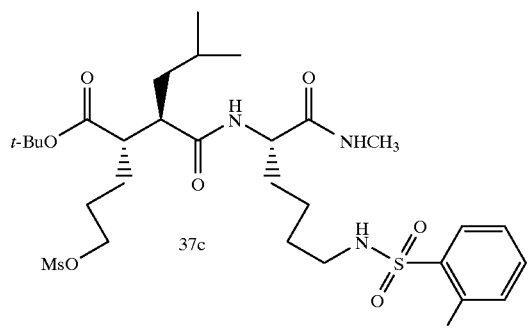

To a solution of 37b (732 mg, 1.44 mmol) in dichloromethane (40 mL) was added uiethylamine (418 μL, 304 mg, 3.0 mmol) and a solution of 2-nitrobenzenesulfonyl chloride (335 mg, 1.5 mmol) in dichloromethane (8 mL) was added dropwise and stirring at was continued for 3 hours. The reaction solution was washed with water, saturated $NaHCO_3$ and brine. The organic layer was dried over $Na_2SO_4$, filtered and the filtrate concentrated to give a green-brown solid which was purified using flash chromatography (3% MeOH-dichloromethane) to give 37c as a white solid (591 mg, 59% yield).

EXAMPLE 37D

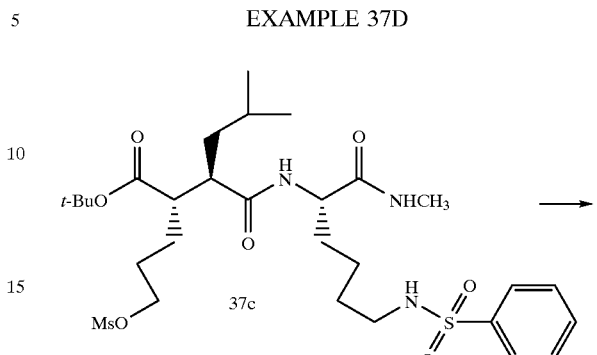

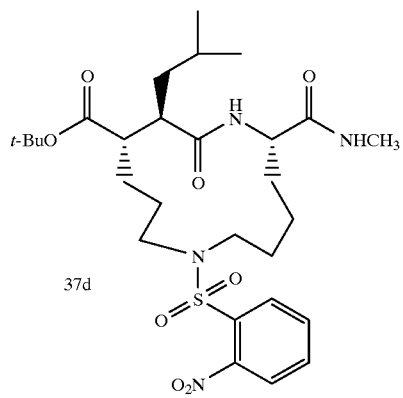

Compound 27 (590 mg, 0.85 mmol) was dissolved in anhydrous DMF (45 ml) and to that solution was added $K_2CO_3$ (235 mg, 1.7 mmol) as a solid and the suspension stirred at RT over 3 days. The reaction mixture was diluted with 40 ml water and extracted 1×400 ml with ether. The organic layer was dried over $MgSO_4$, filtered and the filtrate concentrated to a yellow solid which was purified using flash chromatography eluting with 30% EtOAc/$CH_2Cl_2$ to give a white solid (166 mg, 33% yield).

EXAMPLE 37E

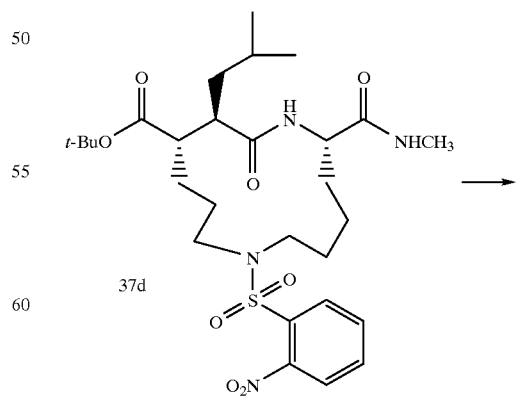

EXAMPLE 38A

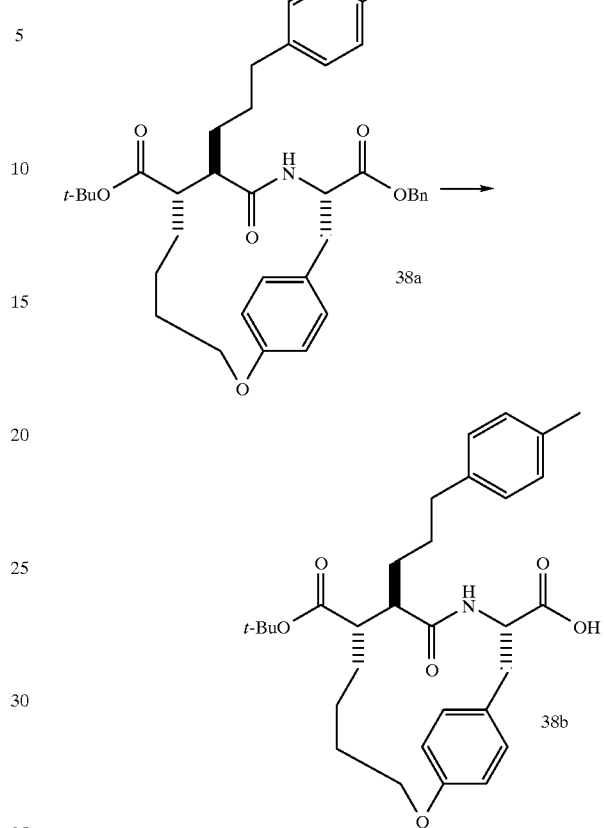

The desired compound was prepared according to the method of Examples 1F and G, except substituting 37d for 1f. $^1$H NMR (300 MHz, DMSO-d6) δ 10.46(d, 1H, J=1.5 Hz), 8.78 (d, 1H, J=1.5 Hz), 8.29 (bd, 1H, J=9 Hz), 7.77–7.97 (c, 4H), 7.45–7.54 (c, 1H), 4.20–4.33 (c, 1H), 2.93–3.16 (c, 2H), 2.61–2.85(c, 2H), 2.56 (d, 3H, J=4.5 Hz), 1.97–2.07 (c, 1H), 1.21–1.81 (c, 13H), 0.81–0.94 (c, 4H), 0.78 (d, 3H, J=6 Hz). MS (APCI) m/e 573 (M+NH$_4$)$^+$, 556 (M+H)$^+$.

To a methanol solution (150 mL) of 38a (3.39 g, 5.52 mmol), prepared by ring closure of 32c using the method of Example 1C, was added dry 10% Pd/C (340 mg) and the mixture was stirred under 4 atm of hydrogen in a pressurized reaction vessel for 2 hours at room temperature. The mixture was filtered through a Celite pad with methanol washings. The filtrate was concentrated to provide 38b (2.83 g) as a white foam.

Example 38B

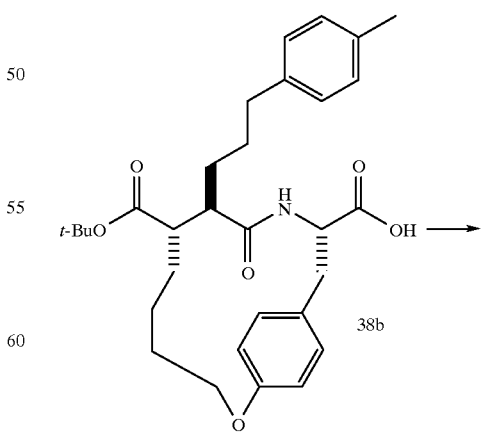

EXAMPLE 38

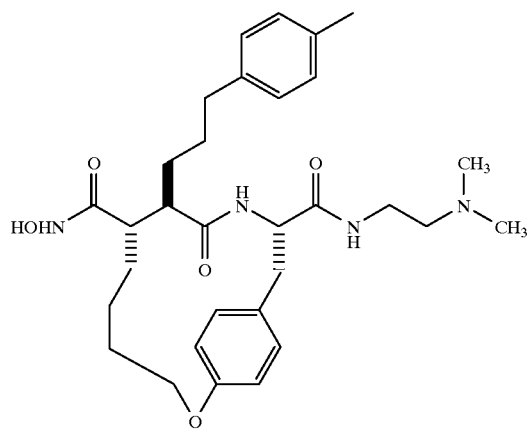

-continued

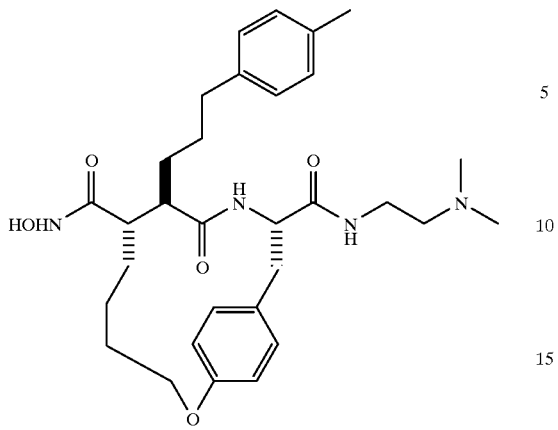

The desired compound was prepared according to the method of Examples 1E, F and G, except substituting 38b for 1f and substituting N,N-dimethylethylenediamine for 4-(2-aminoethyl)benzenesulphonamide. mp>250° C. $^1$H NMR (DMSO) δ-0.4-(-0.46) (m, 1H), 0.52-0.97 (m, 3H), 1.08-1.20 (m, 2H), 1.31-1.40 (m, 2H), 1.52-1.61 (m, 2H), 1.68-1.75 (m, 1H), 2.0-2.08 (m, 1H), 2.12 (s, 6H), 2.23 (s, 3H), 2.24-2.45 (m, 2H), 2.52-2.61 (m, 1H), 3.03-3.20 (m, 3H), 3.3-3.39 (m, 2H), 3.90-4.10 (m, 2H), 4.52-4.64 (m, 1H), 6.90 (d, 2H, J=8.4 Hz), 6.98-7.04 (m, 4H), 7.17-7.22 (m, 2H), 7.63-7.66 (m, 1H), 7.95 (d, 1H, J=9.3 Hz), 8.69 (s, 1H), 10.34 (s, 1H). MS (ESI) m/e 553 (M+H). Anal calcd for $C_{31}H_{44}N_4O_5 \cdot 0.75H_2O$: C, 65.75; H, 8.09; N, 9.89. Found: C, 65.72; H, 8.28; N, 9.80. [α]+28° (c 1.04, MeOH).

EXAMPLE 39

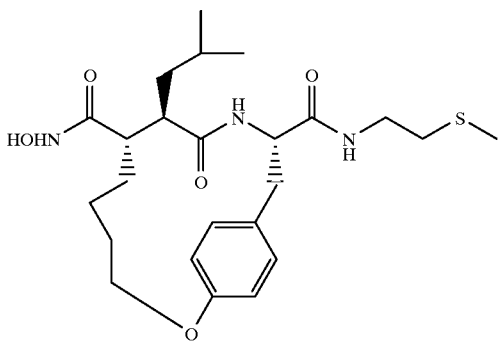

The desired compound was prepared according to the method of Examples 1E-G, except substituting 2-(methylthio)ethylamine for 4-(2-aminoethyl) benzenesulphonamide. mp>270° C. $^1$H NMR (DMSO) δ -0.6-(-0.4) (m, 1H), 0.5-1.0 (m, 5H), 0.71 (d, 3H, J=6.6 Hz), 0.80 (d, 3H, J=6.6 Hz), 1.1-1.4 (m, 2H), 1.5-1.7 (m, 3H), 2.0-2.1 (m, 1H), 2.07 (s, 3H), 2.5-2.7 (m, 3H), 3.05-3.4 (m, 2H), 3.9-4.1 (m, 2H), 4.55-4.7 (m, 1H), 6.90 (d, 8.4H), 7.23-7.3 (m, 2H), 7.8-7.9 (m, 2H), 8.68 (d, 1H, J=1.5 Hz), 10.3 (d, 1H, J=1.5 Hz). $^{13}$C NMR (DMSO) δ 14.5, 21.6, 24.2, 24.7, 24.9, 28.0, 28.4, 32.8, 37.8, 40.3, 40.8, 46.0, 46.6, 53.5, 72.9, 121.0, 121.2, 128.7, 132.0, 132.4, 157.1, 170.0, 171.1, 172.7. MS (DCI/NH$_3$) m/e 480 (M+H)$^+$. Anal calcd for $C_{24}H_{37}N_3O_5S \cdot 0.5H_2O$: C, 58.99; H, 7.84; N, 8.60. Found: C, 59.05; H, 7.65; N, 8.45. [α]+41° (c 0.5, MeOH).

EXAMPLE 40

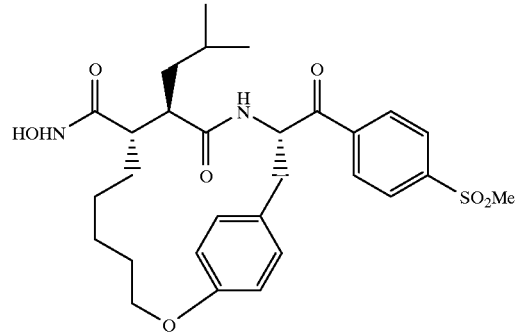

EXAMPLE 40A

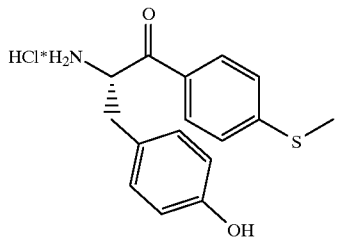

To a 0° C. solution of nBuLi (2.5M/hexanes, 14.2 mL) in diethyl ether (50 mL) was added 4-bromothioanisole (7.2 g, 35.6 mmol) over a few minutes. The resulting solution was allowed to stir cold for 25 minutes and then was added to a -78° C. solution of N-BOC-tBu(OH) tyrosine (3 g, 8.9 mmol) in diethyl ether (200 mL). The solution was stirred at -78° C. for 25 minutes, warmed to 0° over 1 hour and quenched with an aqueous solution of NH$_4$Cl. The aqueous layer was extracted twice with diether ether and the combined organics were washed with brine, dried (Na$_2$SO$_4$), filtered and concentrated in vacuo. Flash chromatography (8:1 hexane-ethyl acetate) gave 2.5 g of product which was immediately taken up in 10 mL 4N HCl-dioxane and stirred for 30 minutes. The resulting slurry was diluted with diethyl ether, filtered and dried for 16 hours under high vacuum, to give 40a (1.4 g) as a chalky-white solid.

EXAMPLE 40B

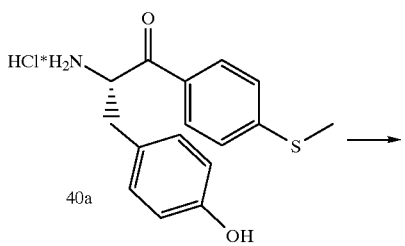

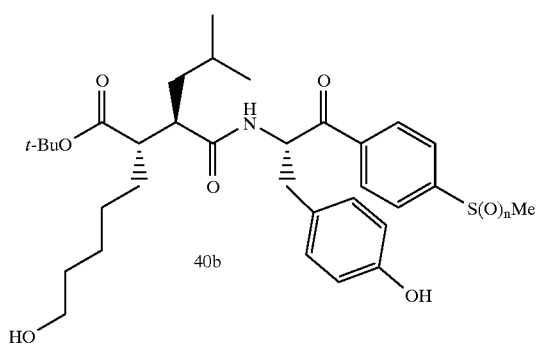

The desired compound was prepared as a mixture of the sulfide (n=0) and sulfone (n=2) using the procedure of Examples 1A and B, except substituting 40a for benzyltyrosine tosylate salt.

EXAMPLE 40C

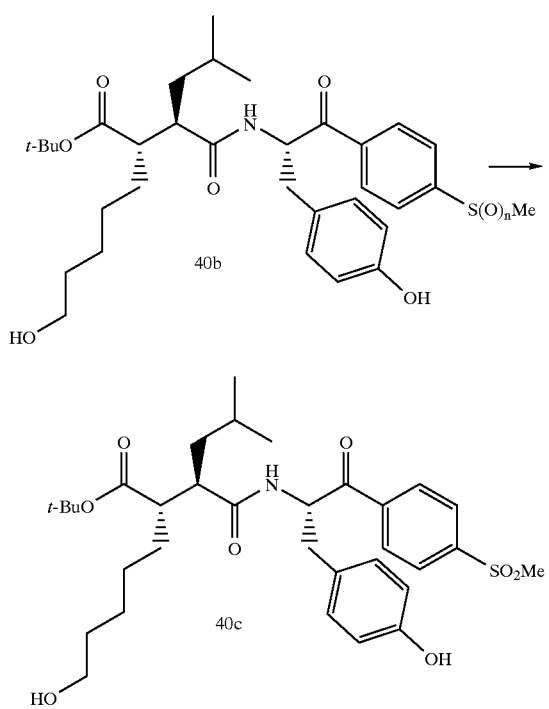

To a solution of 40b (1.0 g, 1.7 mmol) in acetone (50 mL) was added OXONE™ (potassium peroxymonosulfate, 5 g, 8 mmol). The resulting slurry was stirred for 3 days. The reaction was diluted with ethyl acetate and water and the aqueous layer was extracted twice with ethyl acetate. The combined organics were washed with brine, dried ($Na_2SO_4$), filtered and concentrated in vacuo. Flash chromatography (2–4% methanol-methylene chlorid) gave 40c (0.9 g) as a white foam.

EXAMPLE 40D

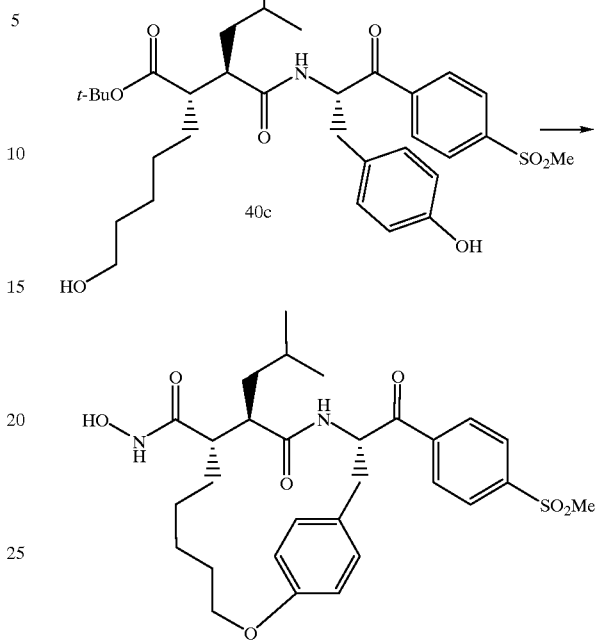

The desired compound was prepared according to the method of Examples 1C, F and G, except substituting 40c for 1c. mp 250–250° C. (dec.). $^1$H NMR (DMSO-d$_6$) δ 10.28 (s, 1H), 8.65 (s, 1H), 8.28–8.25 (d, 2H, J=6.8 Hz), 8.19–8.16 (d, 1H, J=9.5 Hz), 8.07–8.04 (d, 2H, J=6.8 Hz), 7.42–7.39 (d, 1H, J=8.5 Hz), 7.24–7.20 (d, 1H, J=8.5 Hz), 6.97–6.93 (d, 1H, J=8.1 Hz), 6.87–6.83 (d, 1H, J=8.2 Hz), 5.60–5.47 (m, 1H), 4.21–4.13 (m, 2H), 3.12 (s, 3H), 3.12–3.06 (m, 1H), 2.81–2.73 (m, 1H), 2.15–2.12 (m, 1H), 1.70–1.69 (m, 1H), 1.47–1.40 (m, 1H), 1.33–1.30 (m, 1H), 1.15–0.99 (m, 4H), 0.71–0.68 (m, 3H), 0.50–0.38 (m, 7H), (−)0.002–(−)0.09 (m, 1H). Anal calcd for $C_{29}H_{38}N_2O_7S \cdot 0.5H_2O$: C, 61.35; H, 6.92; N, 4.93. Found: C, 61.26; H, 6.83; N, 4.61. $[\alpha]_D$:+11.4°(c=0.21, DMF).

EXAMPLE 41

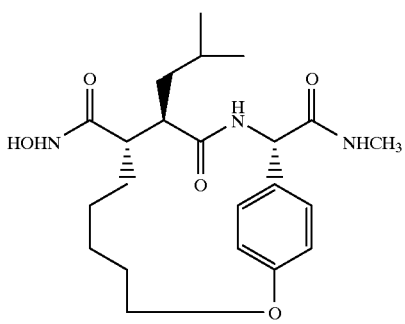

EXAMPLE 41A

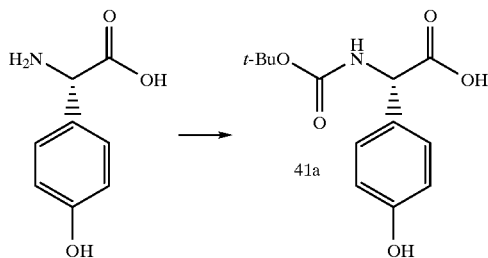

To a solution of (L)-p-hydroxyphenylglycine (5 g, 29.9 mmol, Sigma) in 50% aqueous dioxane (100 mL) and triethylamine (8.3 mL, 59.8 mmol) at ambient temperature was added a solution of Boc-anhydride (13.7 g, 59.8 mmol) in dioxane (10 mL) over 1 minute. The resulting solution was stirred at ambient temperature for 2.5 days and then was poured into a mixture of aqueous 1M HCl (100 mL) and ether (75 mL). The aqueous layer was extracted twice with ether and the combined organic layers were washed with aqueous 1M HCl and brine, dried with MgSO4, filtered and concentrated to afford 41a (10.8 g) as a white foam which was used without further purification.

EXAMPLE 41B

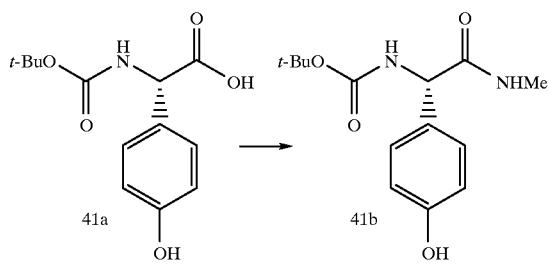

The desired compound was prepared according to the method of Example 1E, except substituting methylamine hydrochloride for 4-(2-aminoethyl)benzenesulphonamide.

EXAMPLE 41C

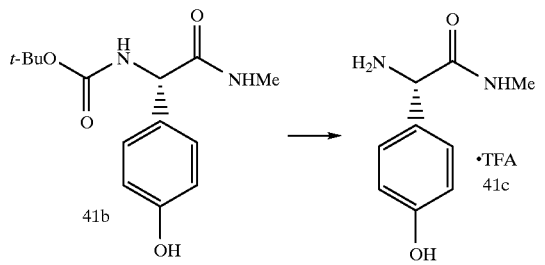

A mixture of 41b (1.13 g, 4.02 mmol), trifluoroacetic acid (10 mL) and $CH_2Cl_2$ (2 mL) was stirred at ambient temperature for 1 hour and then concentrated under a stream of nitrogen. The residue was dissolved in a 1:1 mix of $CH_2Cl_2$ and methanol (40 mL) and concentrated in vacuo. The dissolving-concentration sequence was repeated until a white foam formed to give 41c (1.2 g) which was used without purification.

EXAMPLE 41D

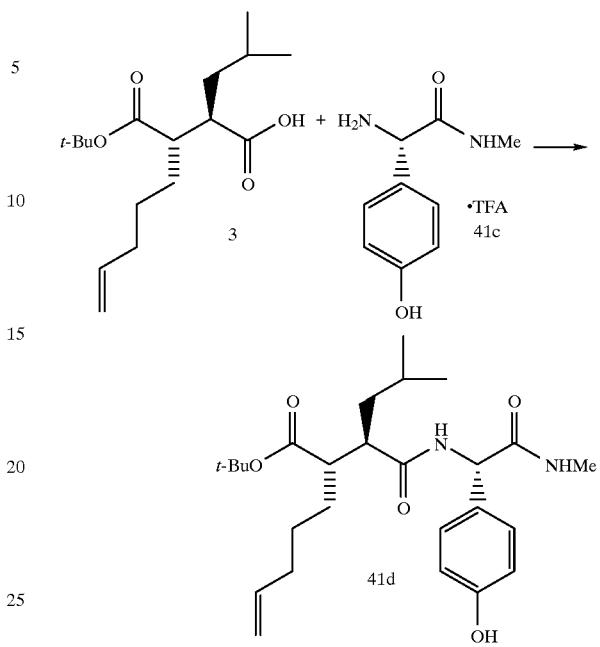

The desired compound was prepared according to the method of Example 1A, except substituting succinate ester 3 for succintate ester 1, and substituting 41c for benzyltyrosine tosylate salt.

EXAMPLE 41E

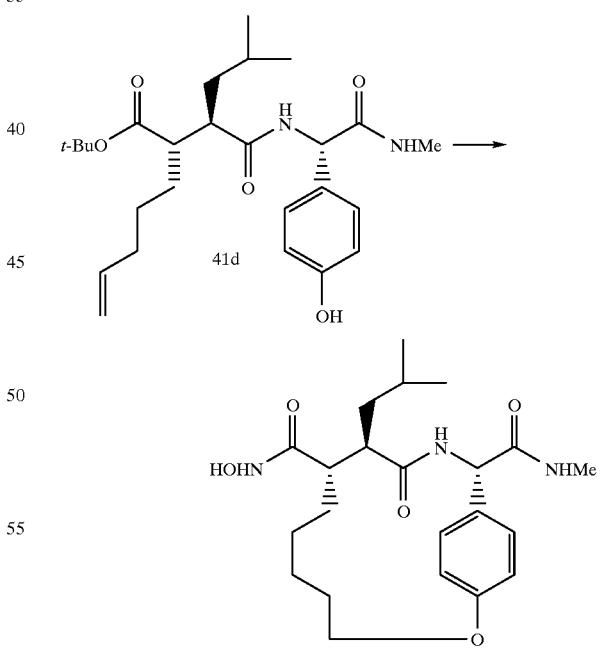

The desired compound was prepared according to the method of Examples 1B, C, F and G, except substituting 41d for 1b. mp>270° C. $^1$H NMR (DMSO) δ −0.65–(−0.5) (m, 1H), 0.4–1.1 (m, 6H), 0.77 (apparent t, 6H, J=6.6 Hz), 1.2–1.5 (m, 4H), 1.6–1.7 (m, 1H), 2.3–2.5 (m, 1H), 2.65 (d, 3H, J=4.5 Hz), 4.1–4.2 (m, 2H), 5.30 (d, 1H, J=9.3 Hz), 6.87

(dd, 1H, J=8.1, 2.4 Hz), 6.96 (dd, 1H, J=8.1, 2.4 Hz), 7.24 (dd, 1H, J=8.1, 2.4 Hz), 7.38 (dd, 1H, J=8.1, 2.4 Hz), 8.0–8.1 (m, 1H), 8.19 (d, 1H, J=9.3 Hz), 8.64 (d, 1H, J=1.2 Hz), 10.24 (d, 1H, J=1.5 Hz). MS (DCI/NH$_3$) m/e 420 (M+H)$^+$. Anal calcd for C$_{22}$H$_{33}$N$_3$O$_5$.0.1H$_2$O: C, 62.72; H, 7.94; N, 9.97. Found: C, 62.61; H, 7.73; N, 9.73. [α]+186° (c 0.25, DMF).

EXAMPLE 42

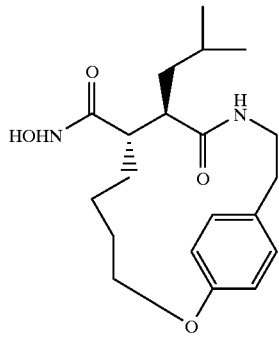

The desired compound was prepared according to the method of Examples 1A–C, F and G, except substituting tyramine for benzyltyrosine tosylate salt. mp>270° C. $^1$H NMR (300 MHz, DMSO-d6) δ −0.5–(−0.4) (m, 1H), 0.5–1.0 (m, 4H), 0.73 (d, 3H, J=6.3 Hz), 0.77 (d, 3H, J=6.3 Hz), 1.1–1.3 (m, 2H), 1.4–1.7 (m, 3H), 1.98 (dd, 1H, J=10.5, 3.3 Hz), 2.5–2.6 (m, 1H), 2.8–3.0 (m, 2H), 3.8–4.1 (m, 3H), 6.85–6.95 (m, 2H), 7.1–7.2 (m, 2H), 7.40 (d, 9.3H), 8.67 (s, 1H), 10.3 (s, 1H). $^{13}$C NMR (DMSO) δ 21.5, 24.1, 24.6, 25.2, 28.1, 28.5, 33.5, 38.3, 40.6, 46.6, 46.7, 72.7, 120.6, 120.9, 129.0, 131.6, 133.3, 156.9, 170.3, 172.6. MS (CI NH3) m/e 363 (M+H)$^+$. Anal calcd for C$_{20}$H$_{30}$N$_2$O$_4$.0.8H$_2$O: C, 63.74; H, 8.45; N, 7.43. Found: C, 63.90; H, 8.53; N, 7.33. [α]+103° (c 0.3, MeOH).

EXAMPLE 43

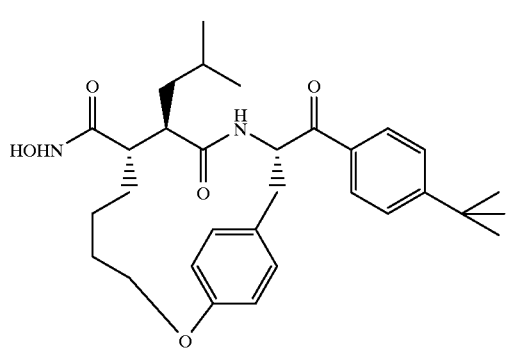

EXAMPLE 43A

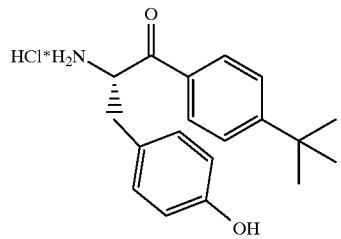

43a

The desired compound was prepared according to the method of Example 40A, except substituting 4-bromo-tert-butyl benzene for 4-bromothioanisole.

EXAMPLE 43B

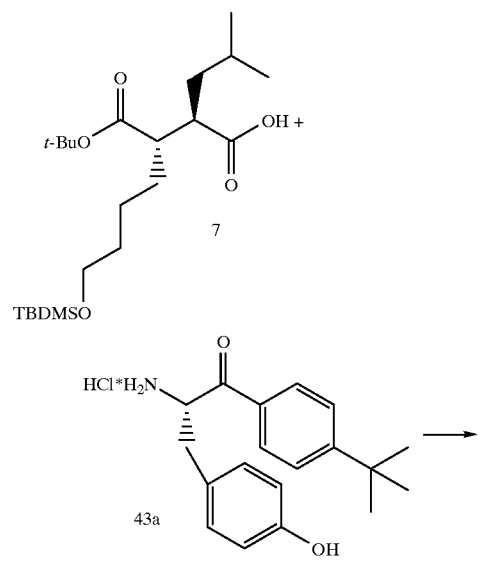

The desired compound is prepared by coupling of 43a and 7, and deprotection using tetrabutylammonium fluoride according to the method of Examples 32B and C.

EXAMPLE 43D

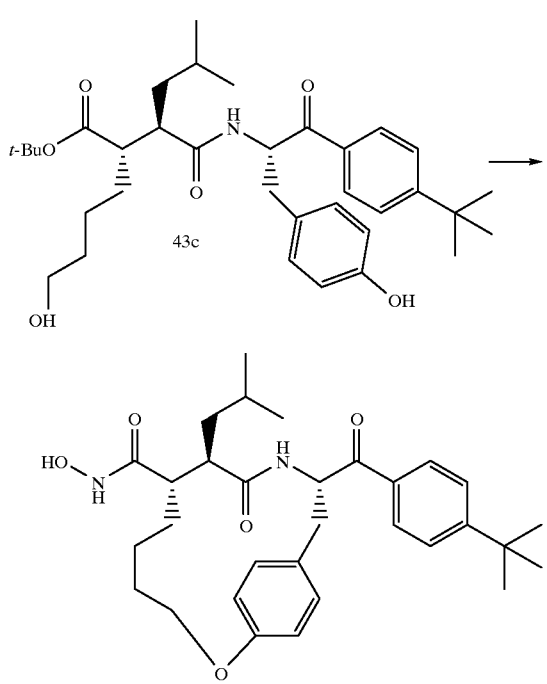

The desired compound was prepared by ring closure according to the method of Example 8E, followed by saponification of the tert-butyl ester and conversion to the hydroxamate according to the method of Examples 1F and G, except substituting 43c for 1c. mp 220–221° C. $^1$H NMR (CD$_3$OD) δ −0.26 (m, 1H), 0.50 (d, 3H, J=5.7 Hz), 0.64 (d, 3H, J=5.8 Hz), 0.85 (m, 4H), 1.18 (m, 3H), 1.35 (s, 9H), 1.63 (m, 1H), 1.79 (m, 2H), 2.89 (t, 1H, J=12.9 Hz), 3.21 (dd, 1H, J=4.7, 12.9 Hz), 4.08 (m, 1H), 4.18 (m, 1H), 5.93 (dd, 1H, J=4.4, 12.2 Hz), 6.90 (dd, 1H, J=2.7, 8.1 Hz), 6.96 (dd, 1H, J=2.7, 8.4 Hz), 7.19 (dd, 1H, J=2.4, 8.1 Hz), 7.41 (dd, 1H, J=1.7, 8.1 Hz), 7.55 (d, 2H, J=8.5 Hz), 8.05 (d, 2H, J=8.4 Hz), 8.38 (d, 1H, J=12.2 Hz). $^{13}$C NMR (CD$_3$OD) δ 21.35, 24.75, 25.99, 29.49, 30.24, 30.67, 31.48, 36.03, 36.83, 42.44, 47.90, 48.45, 55.04, 74.40, 122.14, 122.37, 126.77, 129.80, 130.55, 133.17, 133.23, 134.16, 158.65, 159,01, 173.25, 175.52, 199.27. MS (DCI/NH$_3$) m/e 523 (M+H)$^+$. Anal calcd for C$_{31}$H$_{42}$N$_2$O$_5$.H$_2$O: C, 68.86; H, 8.20; N, 5.18. Found: C, 68.57; H, 8.05; N, 5.45.

EXAMPLE 44

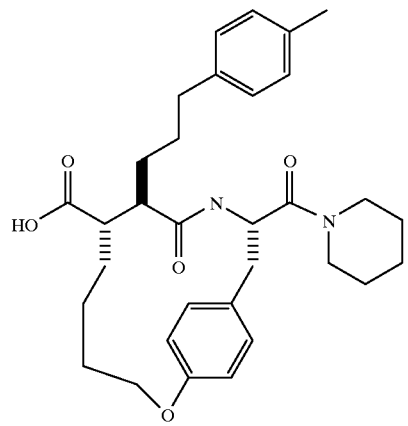

The desired compound was prepared as a white foam according to the method of Examples 1E and F, except substituting piperidine for 4-(2-aminoethyl)benzenesulphonamide, substituting 32a for 1e and substituting methanol for DMF in Example 1E. $^1$H NMR (DMSO) δ −0.40–(−0.24) (m, 1H), 0.52–0.72 (m, 1H), 0.73–1.0 (m, 2H), 1.10–1.43 (m, 7H), 1.44–1.70 (m, 6 H), 1.92–2.08 (m, 2H), 2.22 (s, 3H), 2.24–2.37 (m, 1H), 2.39–2.50 (m, 1H), 2.71–2.93 (m, 2H), 3.32–3.40 (m, 2H), 3.51–3.58 (m, 2H), 4.0–4.08 (m, 2H), 5.0–5.12 (m, 1H), 6.88 (d, 2H, J=8.4 Hz), 6.97 (d, 2H, J=8.1 Hz), 7.03 (d, 2H, J=8.1 Hz), 7.15 (d, 1H, J=9.3 Hz), 7.24 (d, 1H, J=9.2 Hz), 8.13 (d, 1H, J=9.9 Hz). MS (DCI/NH$_3$) 535 (M+H)$^+$.

EXAMPLE 45

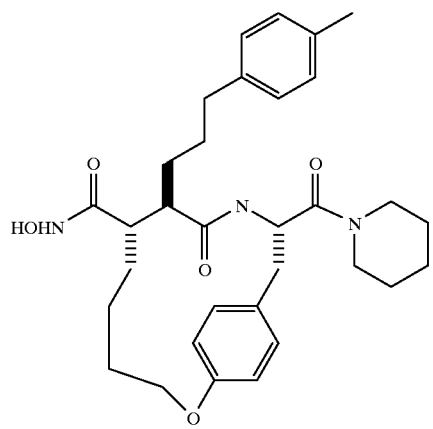

The desired compound was prepared as a white solid according to the method of Example 1G, except substituting the compound of Example 44 for 1a. mp>250° C. $^1$H NMR (DMSO) δ −0.50–(−0.38) (m, 1H), 0.53–1.0 (m, 3H), 1.07–1.20 (m, 2H), 1.22–1.43 (m, 5H), 1.45–1.64 (m, 5H), 1.65–1.81 (m, 1H), 1.98–2.10 (m, 1H), 2.23 (s, 3H), 2.25–2.31 (m, 1H), 2.38–2.45 (m, 1H), 2.71–2.90 (m, 2H), 3.30–3.42 (m, 2H), 3.50–3.62 (m, 2H), 3.94–4.10 (m, 2H), 4.97–5.10 (m, 1H), 6.87 (d, 2H, J=9.0 Hz), 6.93–7.07 (m, 4H), 7.15 (d, 1H, J=7.2 Hz), 7.24 (d, 1H, J=7.1 Hz), 8.05 (d, 1H, J=9.3 Hz), 8.69 (s, 1H), 10.36 (s, 1H). MS (ESI-) m/e 548 (M−1). Anal calcd for $C_{32}H_{43}N_3O_5$: C, 69.91; H, 7.88; N, 7.64. Found: C, 69.85; H, 7.77; N, 7.57. [α]+56° (c=1.0, MeOH).

EXAMPLE 46

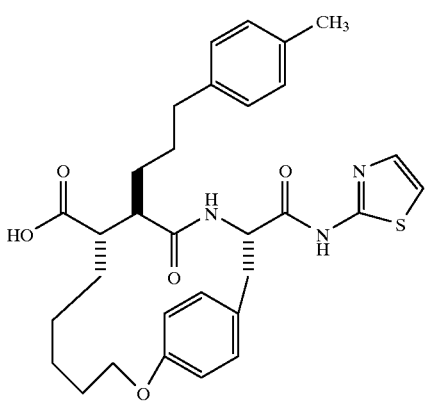

The desired compound was prepared according to the method of Examples 1E and F, except subsituting 38b for 1e, and substituting 2-aminothiazole for 4-(2-aminoethyl) benzenesulphonamide. $^1$H NMR (300 MHz, DMSO-d6) δ −0.34–(−0.20) (m, 1H), 0.60–0.74 (m, 1H), 0.81–0.97 (m, 2H), 1.13–1.25 (m, 2H), 1.36–1.45 (m, 2H), 1.55–1.67 (m, 2H), 1.90–2.01 (m, 1H), 2.05–2.16 (m, 1H), 2.22 (s, 3H), 2.24–2.38 (m, 1H), 2.04–2.45 (m, 1H), 2.57–2.65 (m, 1H), 3.24–3.34 (m, 1H), 3.94–4.05 (m, 1H), 4.07–4.16 (m, 1H), 4.95–5.03 (m, 1H), 6.93–7.04 (m, 7H), 7.20–7.27 (m, 1H), 7.31 (d, 1H, J=3.6 Hz), 7.35–7.38 (m, 1H), 7.53 (d, 1H, J=3.6 Hz), 8.22 (d, 1H, J=9.6 Hz), 12.40 (bs, 1H). MS (DCI/NH$_3$) m/e 550 (M+H)$^+$.

EXAMPLE 47

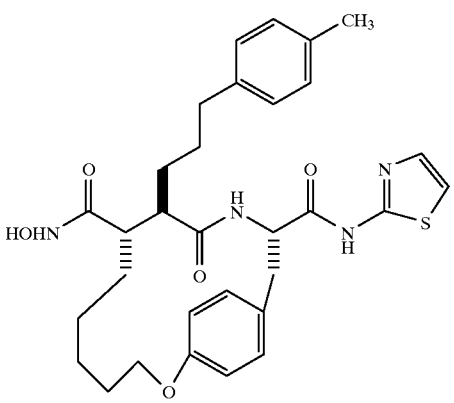

The desired compound was prepared according to the method of Example 1G, except substituting the compound of Example 46 for 1a. mp>250° C. $^1$H NMR (300 MHz, DMSO-d6) δ −0.48–(−0.33) (m, 1H), 0.60–0.93 (cm, 3H), 1.10–1.23 (m, 2H), 1.28–1.50 (m, 2H), 1.52–1.67 (m, 2H), 1.70–1.81 (m, 1H), 2.04–2.18 (m, 1H), 2.21 (s, 3H), 2.23–2.31 (m, 1H), 2.40–2.48 (m, 1H), 2.58–2.67 (m, 1H), 3.23–3.25 (m, 1H), 3.90–4.00 (m, 1H), 4.04–4.16 (m, 1H), 4.88–4.98 (m, 1H), 6.90–7.01 (m, 6H), 7.22–7.28 (m, 1H), 7.29 (d, 1H, J=3.9 Hz), 7.31–7.36 (m, 1H), 7.50 (d, 1H, J=3.3 Hz), 8.12 (d, 1H, J=9.3 Hz), 8.68 (s, 1H), 10.35 (s, 1H), 12.30 (s, 1H). MS (DCI/NH$_3$) m/e 565 (M+H)$^+$. Anal calcd for $C_{30}H_{36}N_4O_5S.0.5H_2O$: C, 62.80; H, 6.50; N, 9.76. Found: C, 62.95; H, 6.33; N, 9.76. [α]+26° (c=0.9, MeOH).

EXAMPLE 48

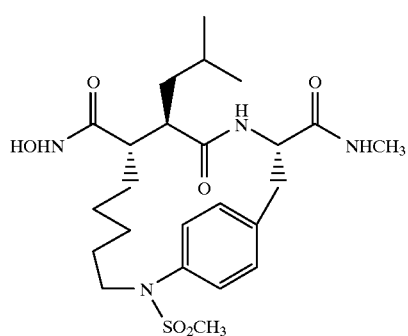

EXAMPLE 48A

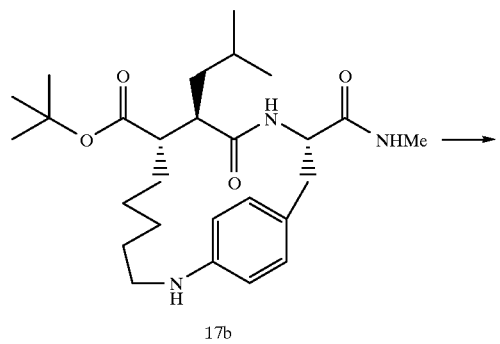

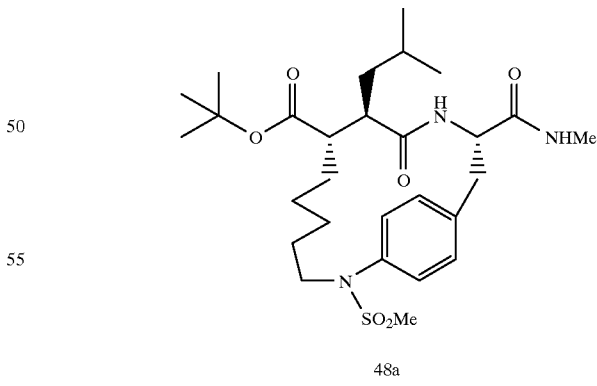

48a

To a solution of 17b (142 mg, 0.300 mmol) in CH$_2$Cl$_2$ (4 mL) was added triethylamine (0.059 mL, 0.420 mmol) followed by methanesulfonyl chloride (0.028 mL, 0.360 mmol). The mixture was left stirring at room temperature for 2 hours and then was poured into brine. The biphasic mixture was extracted with CH$_2$Cl$_2$ (3×) and the combined CH₂Cl₂ layers were dried (MgSO₄), filtered and evaporated to dryness. Flash chromatography (2%–5% MeOH/CH₂Cl₂) (yielded 157.7 mg (95.2%) of 48a as pale yellow crystals.

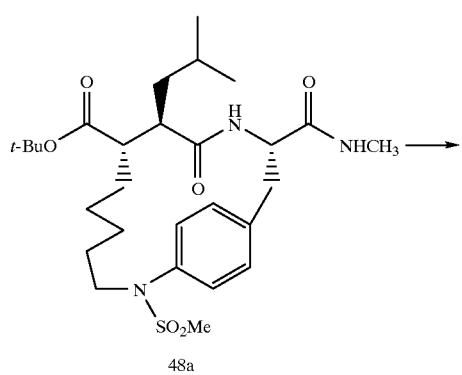

48a

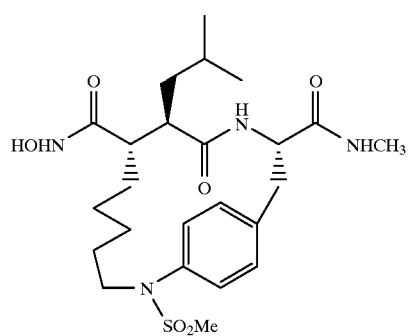

The desired compound was prepared as a white solid according to the method of Examples 1F and G, except substituting 48a for 1f. mp 242–244° C. (dec). $^1$H NMR (DMSO-D6) δ −0.118 (m, 1H), 0.63 (m, 2H), 0.73 (d, 3H, J=6.6 Hz), 0.83 (d, 3H, J=6.6 Hz), 0.79–1.40 (m, 7H), 1.66 (m, 1H), 2.24 (m, 1H), 2.44–2.56 (m, 1H), 2.62 (d, 3H, J=4.5 Hz), 2.50–2.75 (m, 2H), 2.93 (s, 3H), 3.01 (dd, 1H, J=2.7, 12 Hz), 3.60 (m, 2H), 4.52 (m, 1H), 7.17 (dd, 1H, J=8.1, 1.8 Hz) 7.32 (dd, 1H, J=8.1, 1.8 Hz), 7.41 (dd, 1H, J=8.1, 1.8 Hz), 7.38 (dd, 1H, J=8.1, 1.8 Hz), 7.76 (q, 1H, J=4.5 Hz), 7.06 (s, 1H, J=9.3 Hz), 8.70 (s, 1H), 10.30 (s, 1H). MS (ESI) 1043 (M+Na)⁺, 1021 (2M+H)⁺, 533 (M+Na)⁺, 511 (M+H)⁺, 478, 215. Anal calcd for C₂₄H₃₈N₄O₆S.1.75 H₂O: C, 53.16; H, 7.71; N, 10.33. Found: C, 53.14; H, 7.32; N, 9.90. [α]=+14.6° (c=0.205, CH₃OH).

EXAMPLE 49

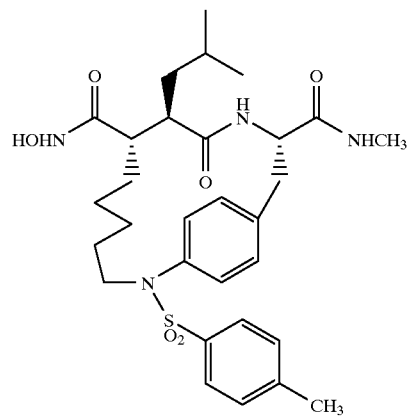

The desired compound was prepared according to the method of Example 48, except substituting p-toluenesulfonyl chloride for methanesulfonyl chloride. mp: 235–237° C. (dec). $^1$H NMR (DMSO-D6) δ −0.16 (m, 3H), 0.72 (d, 3H, J=6.6 Hz), 0.82 (d, 3H, J=6.6 Hz), 0.95–1.26 (m, 7H), 1.64 (m, 1H), 2.22 (m, 1H), 2.61 (d, 3H, J=4.5 Hz), 2.69 (t, 1H, J=13.2 Hz), 2.97 (dd, 1H, J=13.2, 2.4 Hz), 3.36 (m, 1H), 3.51 (m, 1H), 4.47 (m, 1H), 6.82 (dd, 1H, J=1.8, 8.1 Hz), 6.97 (dd, 1H, J=1.8, 8.1 Hz), 7.28 (m, 1H, J=1.2, 8.1 Hz), 7.33–7.447.33–7.44 (m, 5H), 7.72 (q, 1H, J=4.5 Hz), 8.05 (d, 1H, J=8.7 Hz), 8.70 (s, 1H), 10.30 (s, 1H). MS (DCI-NH3) m/e 587 (M+H)⁺, 543, 447, 391, 302, 258, 215. Anal calcd for C₃₀H₄₂N₄O₆S.0.75 MeOH: C, 60.46; H, 7.42; N, 9.17. Found: C, 60.33; H, 7.40; N, 8.90. [α]=+41.5° (c=0.065, CH₃OH).

EXAMPLE 50

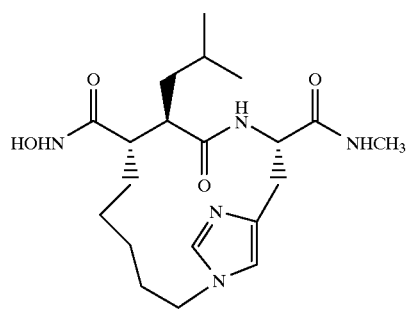

EXAMPLE 50A

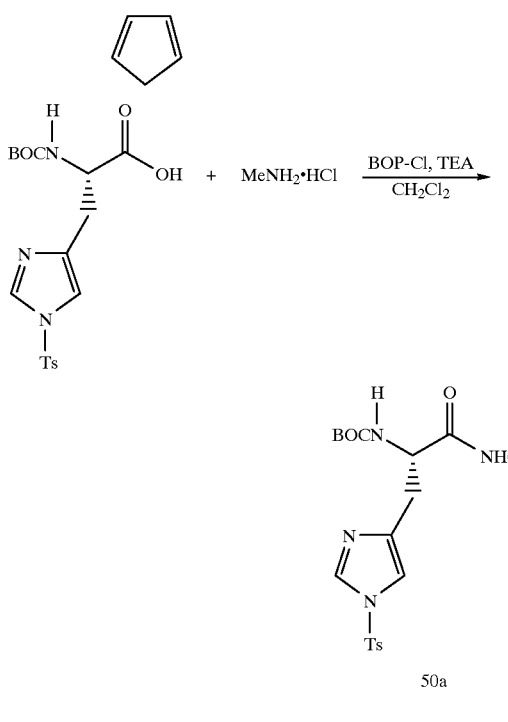

To a 0° C. solution of N-Boc-imidazolyl-tosyl-L-histidine (5.0 g, 12.2 mmol) in dichloromethane (125 ml) was added methylamine hydrochloride (990 mg, 14.7 mmol), BOP-Cl (3.7 g, 14.7 mmol) and TEA (4 ml, 29.4 mmol) under nitrogen, the ice-bath was removed and the mixture was stirred at room temperature for 23 hours. The reaction mixture was diluted with brine and extracted with three portions of dichloromethane, dried over sodium sulfate, filtered and concentrated in vacuo. The crude mixture was purified by flash chromatography(60% ethyl acetate-hexanes, then 10% MeOH/CH$_2$Cl$_2$) to provide 50a (1.67 g, 32%) as a white solid.

EXAMPLE 50B

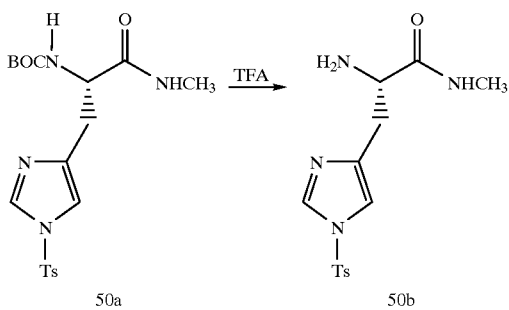

A solution of 50a in trifluoroacetic acid was stirred for 10 minutes. The trifluoroacetic acid was evaporated and the mixture was partitioned between CH$_2$Cl$_2$ and saturated aqueous NaHCO$_3$. The aqueous phase was extracted with three portions of CH$_2$Cl$_2$ and the combined extracts were washed with brine, dried over sodium sulfate and concentrated in vacuo to give 50b (1.09 g, 85%) as an off-white solid.

EXAMPLE 50C

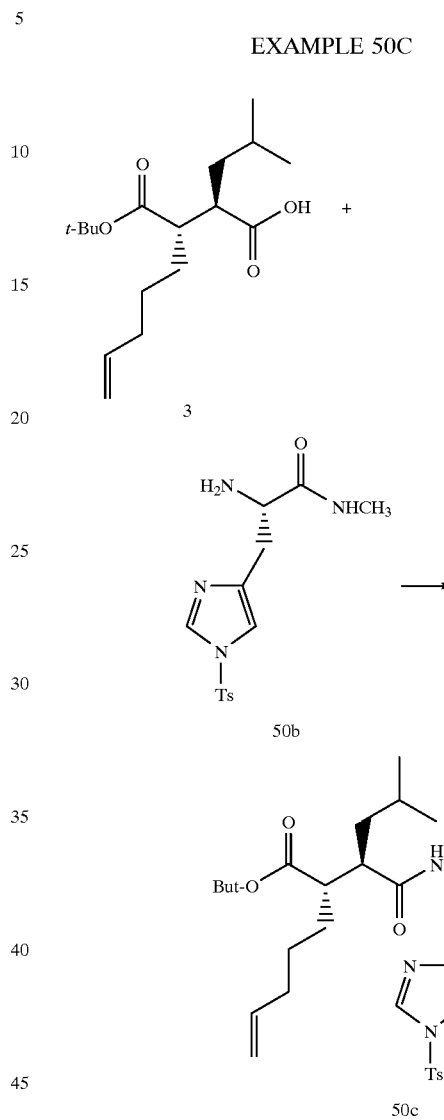

To a 0° C. solution of succinate ester 3 (772 mg, 2.59 mmol) and 50b (1.0 g, 3.1 mmol) in dichloromethane (20 ml) was added BOP-Cl (789 mg, 3.1 mmol) and triethylamine (862 μl, 6.2 mmol) under nitrogen, the ice-bath was removed, and the mixture was stirred at room temperature for 23 hours. Additional 50b, BOP-Cl and triethylamine (0.8 equivalent) were then added and stirring was continued for another 48 hours. The reaction mixture was diluted with brine and extracted with three portions of dichloromethane. The combined organic extracts were dried over sodium sulfate, filtered and concentrated in vacuo. The crude mixture was purified by flash chromatography (5% MeOH—CH$_2$Cl$_2$) and (80% ethyl acetate-hexanes)to provide 50c (1.01 g, 65%) as a yellow foam.

EXAMPLE 50D

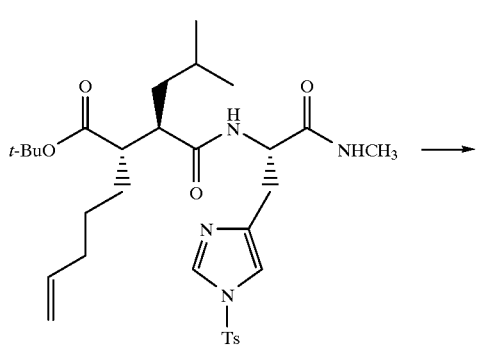

50c

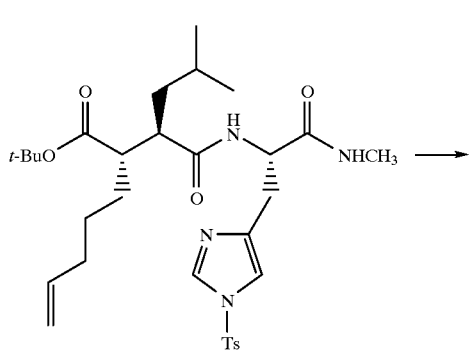

50c

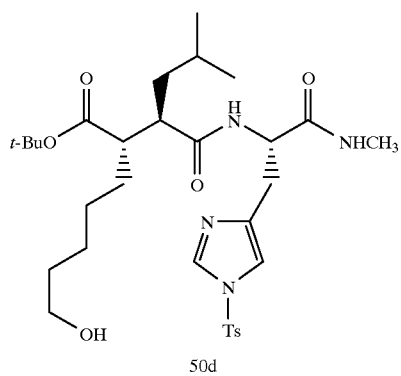

50d

The desired compound was prepared according to the method of Example 1B, except substituting 50c for 1b.

EXAMPLE 50E

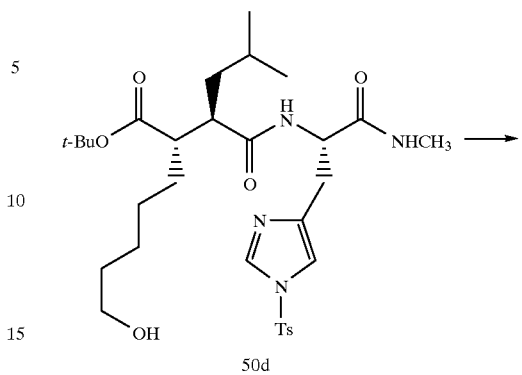

50d

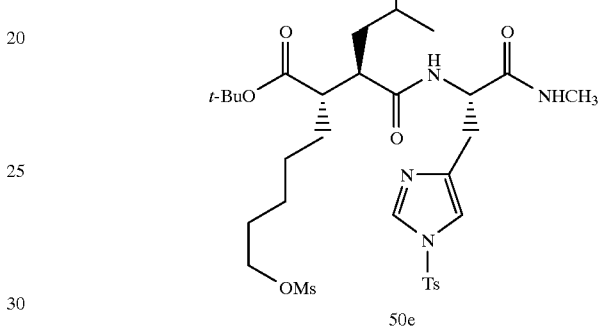

50e

To a 0° C. solution of 50d (156 mg, 0.25 mmol) in CH$_2$Cl$_2$(4 ml) under nitrogen was added methanesulfonyl chloride(25 μl, 0.325 mmol), followed by NMM(41 μl, 0.375 mmol), the resulting mixture was stirred at 0° C. for 2 hr and diluted with CH$_2$Cl$_2$/brine, extracted with two portions of CH$_2$Cl$_2$, dried over sodium sulfate, filtered, solvent was evaporated and the crude mixture was purified by flash chromatography(5% MeOH/CH$_2$Cl$_2$) to afford 50e (113 mg, 65%) as a white foam.

EXAMPLE 50F

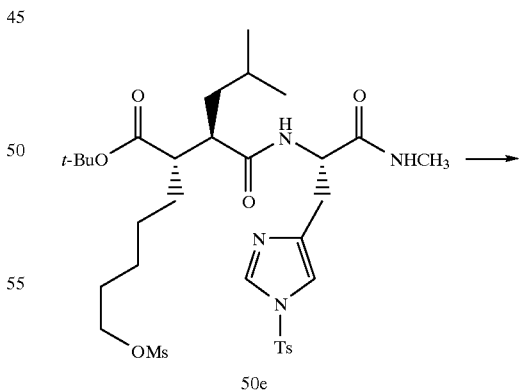

50e

117

-continued

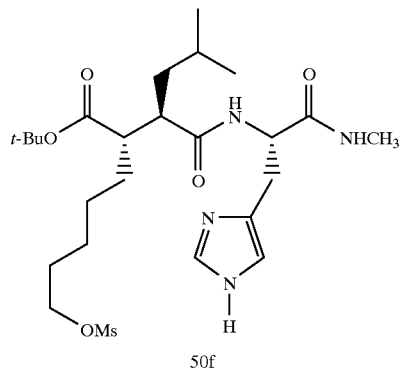

50f

A mixture of 50e (166 mg, 0.24 mmol) and HOBT (64.8 mg, 0.48 mmol) in THF (4 ml) was stirred at room temperature for 24 hours, the solvent was evaporated, and the crude product was purified by flash chromatography (5%–10% MeOH-CH$_2$Cl$_2$) to afford 50f (116 mg, 89%) as a white solid.

EXAMPLE 50G

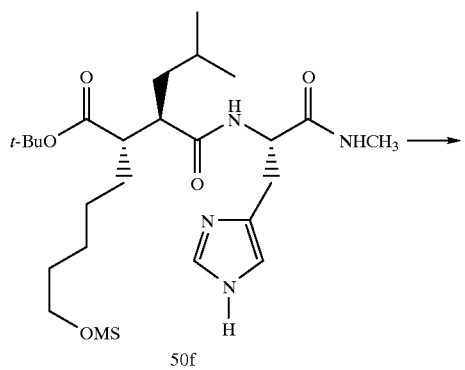

50f

50g

A mixture of 50f (137 mg, 0.25 mmol), LiI (50 mg, 0.375 mmol) and Na$_2$CO$_3$ (27 mg, 0.25 mmol) in acetone(5 ml) was heated at 50° C. for 5 hours. The reaction mixture was then cooled to ambient temperature and stirring was continued for 17 hours. The solvent was evaporated and the crude product was purified by flash chromatography(10% MeOH-CH$_2$Cl$_2$) to afford 50 g (71 mg, 63%) as a white solid.

118

EXAMPLE 50H

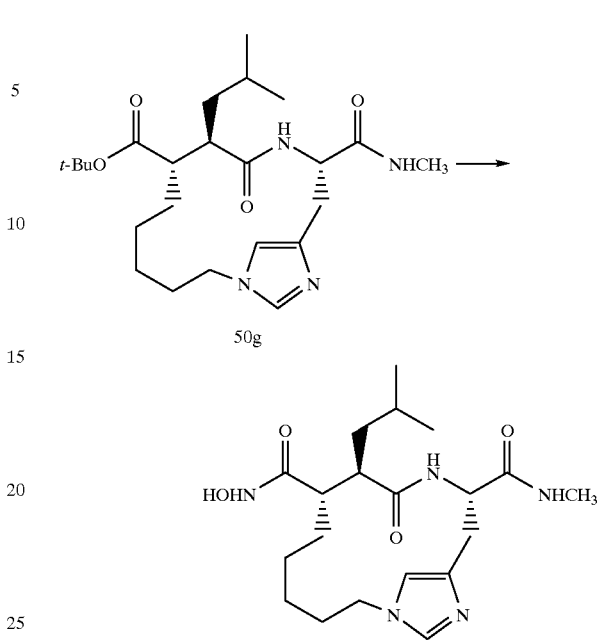

50g

The desired compound was prepared according to the method of Examples 1F and G, except substituting 50 g for 1f. $^1$H NMR(300 MHz, DMSO-d6) δ 0.75 (d, 3H, J=6.2 Hz), 0.81 (d, 3H, J=6.2 Hz), 0.80 (m, overlaped, 4H), 1.14 (m, 1H), 1.22–1.52 (m, 4H), 1.56–1.80 (m, 2H), 2.24–2.47 (m, 2H), 2.58 (d, 3H, J=5.1 Hz), 2.63–2.79 (m, 2H), 3.63–3.76 (m, 1H), 3.87–3.96 (m, 1H), 4.35–4.48 (m, 1H), 6.92 (s, 1H), 7.46 (bs, 2H), 8.12 (d, 1H, J=15 Hz), 8.735 (d, 1H, J=1.5 Hz), 10.36(d, 1H, J=1.5 Hz). MS(DCI/NH$_3$), m/e 408 (M+H)$^+$. [α]$_D$=+10.4° (c=0.25, EtOH).

EXAMPLE 51

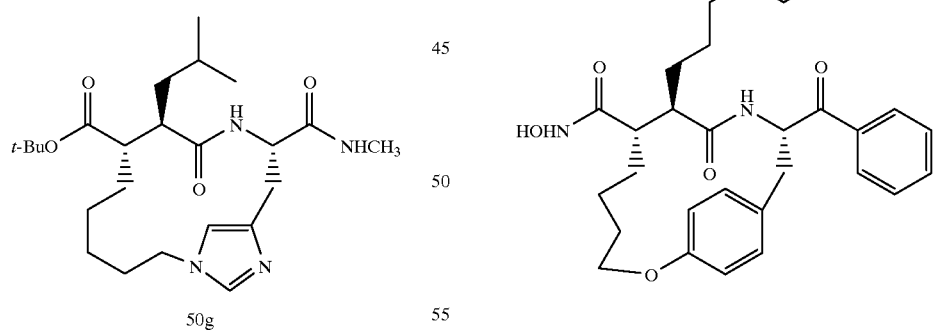

The compound was prepared using the method of Example 43, except substituting succinate ester 5 for 7 and substituting ketone 14b for 43a. mp 211–212° C. $^1$H NMR (300 MHz, DMSO-d$_6$) δ -0.38 (m, 1H), 0.64 (m, 1H), 0.81 (m, 1H), 0.98 (m, 4H), 1.58 (m, 1H), 1.62 (m, 1H), 1.80 (dt, 1H), 2.00 (m, 2H), 2.18 (m, 1H), 2.21 (s, 3H), 2.81 (t, 1H), 3.07 (dd, 1H), 4.04 (m, 2H), 5.73 (m, 1H), 6.69 (d, 2H), 6.93 (m, 4H), 7.17 (dd, 1H), 7.38 (dd, 1H), 7.51 (t, 2H), 7.64 (t, 1H), 8.11 (m, 3H), 8.68 (s, 1H), 10.38 (s, 1H). MS (DCI/NH$_3$) m/e 543 (M+H)$^+$. Anal. calcd for C$_{33}$H$_{38}$N$_2$O$_5$.0.75 H$_2$O: C, 71.26; H, 7.16; N, 5.04. Found: C, 71.03; H, 7.09; N, 5.16.

EXAMPLE 52

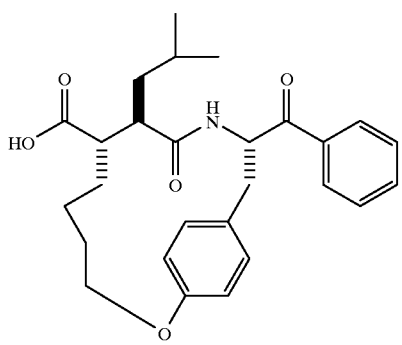

The desired compound was prepared by following the procedures described in Examples 1A–C and 1F starting with succinate ester 7 and ketone 14b. $^1$H NMR (300 MHz, DMSO-d$_6$) δ 8.14–8.11 (d, 1H, J=9.8 Hz), 8.05–8.03 (d, 2H, J=7.2 Hz), 7.66–7.64 (m, 1H), 7.54–7.51 (m, 2H), 7.41–7.38 (m, 1H), 7.21–7.18 (m, 1H), 6.98–6.89 (m, 2H), 5.82–5.75 (m, 1H), 4.13–3.99 (m, 2H), 3.15–3.09 (m, 1H), 2.87–2.79 (m, 1H), 2.00–1.91 (m, 2H), 1.69–1.67 (m, 1H), 1.59–1.58 (m, 1H), 1.3–0.06 (mm, 7H), 0.55–0.37 (m, 7H), (−) 0.25–(−)0.33 (m, 1H). MS (APCI) m/e 450 (M−H)$^-$, 452 (M+H)$^+$, 486 (M+Cl)$^-$.

EXAMPLE 53

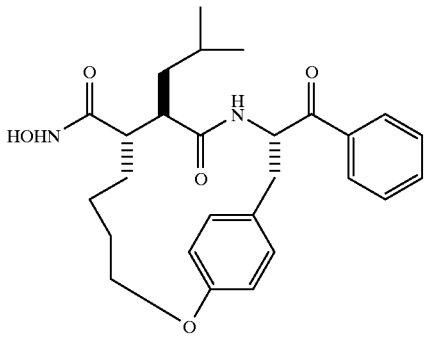

The desired compound was prepared by according to the method of Example 1G, except substituting acid 52 for 1a. $^1$H NMR (300 MHz, DMSO-d$_6$) δ 10.1 (s, 1H), 8.50 (s, 1H), 7.92–7.85 (m, 3H), 7.52–7.47 (m, 1H), 7.39–7.34 (m, 2H), 7.27–7.24 (m, 1H), 7.09–7.06 (m, 1H), 6.82–6.74 (m, 1H), 3.95–3.90 (m, 1H), 3.00–2.92 (m, 1H), 2.72–2.64 (m, 1H), 1.88–1.80 (m, 1H), 1.59–1.52 (m, 3H), 0.94–0.47 (bm, 5H), 0.46–0.23 (mm, 6H), (−)0.55–(−)0.57 (m, 1H). MS (DCI/NH$_4$) m/e 467 (M+H)$^+$. Anal. Calcd for: C$_{27}$H$_{34}$N$_2$O$_5$.0.25H$_2$O: C, 68.84; H, 7.38; N, 5.94. Found: C, 68.53; H, 7.38; N, 5.66.

EXAMPLE 54

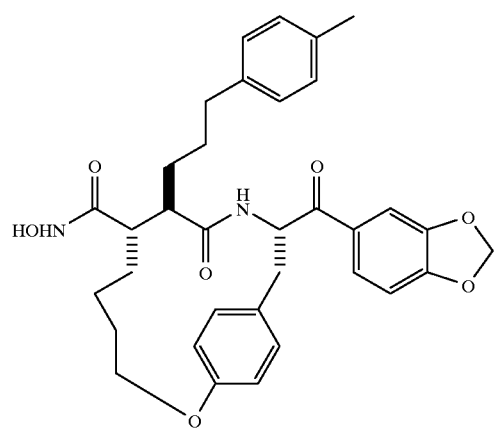

EXAMPLE 54A

The desired compound was prepared according to the method of Example 40A except substituting 4-bromo-1,2-(methylenedioxy)benzene for 4-bromothioanisole.

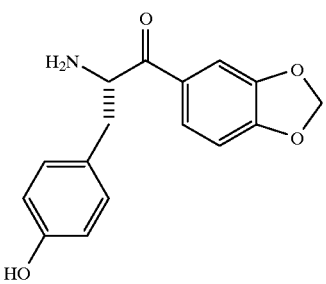

54a

EXAMPLE 54B

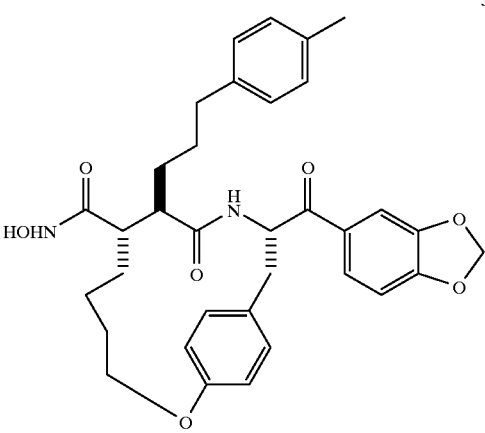

54b

The desired compound was prepared according to the method of Example 43, except substituting succinate 5 for 7 and ketone 54a for 43a. $^1$H NMR (300 MHz, DMSO-d$_6$) δ 10.36 (s, 1H), 8.70 (s, 1H), 8.16–8.13 (d, 1H, J=9.5 Hz), 7.80–7.77 (d, 1H, J=7.7), 7.55 (s, 1H), 7.36–7.33 (d, 1H, J=6.6 Hz), 7.11–7.13 (d, 1H, J=8.1 Hz), 7.02–6.99 (d, 1H, J=8.4 Hz), 6.96–6.87 (m, 4H), 6.62–6.60 (d, 2H, J=8.1 Hz), 6.10–6.08 (d, 2H, J=4.1 Hz), 5.64–5.60 (m, 1H), 4.06–4.03 (m, 2H), 3.04–2.98 (m, 1H), 2.87–2.78 (m, 1H), 2.21 (s, 3H), 2.07–1.96 (m, 3H), 1.84–1.80 (m, 2H), 1.70–1.60 (m, 1H), 1.60–1.52 (m, 1H), 1.05–0.96 (bm, 4H), 0.87–0.80 (m, 1H), 0.64–0.60 (m, 1H), (–)0.37–(–) 0.38 (m, 1H). MS (ESI) m/e 587 (M+H)$^+$, 585 (M–H)$^-$. Anal. Calcd for: $C_{34}H_{38}N_2O_7 \cdot 0.25H_2O$: C, 69.07; H, 6.59; N, 4.70. Found: C, 68.72; H, 6.41; N, 4.64.

EXAMPLE 55

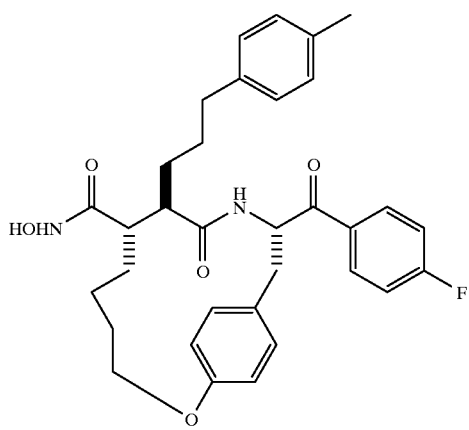

EXAMPLE 55A

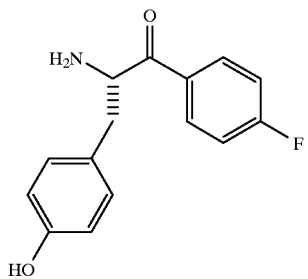

55a

The desired compound was prepared according to the method of Example 40A, except substituting 4-bromofluorobenze for 4-bromothioanisole.

EXAMPLE 55B

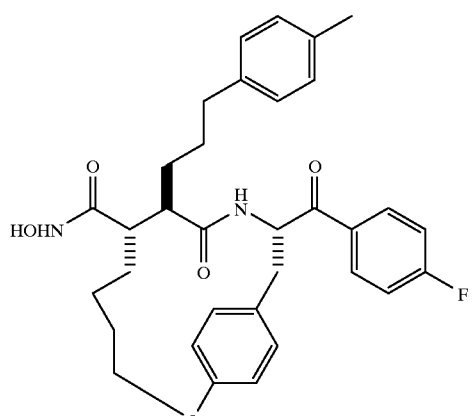

The desired compound was prepared according to the method of Example 43, except substituting succinate 5 for 7 and ketone 55a for 43a. $^1$H NMR (300 MHz, DMSO-d$_6$) δ 10.38 (s, 1H), 8.71 (s, 1H), 8.19–8.13 (m, 3H), 7.37–7.28 (m, 3H), 7.17–7.11 (d, 1H, J=7.3 Hz), 6.95–6.88 (m, 4H), 6.59–6.57 (d, 2H, J=7.1 Hz), 5.73–5.65 (m, 2H), 4.06–4.03 (m, 2H), 3.08–3.03 (m, 1H), 2.89–2.73 (m, 2H), 2.21 (s, 3H), 2.18–2.17 (m, 1H), 2.06–1.99 (m, 2H), 1.82–1.76 (m, 1H), 1.64–1.55 (m, 2H), 1.09–0.59 (bm, 9H), (–)0.382–(–) 0.385 (m, 1H). MS (ESI) m/e 561 (M+H)$^+$, 559 (M–H)$^-$. Anal. Calcd for: $C_{33}H_{37}FN_2O_5 \cdot 0.25H_2O$: C, 70.13; H, 6.68; N, 4.95. Found: C, 70.01; H, 6.59; N, 5.05.

EXAMPLE 56

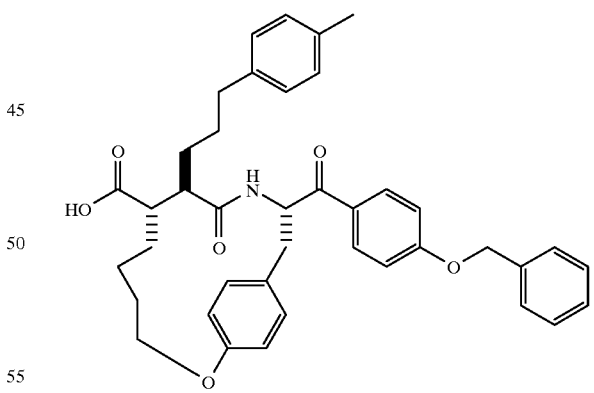

EXAMPLE 56A

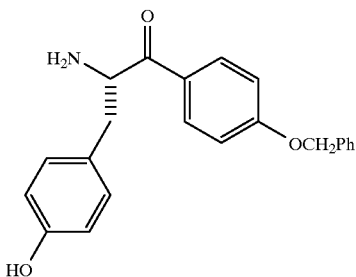

56a

The desired compound was prepared according to the method of example 40A except substituting 4-benzyloxybromobenzene for 4-bromothioanisole.

EXAMPLE 56B

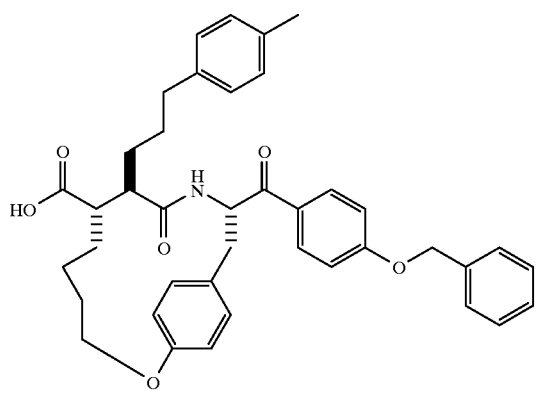

The desired compound was prepared by following the procedures described in Examples 1A–C and 1F starting with succinate ester 5 and ketone 56a. $^1$H NMR (300 MHz, DMSO-d$_6$) δ 8.21–8.18 (d, 1H, J=9.6 Hz), 8.10–8.07 (d, 2H, J=9.1 Hz), 7.44–7.31 (m, 6H), 7.16–7.11 (m, 3H), 6.96–6.88 (m, 4H), 6.64–6.61 (d, 2H, J=7.8 Hz), 5.69–5.65 (m, 1H), 5.18 (s, 2H), 4.08–4.07 (m, 2H), 3.07–3.01 (m, 1H), 2.87–2.78 (m, 1H), 2.19 (s, 3H), 2.20–1.98 (m, 3H), 1.71–1.53 (m, 2H), 1.17–0.86 (mm, 7H), −0.20–(−) 0.41 (m, 1H). MS (DCI/NH4) m/e 634 (M+H)$^+$.

EXAMPLE 57

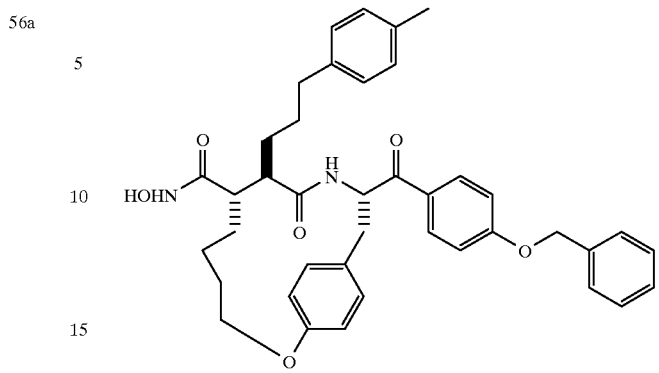

The desired compound was prepared by according to the method of Example 1G, except substituting acid 56 for 1a. $^1$H NMR (300 MHz, DMSO-d$_6$) δ 10.38 (s, 1H), 8.70 (s, 1H), 8.16–8.14 (m, 3H), 7.47–7.38 (m, 6H), 7.21–7.18 (m, 3H), 6.96–6.91 (m, 3H), 6.65–6.63 (d, 2H, J=7.8 Hz), 5.75–5.65 (m, 1H), 5.21 (s, 2H), 4.11–4.08 (m, 2H), 3.10–3.04 (m, 1H), 2.90–2.81 (m, 1H), 2.23 (s, 3H), 2.13–2.01 (m, 2H), 1.88–1.87 (m, 1H), 1.77–1.65 (m, 2H), 1.07–0.96 (m, 6H), 0.70–0.66 (m, 2H), (−)0.29–(−)0.32 (m, 1H).

EXAMPLE 58

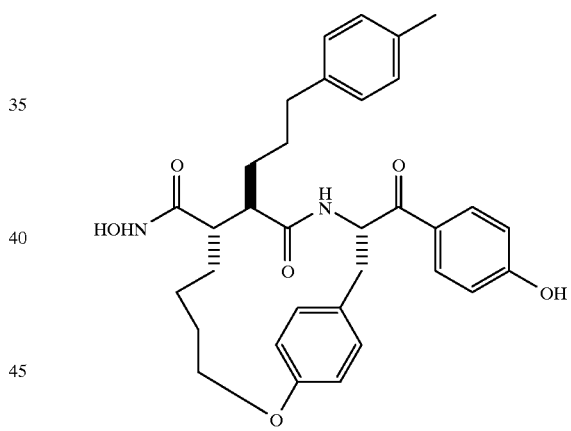

The desired compound was prepared by removing the benzyl group of example 57 using to the procedure described in Example 1D. $^1$H NMR (300 MHz, DMSO-d$_6$) δ 10.42 (s, 1H), 10.35 (s, 1H), 8.69 (s, 1H), 8.11–8.08 (d, 1H, J=9.6 Hz), 8.03–8.00 (d, 2H, J=8.4 Hz), 7.36–7.33 (d, 1H, J=8.4 Hz), 7.17–7.11 (d, 1H, J=8 Hz), 6.94–6.84 (m, 6H), 6.63–6.61 (d, 2H, J=8.1 Hz), 5.66–5.59 (m, 1H), 4.06–4.00 (m, 2H), 3.03–2.97 (m, 1H), 2.84–2.76 (m, 1H), 2.12 (s, 3H), 2.08–1.96 (m, 2H), 1.82–1.78 (m, 1H), 1.63–1.55 (m, 2H), 1.04–0.61 (mm, 6H), (-)0.21–(-) 0.41 (m, 1H). MS (DCI/NH4) m/e 559 (M+H). Anal. Calcd for: $C_{33}H_{38}N_2O_6 \cdot 0.25H_2O$: C, 70.37; H, 6.89; N, 4.97. Found: C, 70.20; H, 6.94; N, 4.86.

EXAMPLE 59

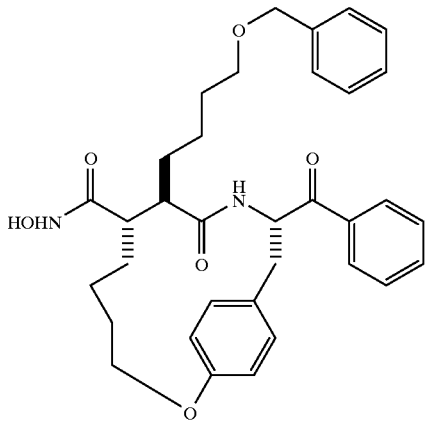

The desired compound was prepared according to the method of Example 43, except substituting succinate 8 for 7 and ketone 14b for 43a. $^1$H NMR (300 MHz, DMSO-$d_6$) δ 10.31 (s, 1H), 8.65 (s, 1H), 8.12–8.08 (d, 2H, J=9.8 Hz), 8.06–8.03 (d, 2H, J=7.1 Hz), 7.59–7.54 (m, 1H), 7.48–7.43 (m, 2H), 7.38–7.22 (m, 7H), 7.18–7.14 (m, 1H), 6.95–6.87 (m, 2H), 5.75–5.69 (m, 1H), 4.29 (s, 2H), 4.07–4.03 (m, 2H), 3.13–3.07 (m, 1H), 2.98–2.75 (m, 3H), 1.93–1.88 (m, 1H), 1.82–0.56 (mm, 15H), (-) 0.036–(-) 0.030 (m, 1H). MS (ESI) 573 (M+H)$^+$, 571 (M-H)$^-$. Anal. Calcd for: $C_{34}H_{40}N_2O_6$: C, 71.30; H, 7.04; N, 4.89. Found: C, 71.16; H, 7.14; N, 4.85.

EXAMPLE 60

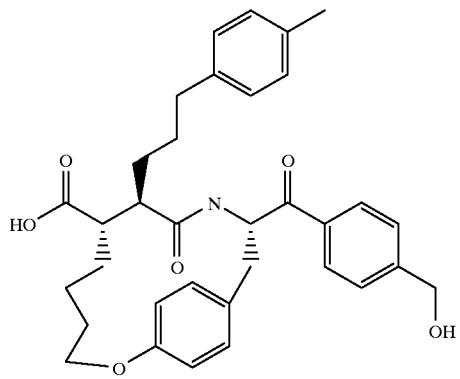

EXAMPLE 60A

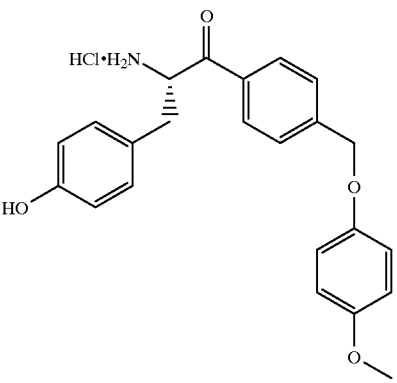

The desired compound was prepared according to the method of Example 40A, except substituting 4-benzyloxymethyl bromobenzene for 4-bromothioanisole.

EXAMPLE 60B

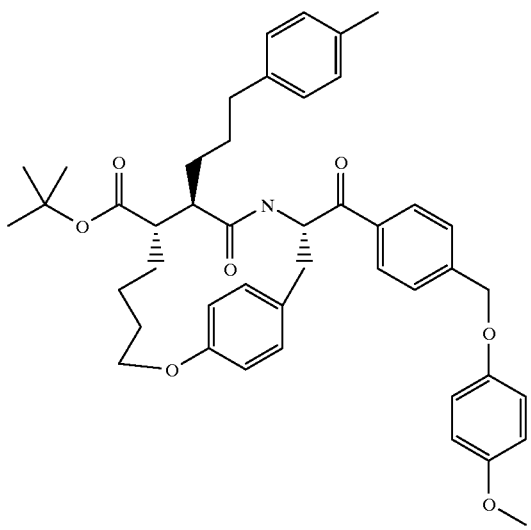

The desired compound was prepared according to the methods of Examples 1A, coupling succinate 5 with ketone 60A, followed by deprotection of the silyl ether as in Example 32B and subsequent cyclization as in Example 1C. MS (DCI/NH$_3$) m/e 720 (M+H).

EXAMPLE 60C

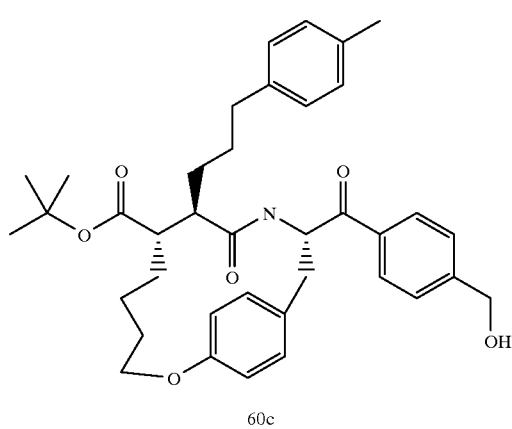

60c

A solution of ester 60b (0.050 g, $7.0 \times 10^{-2}$ mmol) in 4:1 $CH_3CN/H_2O$ (5 mL) was treated with ceric ammonium nitrate (0.19 g, $3.5 \times 10^{-1}$ mmol) and stirred and 1.5 h. The solution was partitioned between ethyl acetate and water, the organic layer was dried ($MgSO_4$) and concentrated to a solid. The solid was purified on silica gel with 25% ethyl acetate/hexane ramped to 60% to provide 0.0 g(26%) of 60c.

EXAMPLE 60D

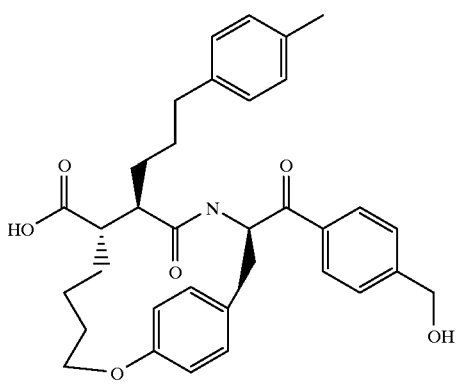

The desired compound was prepared according to the methods of Examples 1F, except substituting 60c for 1f. $^1H$ NMR (d6-DMSO) δ 8.21 (d, 1H, J=10.3 Hz), 8.13 (d, 2H, J=8.5 Hz), 7.59 (d, 2H, J=8.1 Hz), 7.38 (dd, 1H, J=1.4, 8.1 Hz), 7.15 (dd, 1H, J=1.8, 8.1 Hz), 7.02–6.87 (m, 4H), 6.61 (d, 2H, J=8.1 Hz), 5.83–5.69 (m, 1H), 5.48 (s, 2H), 4.07 (t, 1H, J=1.5 Hz), 3.10 (dd, 2H, J=3.7, 13.6 Hz), 2.86–2.72 (m, 2H), 2.30–1.93 (m, 2H), 2.21 (s, 3H), 1.77–1.49 (m, 2H), 1.20–0.79 (m, 7H), 0.70–0.55 (m, 2H), −0.16—−0.32 (m, 1H). MS (ESI) m/e 558 (M+H).

EXAMPLE 61

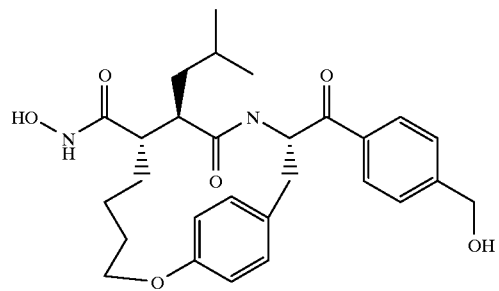

EXAMPLE 61A

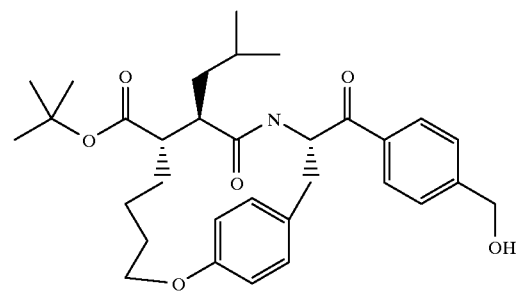

61a

The desired compound was prepared according to the methods of Examples 1A–C, coupling succinate 1 with ketone 60A, followed by deprotection of the benzyl ether as in Example 60C.

EXAMPLE 61B

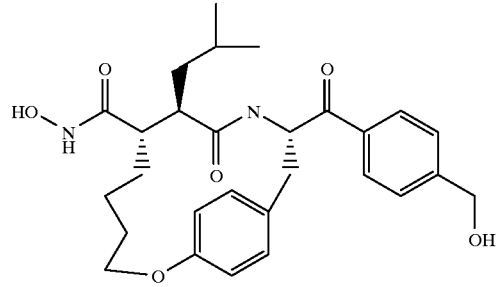

The desired compound was prepared according to the methods of Examples 1F–G, substituting ester 60c for 1f. $^1H$ NMR (300 MHz, DMSO-$d_6$) δ 10.29 (d, 1H, J=1.7 Hz), 8.64 (d, 1H, J=1.7 Hz), 8.02–7.98 (m, 3H), 7.46–7.38 (m, 3H), 7.22 (dd, 1H, J=8.1, 2 Hz), 6.96–6.88 (m, 2H), 5.80–5.68 (m, 1H), 5.34 (t, 1H, J=5.8 Hz), 4.57 (d, 2H, J=5.4 Hz), 4.05 (t, 2H, J=4.7 Hz), 3.10 (dd, 1H, J=13.5, 4.4 Hz), 2.79 (t, 1H, J=12.9 Hz), 2.05–1.94 (m, 1H), 1.77–1.46 (m, 3H), 1.13–0.54 (m, 6H), 0.48 (dd, 6H, J=45.1, 5 Hz), −0.34–0.50 (m, 1H). MS (ESI) m/e 497 (M+H)$^+$. Anal. Calcd for: $C_{28}H_{36}N_2O_6 \cdot 1.25H_2O$: C, 64.78; H, 7.47; N, 5.39. Found: C, 64.44; H, 7.23; N, 5.43.

EXAMPLE 62

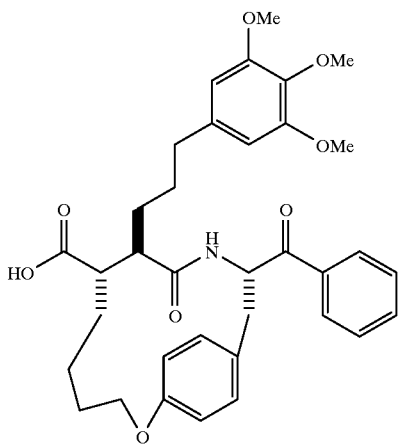

EXAMPLE 62A

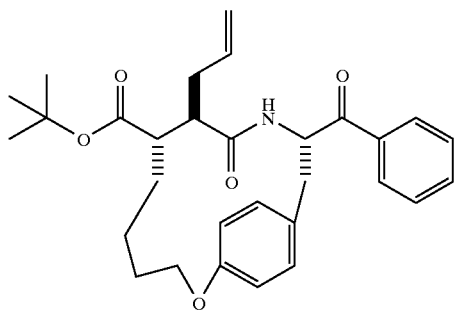

62a

The desired compound was prepared according to the methods of Examples 1A, coupling succinate 9 with ketone 14b, followed by deprotection of the silyl ether as in Example 32B and subsequent cyclization as in Example 1C.

EXAMPLE 62B

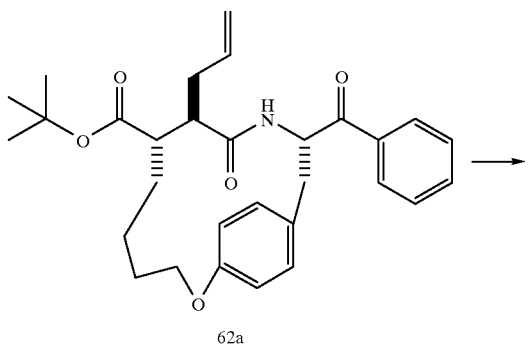

62a

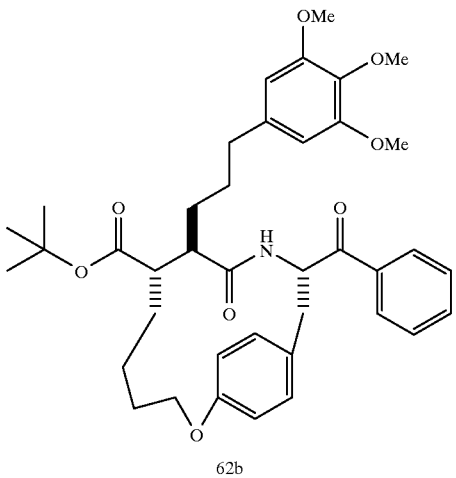

62b

A solution of macrocycle olefin 62a (1.544 g, 3.14 mmol) in THF (10 mL) at 0° C. under argon atmosphere was treated with 9-BBN (19.5 mL of 0.5 M solution in THF, 9.75 mmol) dropwise and stirred at 0° C. for 0.2 h then at ambient temperature for 5.0 h. The resulting solution was treated with DMF (80 mL), [1,1'-Bis(diphenylphosphino)-ferrocene]dichloropalladium(II), complex with dichloromethane (1:1) (0.30 g, 0.37 mmol), 3,4,5-trimethoxybromobenzene (2.41 g, 9.75 mmol), and cesium carbonate (6.14 g, 18.84 mmol) and stirred at 60° C. for 6 h then at ambient temperature for 10 h. The solution was partitioned between ether and water, the organic layer was dried (MgSO$_4$), and concentrated to an oil. The oil was purified on silica gel with ethyl acetate/hexane, 1:2 to provide 0.86 g (42%) of 62b. MS (ESI) m/e 660 (M+H)$^+$.

EXAMPLE 62C

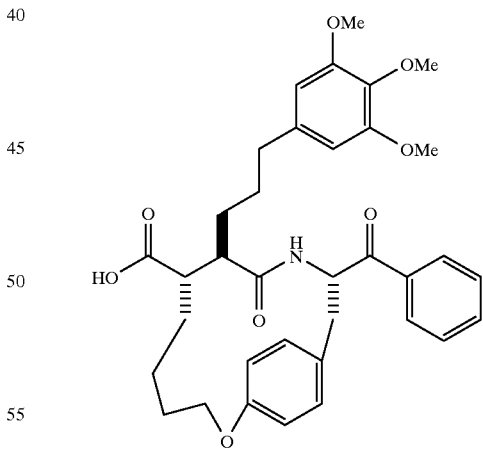

The desired compound was prepared according to the methods of Example 1F, except substituting 62b for 1f. $^1$H NMR (300 MHz DMSO-d$_6$) δ 12.08 (s,1H), 8.25 (d, 1H, J=9.3 Hz), 8.07 (d, 2H, J=7.4 Hz), 7.66–7.61 (m, 1H), 7.53–7.48 (m,2H), 7.42 (d, 1H, J=8.1 Hz), 7.18 (d, 1H, J=8.1 Hz), 6.99–6.91 (m, 2H), 6.22 (s, 2H), 5.76 (m, 1H), 4.04–4.11 (m, 2H), 3.69 (s, 6H), 3.59 (s, 3H), 3.10–3.18 (m, 1H), 2.75 (t, 1H, J=12.3 Hz), 1.98–2.30 (m, 4H), 1.53–1.74 (m, 2H), 0.80–1.21 (m, 6H). 0.58–0.74 (m, 1H), −0.16—

0.30 (m, 1H). MS (ESI) m/e 604 (M+H)⁺. Anal. Calcd for: C₃₅H₄₁NO₈·0.25H₂O: C, 69.11; H, 6.87; N, 2.30. Found: C, 69.01, H, 6.90; N, 2.22.

EXAMPLE 63

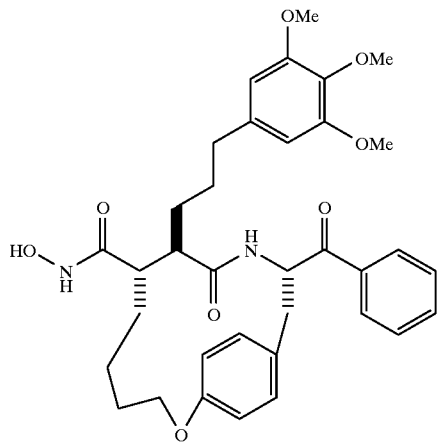

The desired compound was prepared by according to the method of Example 1G, except substituting Example 62 62 for 1a. ¹H NMR (300 MHz, DMSO-d6) δ 10.38 (s, 1H), 8.71 (s, 1H), 8.20 (d, 1H, J=9.6 Hz), 8.08 (d, 2H, J=7.3 Hz), 7.60–7.67 (m, 1H), 7.47–7.52 (m, 2H), 7.42 (d, 1H, J=8.5 Hz), 7.20 (d, 1H, J=8.1 Hz), 6.90–6.97 (m, 2H), 6.21 (s, 2H), 5.66–5.77 (m, 1H), 3.99–4.11 (m, 2H), 3.69 (s, 6H), 3.59 (s, 3H), 3.09–3.17 (m, 1H), 2.73 (t, 1H, J=12.9 Hz), 1.98–2.29 (m, 3H), 1.74–1.84 (m, 1H), 1.50–1.70 (m, 2H), 0.59–1.13 (m, 7H), -0.31—0.44 (m, 1H).MS (ESI) m/e 619 (M+H)⁺. Anal. Calcd for:C₃₅H₄₂N₂O₈: C, 67.94; H, 6.84; N, 4.52. Found: C, 67.65; H, 6.75; N, 4.43.

EXAMPLE 64

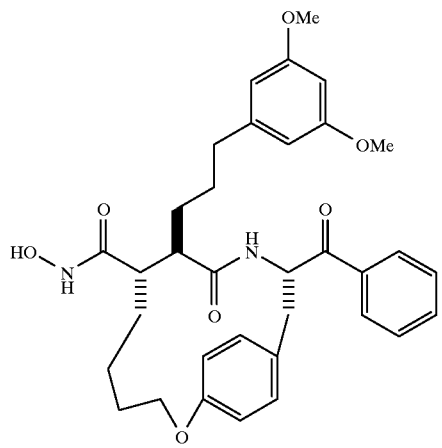

The desired compound was prepared according to the method of Examples 62–63, except substituting 3,5-dimethoxy-bromobenzene for 3,4,5-trimethoxy-bromobenzene in Example 62B. ¹H NMR (300 MHz, DMSO-d6) δ 10.37 (s, 1H), 8.70 (s, 1H), 8.17 (d, 1H, J=9.9 Hz), 8.07 (d, 2H, J=7.4 Hz), 7.58–7.66 (m, 1H), 7.44–7.51 (m, 2H), 7.40 (dd, 1H, J=8.4, 2 Hz), 7.18 (dd, 1H, J=8.1, 2 Hz), 6.88–6.97 (m, 2H), 6.23 (t, 1H, J=2 Hz), 6.05 (d, 2H, J=2.3 Hz), 5.66–5.77 (m, 1H), 4.02–4.08 (m, 2H), 3.67 (s, 6H), 3.07–3.16 (m, 1H), 2.76 (t, 1H, J=12.6 Hz), 2.14–2.28 (m, 1H), 1.95–2.10 (m, 2H), 1.75–1.85 (m, 1H), 1.49–1.72 (m, 2H), 0.56–1.11 (m, 7H), -0.31—0.44 (m, 1H). MS (ESI) m/e 589 (M+H)⁺. Anal. Calcd for: C₃₄H₄₀N₂O₇: C, 69.36; H, 6.84; N, 4.75. Found: C, 69.27; H, 6.63; N, 4.61.

EXAMPLE 65

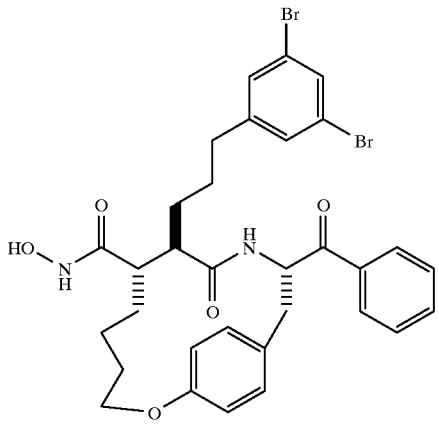

The desired compound was prepared according to the method of Examples 62–63, except substituting 1,3,5-tribromobenzene for 3,4,5-trimethoxy-bromobenzene in Example 62B. ¹H NMR (300 MHz, DMSO-d6) δ 0.38 (s, 1H), 8.72 (s, 1H), 8.17 (d, 1H, J=9.6 Hz), 8.07 (d, 2H, J=7.7 Hz), 7.55–7.61 (m, 2H), 7.35–7.47 (m, 3H), 7.13–7.19 (m, 1H), 7.06 (d, 2H, J=1.8 Hz), 6.88–6.97 (m, 2H), 5.68–5.79 (m, 1H), 4.03–4.10 (m, 2H), 3.08–3.16 (m, 1H), 2.85 (t, 1H, J=12.7 Hz), 2.22–2.35 (m, 1H), 1.91–2.10 (m, 2H), 1.75–1.85 (m, 1H), 1.46–1.75 (m, 2H), 0.57–1.16 (m, 7H), -0.30—0.43 (m, 1H). MS (ESI) m/e 687 (M+H)+. Anal. Calcd for: C32H34N2O5Br2: C, 55.99; H, 4.99; N, 4.08. Found: C, 56.14; H, 4.97; N, 4.01.

EXAMPLE 66

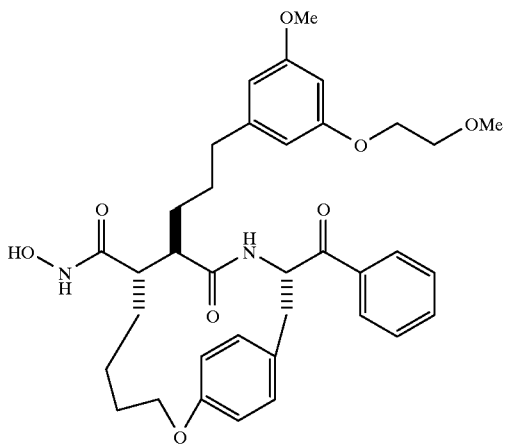

EXAMPLE 66A

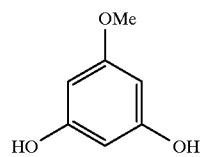

66a

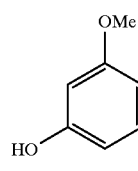

A solution of 5-methoxyresorcinol (2.52 g, 18 mmol) in DMF (25 mL) at ambient temperature was treated with K2CO3 (9.94 g, 72 mmol) and 2-bromoethyl methyl ether (1.72 mL, 18 mmol) and heated at 50° C. for 16 h. The suspension was partioned between Et2O and water, the organic layer was dried (MgSO4), and concentrated to the crude product. Purification on silica gel with ethyl acetate/hexane, 1:4 provided 1.26 g (35%) of the title compound. MS (ESI) m/e 199 (M+H)+.

EXAMPLE 66B

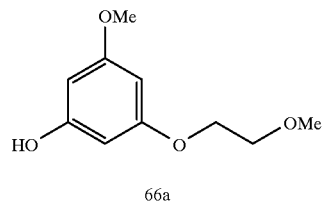

66a

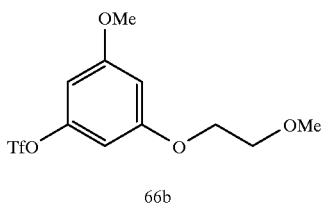

66b

The desired compound was synthesized following the procedure described in *J.Org. Chem.* 141, 4102 (1976). MS (DCI/NH3) m/e 287 (M+H)+.

EXAMPLE 66C

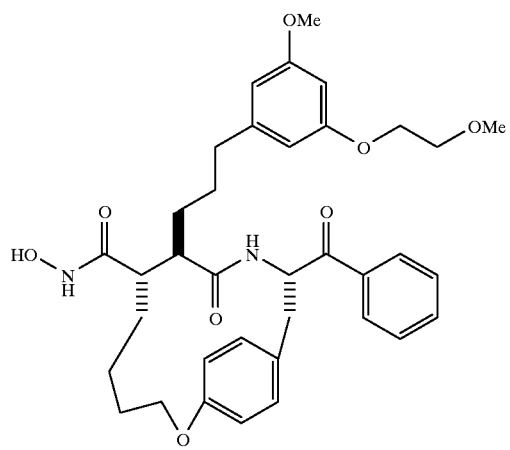

The desired compound was prepared according to the method of Examples 62–63, except substituting 66b for 3,4,5-trimethoxy-bromobenzene in Example 62B. $^1$H NMR (300 MHz, DMSO-d6) δ 10.35 (s, 1H), 8.66 (s, 1H), 8.13 (d, 1H, J=9.6 Hz), 8.07 (d, 2H, J=7.5 Hz), 7.57–7.66 (m, 1H), 7.46–7.51 (m, 3H), 7.15–7.21 (m, 1H), 6.87–6.97 (m, 2H), 6.22–6.25 (m, 1H), 6.02–6.07 (m, 2H), 5.65–5.75 (m, 1H), 4.02–4.09 (m, 2H), 3.96–4.02 (m, 2H), 3.67 (s, 3H), 3.59–3.64 (m, 2H), 3.30 (s, 3H), 3.07–3.16 (m, 1H), 2.76 (t, 1H, 12.9 Hz), 2.11–2.38 (m, 1H), 1.94–2.10 (m, 2H), 1.73–1.85 (m, 1H), 1.48–1.72 (m, 2H), 0.58–1.10 (m, 7H), –0.30––0.44 (m, 1H). MS )ESI) m/e 633 (M+H)+. Anal. Calcd for: C36H44N2O8.H2O: C, 66.44; H, 7.12; N, 4.30. Found: C, 66.40; H, 6.97; N, 4.31.

EXAMPLE 67

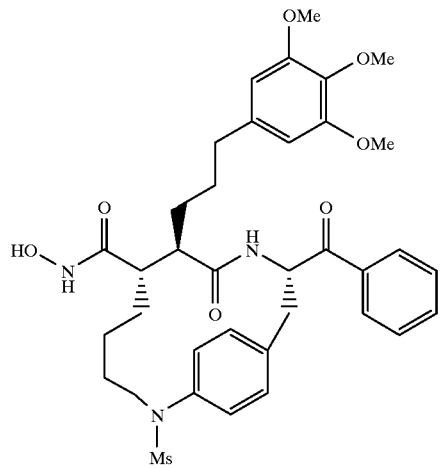

EXAMPLE 67A

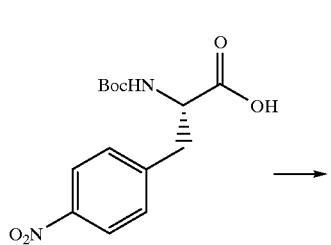

The described compound 67a was prepared according to the method of Example 16A except substituted methylarnine hydrochloride with N,O-dimetheylhydroxyamine hydrochloride.

EXAMPLE 67B

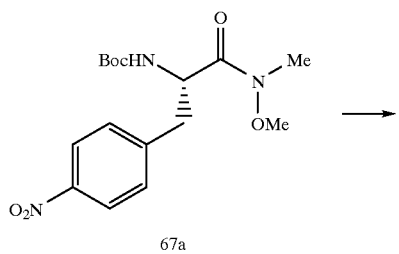

A solution of 67a (0.52 g, 0.35 mole) and Pd/C (52 mg) in EtOH (10 mL) was stirred under $H_2$ for 2 hours, stirred for 30 minutes. The reaction mixture was filtered through Celite and the residue was washed thoroughly with 10% methanol-$CH_2Cl_2$. The filtrate and washings were collected and evaporated to dryness to give 0.47 g of 67b as a off white solid (99%).

Examlple 67C

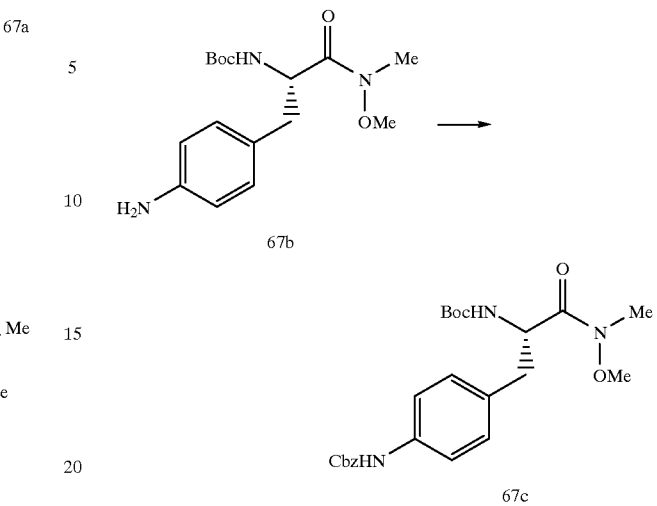

A solution of 67b (0.47 g, 1.46 mmole) in $Et_2O$ (10 mL) at room temperature was treated with saturated aqeoud $NaHCO_3$ (10 mL), stirred for 10 minutes, treated with benzyl chloroformate (0.25 mL, 1.75 mmol), stirred for 2 hours. The mixture was partitioned between water and ether, the aqueous layer was separated and extracted twice with ether. The etheral layer (50 mL) were combined, dried ($MgSO_4$) and concentrated to provide 610.7 mg (92%) of 67c.

EXAMPLE 67D

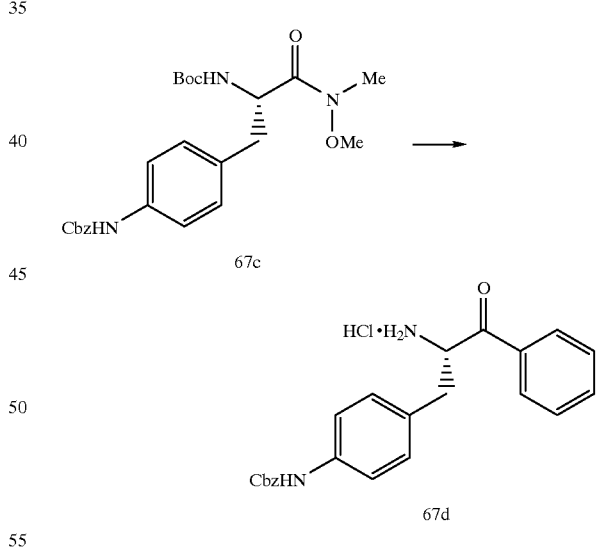

A solution of Example 67c (1.67 g, 3.65 mmole) in THF (40 mL) at −78° C. was treated with phenyllithium (1.8 M in $Et_2O$ and cyclohexane, 7.0 mL, 36.6 g, 1.08 mole). The mixture was warmed to −15° C., stirred for 2 hours, and then quenched with saturated ammonium chloride. The mixture was partitioned between EtOAc and brine, the aqueous layer was separated and extracted three times with EtOAc. The combined organic extracts (100 mL) were dried ($MgSO_4$), and concentrated to an oil. The oil was purified on silica gel with 10–40% EtOAc/hexane to provide 1.17 g (67%) product which was taken up in HCl-dioxane (4N, 10 mL) and stirred for 3 hours. The resulting slurry was diluted with Et₂O (200 mL), filtered and dried under vaccum to give 1.0 g 67d as a white solid (98%).

EXAMPLE 67E

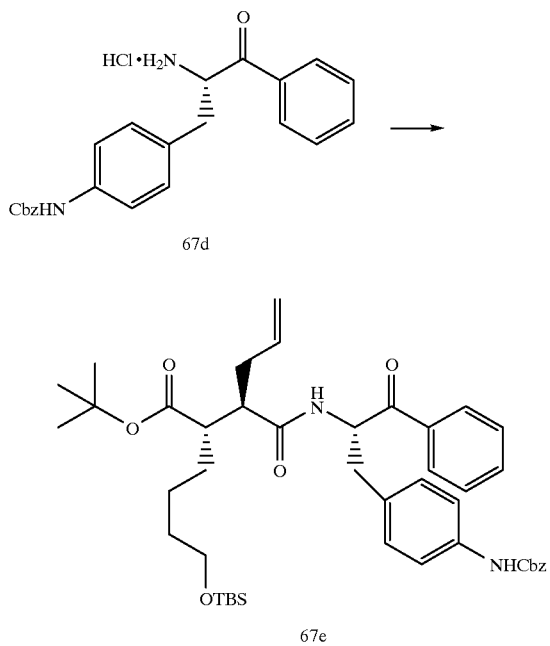

67d

67e

The desired compound 67e was prepared according to the methods of Examples 2A. coupling succinate 9 with ketone 67d.

EXAMPLE 67F

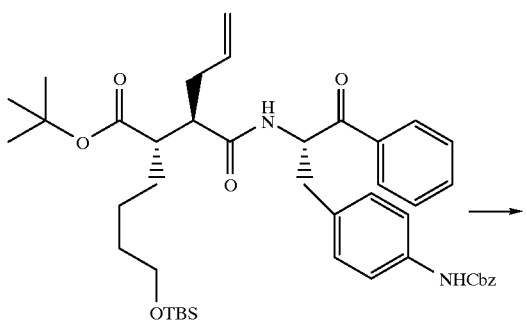

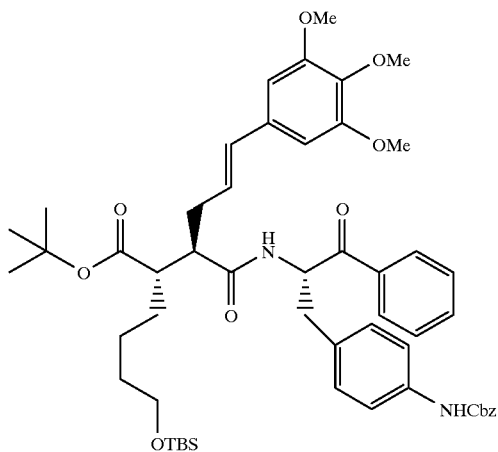

A mixture of Example 67e (0.46 g, 0.608 mmol), P(o-tol)₃ (37.0 mg, 0.122 mmol), Pd(OAc)2 (14.7 mg, 0.061 mmol) and 3,4,5-trimethoxy bromobenzene (224.4 mg, 0.912 mmol) in acetonitrile (8 mL) under Ar was heated at 75° C. for 14 hours. The mixture was evaporated to dryness and purified on silica gel with 10–40% EtOAc/hexane to provide 511 mg (91%) of 67f.

EXAMPLE 67G

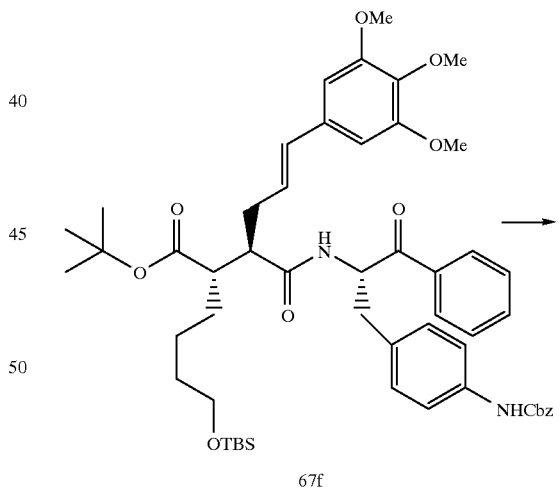

67f

139
-continued

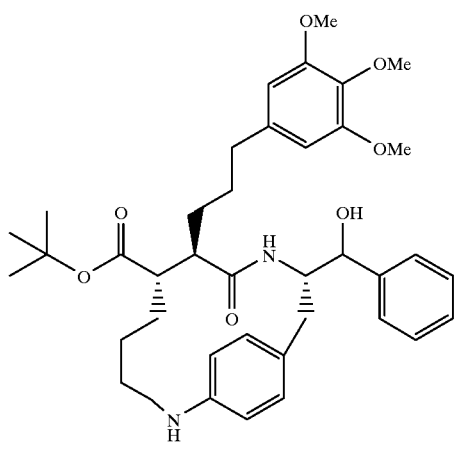
67g

The desired compound was prepared according to the previous methods. Deprotecion of the silyl ether as in Example 32B and subsequent cyclization as in Example 17 A–B.

EXAMPLE 67H

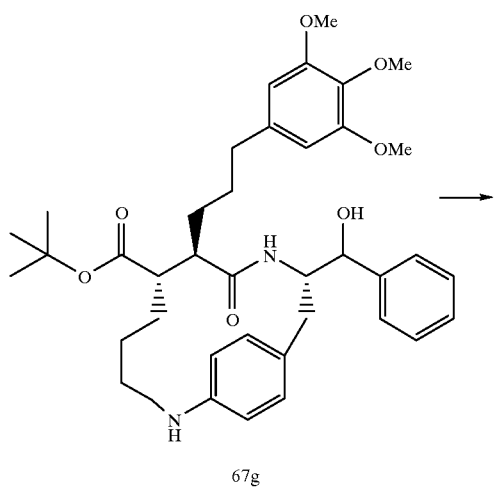
67g

140
-continued

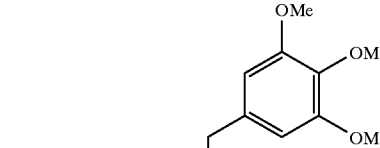

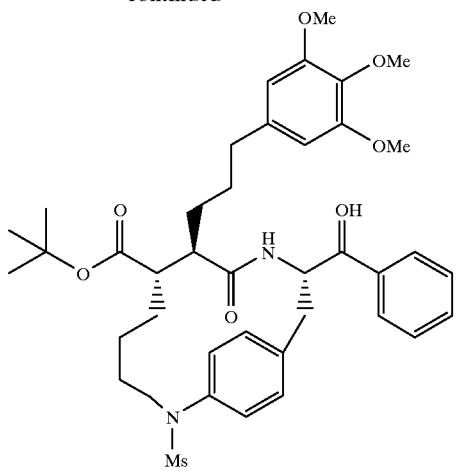
67h

A solution of Example 67 g (65.3 mg, 0.099 mole) in CH$_2$Cl$_2$ (4 mL) at 0° C. was treated with pyridine (0.032 mL, 0.39 mmol) followed by (0.018 mL, 0.24 mol), warmed to room temperature for 7 hours. The mixture was poured into CH$_2$Cl$_2$ and washed with brine and saturated aqueous NaHCO$_3$. The organic layer was dried (MgSO$_4$) and concentrated to give 73 mg of 67h as an oil.

EXAMPLE 67I

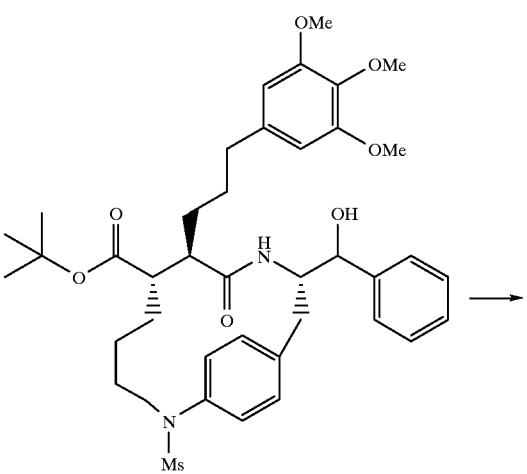
67h

-continued

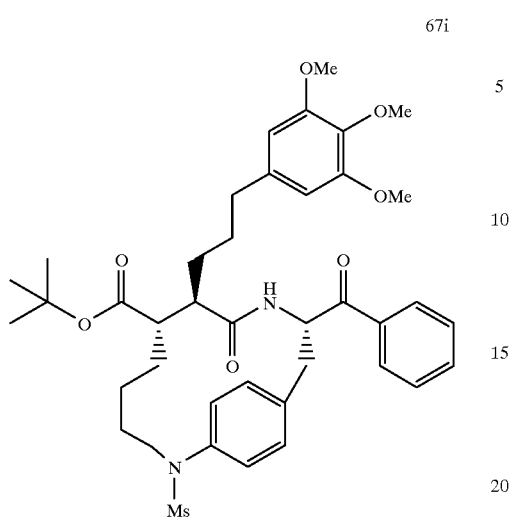

67i

A solution of 67h (73 mg, 0.099 mmol) in CH₂Cl₂ (10 mL) room temperature was treated with Dess-Martin reagent (46.1 mg) stirred for 1 hour. The mixture was partitioned between water and CH₂Cl₂, the aqueous layer was separated and extracted twice with CH₂Cl₂. The combined organic extracts were washed with aqueous NaHCO₃ and brine, dried (MgSO₄), and concentrated to an oil. The oil was purified on silica gel with 10–40% EtOAc/hexane to provide 39.1 mg (53.7% for the last two steps) product.

EXAMPLE 67J

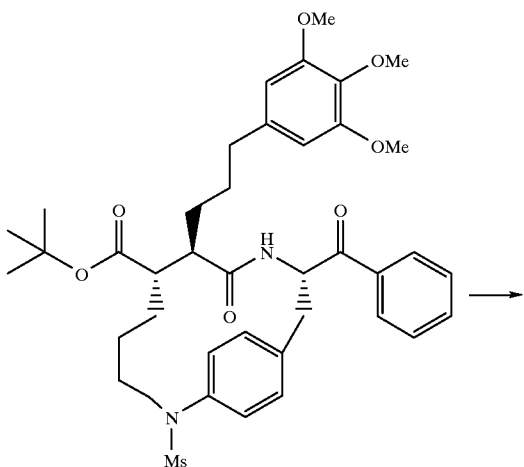

-continued

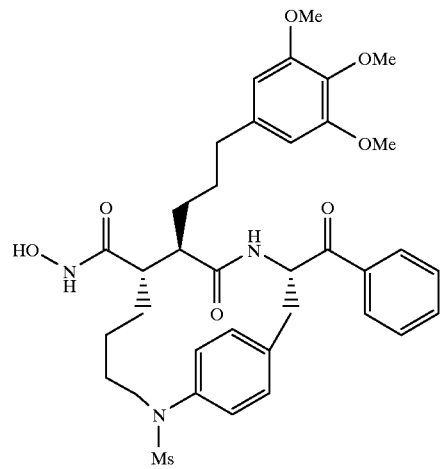

The desired compound was prepared by the methods of Examples 1F and G, except substituting for 1F. $^1$H NMR (300 MHz, DMSO-d₆) δ −0.48 (m, 1H), 0.6–0.8 (m, 5H), 1.35–1.81 (m, 3H), 2.0–2.62 (m, 4H), 2.73 (m, 1H), 2.80 (t, 1H, J=12.5 Hz), 3.05 (s, 3H), 3.19 (dd, 1H, J1=12.5 Hz, J2=4.5 Hz), 3.59 (s, 3H), 3.69 (s, 6H), 3.73–3.77 (m, 2H), 5.73 (m, 1H), 6.23 (s, 2H), 7.45 (d, 1H, J=8.6 Hz), 7.32–7.39 (m, 2H), 7.51 (t, 2H, J=7.6 Hz), 7.56 (d, 1H, J=8.6 Hz), 7.64 (t, 1H, J=7.6 Hz), 8.08 (d, 2H, J=7.6 Hz), 8.29 (d, 1H, J=9.0 Hz), 8.71 (s, 1H), 10.37 (s, 1H); MS (ESI) m/e 718 (M+Na)⁺, 696 (M+H)⁺.

We claim:

1. A compound of formula

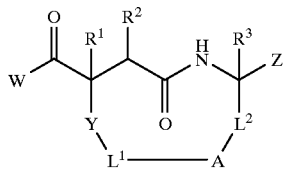

or a pharmaceutically acceptable salt, prodrug or ester thereof wherein

W is NHOH or OH;

R¹ and R³ are independently selected from hydrogen or alkyl of one to four carbon atoms;

R² is selected from the group consisting of
  (a) alkyl of one to ten carbon atoms,
  (b) alkenyl of two to ten carbon atoms,
  (c) cycloalkyl of three to eight carbon atoms,
  (d) (cycloalkyl)alkyl wherein the cycloalkyl portion is of three to eight carbon atoms, and the alkylene portion is of one to six carbon atoms,
  (e) cycloalkenylene of five to eight carbon atoms,
  (f) (cycloalkenylene)alkyl wherein the cycloalkenylene portion is of five to eight carbon atoms, and the alkylene portion is of one to six carbon atoms,
  (g) phenyl, (h) phenyl substituted with 1, 2, or 3 substituents independently selected from
  alkoxyalkyloxy,
  alkyl of one to four carbon atoms,
  alkoxy of one to four carbon atoms,
  halogen,
  haloalkyl of one to four carbon atoms,
  cyano,
  cyanoalkyl,
  —$CO_2R^4$ wherein $R^4$ is independently selected at each occurrence from hydrogen and alkyl of one to four carbon atoms, and
  —$CONR^4R^5$ wherein $R^4$ is defined above and and $R^5$ is independently selected at each occurrence from hydrogen and alkyl of one to four carbon atoms,
(i) phenylalkyl wherein the alkylene portion is of one to six carbon atoms,
(j) phenylalkyl wherein the alkylene portion is of one to six carbon atoms and the phenyl ring is substituted with 1, 2, or 3 substituents independently selected from
  alkoxyalkyloxy,
  alkyl of one to four carbon atoms,
  alkoxy of one to four carbon atoms,
  halogen,
  haloalkyl of one to four carbon atoms,
  cyano,
  cyanoalkyl,
  —$CO_2R^4$,
  —$CONR^4R^5$,
  phenyl, and
  phenyl substituted with 1, 2, or 3 substituents independently selected from
    alkyl of one to four carbon atoms,
    hydroxy,
    alkoxy of one to four carbon atoms,
    halogen,
    haloalkyl of one to four carbon atoms,
    cyano,
    cyanoalkyl,
    —$CO_2R^4$, and
    —$CONR^4R^5$,
(k) —$(CH_2)_m$—T—$(CH_2)_n$-$R^6$ wherein m and n are independently 0, 1, 2, 3 or 4,
  T is O or S, and
  $R^6$ is selected from the group consisting of
    alkyl of one to four carbon atoms,
    phenyl, and
    phenyl substituted with 1, 2, or 3 substituents selected from
      alkoxyalkyloxy,
      alkyl of one to four carbon atoms,
      hydroxy,
      alkoxy of one to four carbon atoms,
      halogen,
      haloalkyl of one to four carbon atoms,
      cyano,
      cyanoalkyl,
      —$CO_2R^4$,
      —$CONR^4R^5$,
      phenyl, and
      phenyl substituted with 1, 2, or 3 substituents independently selected from
        alkyl of one to four carbon atoms,
        alkoxy of one to four carbon atoms,
        halogen,
        haloalkyl of one to four carbon atoms,
        cyano,
        cyanoalkyl,
        —$CO_2R^4$,
        —$CONR^4R^5$, and
(l) fluorenylalkyl wherein the alkylene portion is of one to four carbon atoms.
Y is absent or —O—;
$L^1$ is alkylene of two to six carbon atoms,
$L^2$ is selected from the group consisting of
  (a) alkylene of one to six carbon atoms, and
  (b)

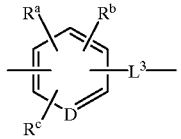

wherein D is CH or N,
  $L^3$ is absent or is alkylene of one to four carbon atoms, and
  $R^a$, $R^b$ and $R^c$ are independently selected from
    hydrogen,
    alkyl of one to four carbon atoms,
    hydroxy,
    alkoxy of one to four carbon atoms,
    halogen,
    haloalkyl of one to four carbon atoms,
    cyano,
    —$SO_2R^{6'}$ wherein $R^{6'}$ is alkyl of one to four carbon atoms,
    —$SO_2NH_2$,
    —$CO_2R^4$,
    2-tetrazolyl, and
    —$CONR^7R^8$ wherein $R^7$ and $R^8$ are independently selected at each occurrence from hydrogen and alkyl of one to four carbon atoms,
    or $R^7$ and $R^8$ together with the N atom to which they are attached define a a 5-or 6-membered heterocyclic ring selected from the group consisting of
      (1) morpholinyl,
      (2) thiomorpholinyl,
      (3) thiomorpholinyl sulfone,
      (4) pyrrolidinyl,
      (5) piperazinyl,
      (6) piperidinyl, and
      (7) 3-ketopiperazine;
A is absent or is selected from the group consisting of
  (a) —O—,
  (b) —$NR^9$— wherein $R^9$ is selected from the group consisting of
    (1) hydrogen,
    (2) alkyl of one to four carbon atoms,
    (3) —$CO_2R^{10}$ wherein $R^{10}$ is independently selected at each occurrence from the group consisting of
      alkyl of one to four carbon atoms,
      haloalkyl of one to four carbon atoms,
      phenyl,
      phenyl substituted with 1, 2, or 3 substituents independently selected from alkyl of one to four carbon atoms,
        alkoxy of one to four carbon atoms,
        halogen,
        haloalkyl of one to four carbon atoms, nitro,
cyano,
cyanoalkyl,
—SO$_2$NH$_2$,
—CO$_2$R$^4$, and
—CONR$^4$R$^5$,
phenylalkyl wherein the alkylene portion is of one to four carbon atoms,
phenylalkyl wherein the alkylene portion is of one to four carbon atoms, and the phenyl ring is substituted with 1, 2, or 3 substituents independently selected from
alkyl of one to four carbon atoms,
alkoxy of one to four carbon atoms,
halogen,
haloalkyl of one to four carbon atoms,
cyano,
cyanoalkyl,
—SO$_2$NH$_2$,
—CO$_2$R$^4$, and
—CONR$^4$R$^5$,
heteroarylalkyl wherein the alkylene portion is of one to four carbon atoms, and the heteroaryl group is selected from
furyl,
pyridyl,
thienyl,
benzimidazolyl,
imidazolyl,
thiazolyl, and
benzothiazolyl wherein the heteroaryl group is unsubstituted or substituted with alkyl of one to four carbon atoms,
(4) —CONR$^7$R$^8$,
(5) —COR$^{10}$, and
(6) —SO$_2$R$^{10}$,
(c) —S(O)$_n$— wherein n is 0, 1, or 2,
(d) —S—S—
(e) —CH=CH—,
(f)

wherein V is O or NOR$^4$,
(g)

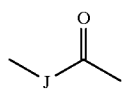

wherein J is O or NR$^4$,
(h)

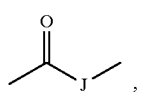

(i)

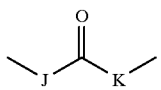

wherein J is defined above and K is selected from O and NR$^4$, provided that J and K are not simultaneously O,
(j)

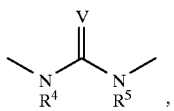

(k)

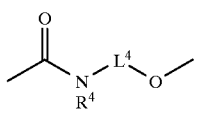

wherein L$^4$ is alkylene of two to six carbon atoms,
(l)

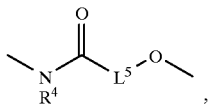

wherein L$^5$ is alkylene of one to three carbon atoms,
(m)

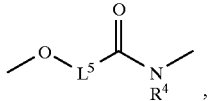

(n)

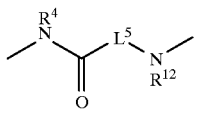

wherein R$^4$ is defined above and R$^{12}$ is selected from
hydrogen,
alkyl of one to four carbon atoms,
—COR$^{10}$
—CO$_2$R$^{10}$, and
—SO$_2$R$^{10}$,
(o)

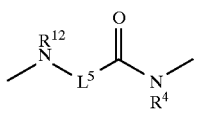

(p)

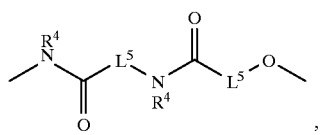

(q)

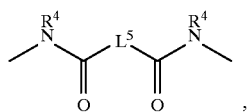

(r)

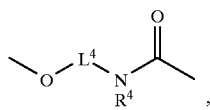

(s)

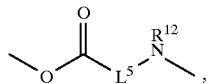

(t)

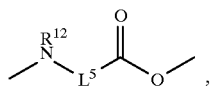

(u)

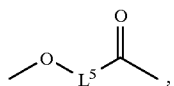

(v)

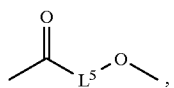

(w) —J'—L$^4$—K'— wherein J' and K' are independently selected from O and NR$^{12}$,
(x) —NR$^4$SO$_2$—,
(y) —SO$_2$NR$^4$—,
(z) —NR$^4$SO$_2$NR$^5$—,
(aa)

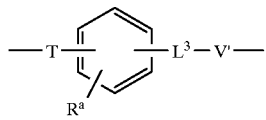

wherein T and V' are independently selected from O and S and R$^a$ is defined above, (bb)

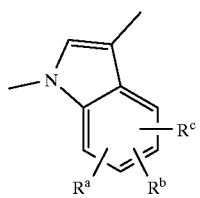

wherein R$^a$, R$^{b\ 1}$, and R$^c$ are defined above, (cc)

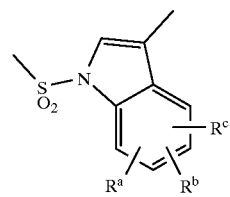

(dd)

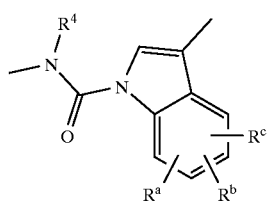

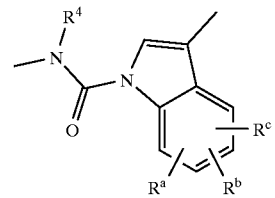

(ee)

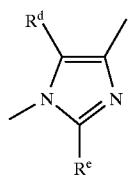

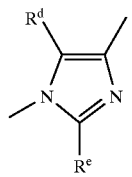

wherein R$^d$ and R$^e$ are independently selected from hydrogen and alkyl of one to four carbon atoms, (ff)

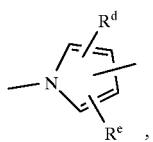

provided that when A is selected from (aa), (bb), (cc), (dd), (ee) and (ff) above, $L^2$ is alkylene,
and further provided that when both Y and A are absent, $L^1$ is alkylene of three to six carbon atoms;

Z is

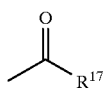

wherein $R^{17}$ is selected from the group consisting of
(1) alkyl of one to six carbon atoms,
(2) carboxyalkyl wherein the alkylene portion is of two to six carbon atoms,
(3) phenyl,
(4) phenyl substituted with 1, 2, or 3 substituents selected from
  alkyl of one to four carbon atoms,
  halogen,
  hydroxy,
  hydroxyalkyl of one to four carbon atoms,
  haloalkyl of one to four carbon atoms,
  alkoxy of one to four carbon atoms,
  amino,
  cyano,
  —$NR^4R^5$,
  —$SO_2NR^4R^5$,
  —$SO_2R^4$,
  —$CH_2NR^7R^8$,
  —$CONR^7R^8$,
  —$CO_2R^4$, benzyloxy
  phenyl, wherein the phenyl ring may be substituted with 1, 2, or 3 substituents independently selected from
    alkyl of one to four carbon atoms, halogen,
    haloalkyl of one to four carbon atoms, and benzyloxy,
(5) 1,3-benzodioxole,
(6) indolyl,
(7) indolyl substituted with
  alkyl of one to four carbon atoms,
  halogen,
  haloalkyl of one to four carbon atoms,
  alkoxy of one to four carbon atoms,
  —$SO_2NR^4R^5$,
  —$CO_2R^{10}$, and
  phenyl, wherein the phenyl ring may be substituted with 1, 2, or 3 substituents independently selected from
    alkyl of one to four carbon atoms, halogen,
    haloalkyl of one to four carbon atoms, and alkoxy of one to four carbon atoms,
(8) pyrrolyl,
(9) pyrrolyl substituted with alkyl of one to four carbon atoms,
(10) imidazolyl,
(11) imidazolyl substituted with alkyl of one to four carbon atoms, provided that in (6)–(11) above, when the heterocycle is attached at a carbon atom, the N atom may bear a substituent selected from the group consisting of
  alkyl of one to six carbon atoms
  —$CONR^7R^8$,
  —$SO_2NR^7R^8$ and
  —$SO_2R^{10}$,
(12) pyridyl,
(13) pyridyl substituted with alkyl of one to four carbon atoms,
(14) thienyl,
(15) thienyl substituted with
  halogen,
  alkyl of one to four carbon atoms, and
  haloalkyl of one to four carbon atoms,
(16) thiazolyl,
(17) thiazolyl substituted with
  halogen,
  alkyl of one to four carbon atoms, and
  haloalkyl of one to four carbon atoms,
(18) oxazolyl,
(19) oxazolyl substituted with
  halogen,
  alkyl of one to four carbon atoms, and
  haloalkyl of one to four carbon atoms,
(20) furyl,
(21) furyl substituted with
  halogen,
  alkyl of one to four carbon atoms, and
  haloalkyl of one to four carbon atoms,
(22) benzofuryl,
(23) benzofuryl substituted with 1, 2, or 3 substituents selected from
  alkyl of one to four carbon atoms,
  halogen, and
  haloalkyl of one to four carbon atoms,
(24) benzothiazolyl,
(25) benzothiazolyl substituted with 1, 2, or 3 substituents selected from
  alkyl of one to four carbon atoms,
  halogen, and
  haloalkyl of one to four carbon atoms,
(26) benzimidazolyl and
(27) benzimidazolyl substituted with 1, 2 or 3 substituents independently selected from
  alkyl of one to four carbon atoms,
  halogen, and
  haloalkyl of one to four carbon atoms.

2. A compound or a pharmaceutically acceptable salt, ester or prodrug thereof as defined by claim 1 of formula

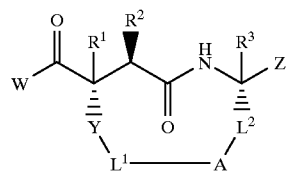

wherein W, $R^2$, $L^2$ and Z are defined therein,
Y is absent or —O—,
$R^1$ and $R^3$ are H,
$L^1$ is alkylene of two to six carbon atoms, and
A is selected from the group consisting of
  (a) —O—,
  (b) —$NR^9$— wherein $R^9$ is selected from the group consisting of (1) hydrogen,
(2) alkyl of one to four carbon atoms,
(3) —CO$_2$R$^{10}$ wherein R$^{10}$ is independently selected at each occurrence from the group consisting of
    alkyl of one to four carbon atoms,
    phenyl,
    phenyl substituted with 1, 2, or 3 substituents independently selected from alkyl of one to four carbon atoms,
        alkoxy of one to four carbon atoms,
        halogen,
        haloalkyl of one to four carbon atoms,
        nitro,
        cyano,
        cyanoalkyl,
        —SO$_2$NH$_2$,
        —CO$_2$R$^4$, and
        —CONR$^4$R$^5$,
    phenylalkyl wherein the alkylene portion is of one to four carbon atoms,
    phenylalkyl wherein the alkylene portion is of one to four carbon atoms, and the phenyl ring is substituted with 1, 2, or 3 substituents independently selected from
        alkyl of one to four carbon atoms,
        alkoxy of one to four carbon atoms,
        halogen,
        haloalkyl of one to four carbon atoms,
        cyano,
        cyanoalkyl,
        —SO$_2$NH$_2$,
        —CO$_2$R$^4$, and
        —CONR$^4$R$^5$, and
    (4) —SO$_2$R$^{10}$,
(c) —CH=CH—,
(d)

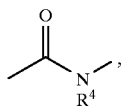

(e)

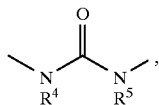

and
(f)

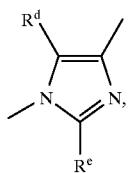

wherein R$^d$ and R$^e$ are independently selected from hydrogen and alkyl of one to four carbon atoms, provided that when A is (f) above, L$^2$ is alkylene.

3. A compound or a pharmaceutically acceptable salt, ester or prodrug thereof as defined by claim 2 wherein R$^2$ is selected from the group consisting of isobutyl, cyclohexyl, cyclopentylmethyl, phenyl, 3-(4-tolyl)propyl, 3-(4-chlorophenyl)propyl, 2-(4-propylphenyl)ethyl, 3-benzyloxypropyl, 4-phenoxybutyl, 4-(4-butylphenoxy)butyl, 4-biphenyloxy, 2-(4-(4'cyano)biphenyloxy)ethyl, 4-benzyloxybutyl, 3-(3,4,5-trimethoxyphenyl)propyl, 3-(3,5-dimethoxyphenyl)propyl, 3-(3,5-dibromophenyl)propyl, and 3-[3-methoxy-5-(2-methoxyethoxy)phenyl]propyl.

4. A compound or a pharmaceutically acceptable salt, ester or prodrug thereof as defined by claim 3 wherein Z is

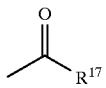

wherein R$^{17}$ is selected from the group consisting of
(1) phenyl,
(2) phenyl substituted with
    alkyl of one to four carbon atoms,
    methanesulfonyl,
    dimethylaminomethyl,
    halogen,
    benzyloxy,
    hydroxy, or
    hydroxyalkyl,
(3) 3-indolyl.
(4) 2-pyrrolyl,
(5) 1,3-benzodioxole.

5. A compound or a pharmaceutically acceptable salt, ester or prodrug thereof as defined by claim 4 of formula

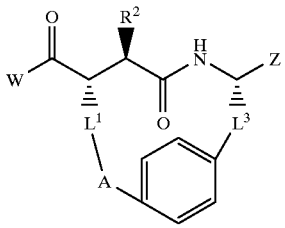

wherein
L$^3$ is absent or methylene and
A is selected from the group consisting of
    (a) —O—,
    (b) —NR$^9$— wherein R$^9$ is selected from
        hydrogen,
        —CO$_2$benzyl,
        —SO$_2$CH$_3$,
        —SO$_2$-(4-tolyl),
    (c) —CH=CH—, and
    (d) —C(O)NH—.

6. A compound or a pharmaceutically acceptable salt, ester or prodrug thereof as defined by claim 5 wherein R$^2$ is selected from isobutyl, 3-(4-tolyl)propyl, 2-(4-propylphenyl)ethyl, 3-(3,4,5-trimethoxyphenyl)propyl, 3-(3,5-dimethoxyphenyl)propyl, 3-(3,5-dibromophenyl)propyl, and 3-[3-methoxy-5-(2-methoxyethoxy)phenyl]propyl;

Z is selected from the group consisting of

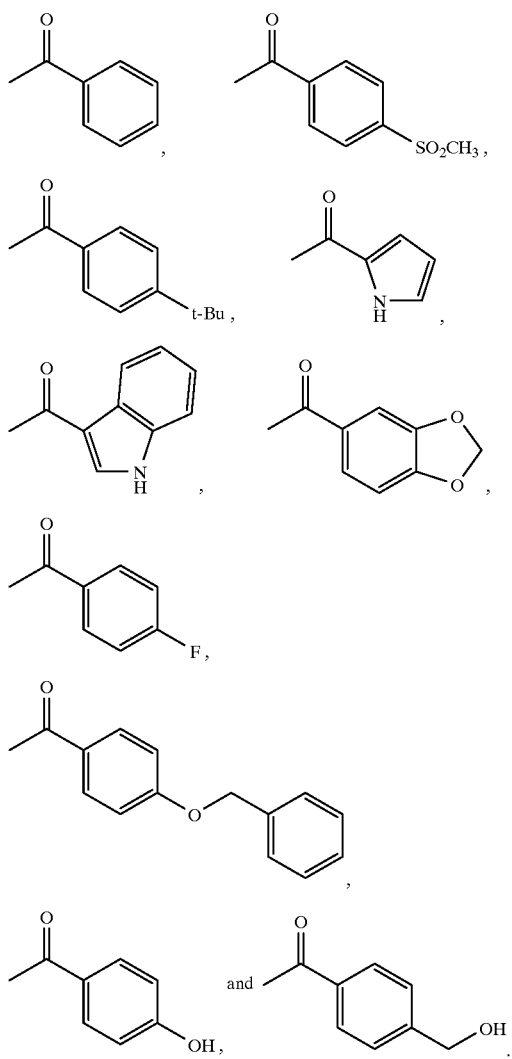

7. A compound or a pharmaceutically acceptable salt, ester or prodrug thereof as defined by claim 6 wherein W is —NHOH and

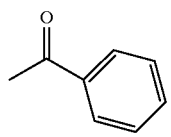

8. A compound or a pharmaceutically acceptable salt, ester or prodrug thereof as defined by claim 4 of formula

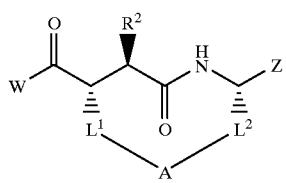

wherein W, $R^2$, and Z are defined therein,
$L^1$ is alkylene of 3–5 carbon atoms,
$L^2$ is alkylene of 1–4 carbon atoms, and
A is selected from the group consisting of
(a) —$NR^9$— wherein $R^9$ is selected from
hydrogen,
—$CO_2$benzyl and
—$SO_2$-(2-nitrophenyl),
(b) —NHCONH—, and
(c)

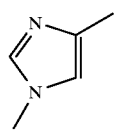

provided that when A is (c), $L^2$ is methylene.

9. A compound or a pharmaceutically acceptable salt, ester or prodrug thereof as defined by claim 8 wherein $R^2$ is selected from isobutyl, 3-(4-tolyl)propyl, 2-(4-propylphenyl)ethyl, 4-benzyloxybutyl, 3-(3,4,5-trimethoxyphenyl)propyl, 3-(3,5-dimethoxyphenyl)propyl, 3-(3,5-dibromophenyl)propyl, and 3-[3-methoxy-5-(2-methoxyethoxy)phenyl]propyl;

Z is selected from the group consisting of

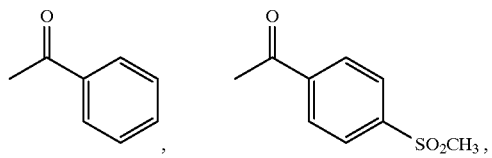

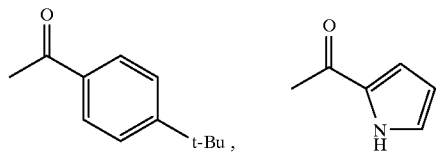

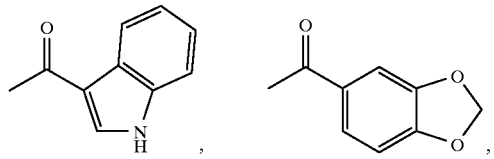

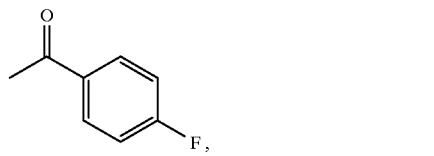

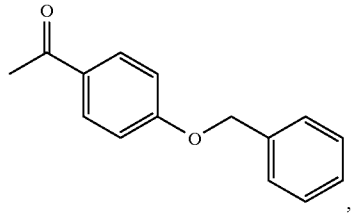

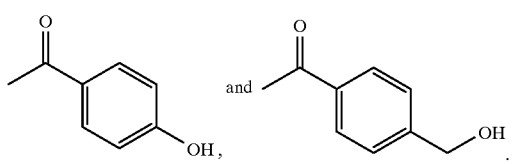
10. A compound or a pharmaceutically acceptable salt, ester or prodrug thereof as defined by claim 9 wherein
W is —NHOH and
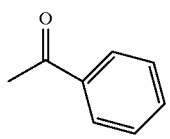
11. A compound or a pharmaceutically acceptable salt, ester or prodrug thereof as defined by claim 1 selected from the group consisting of
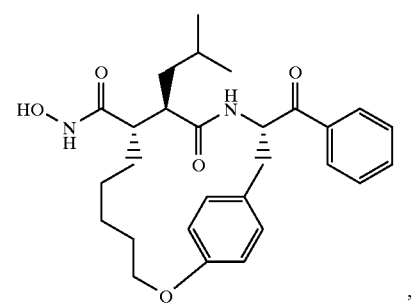
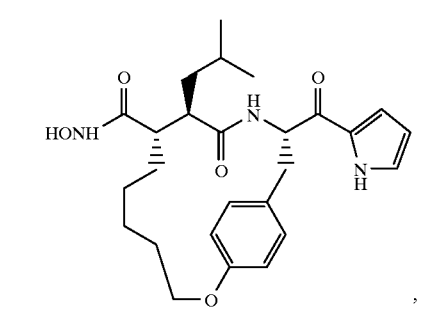
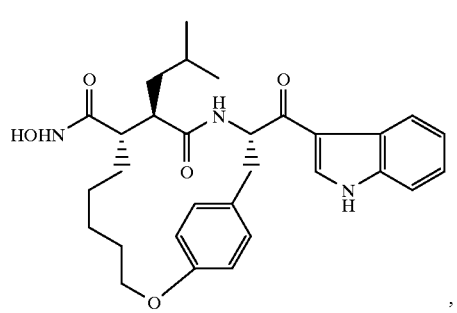
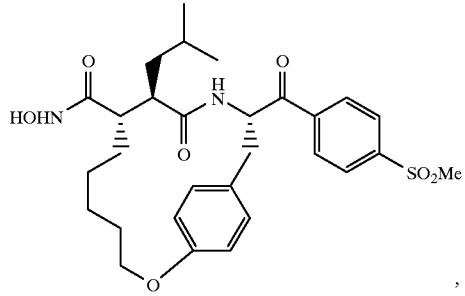
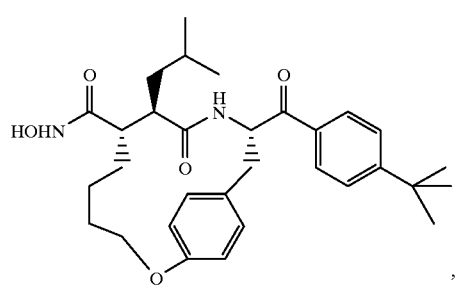
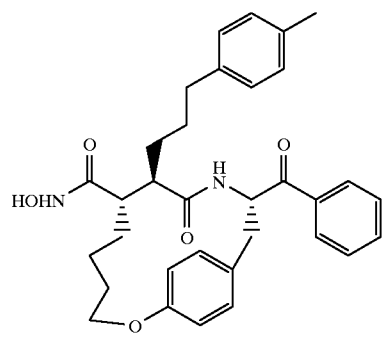
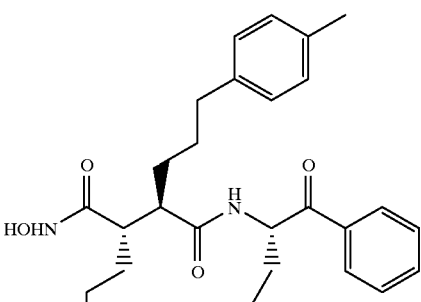
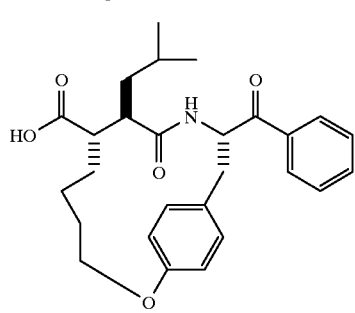

157
-continued
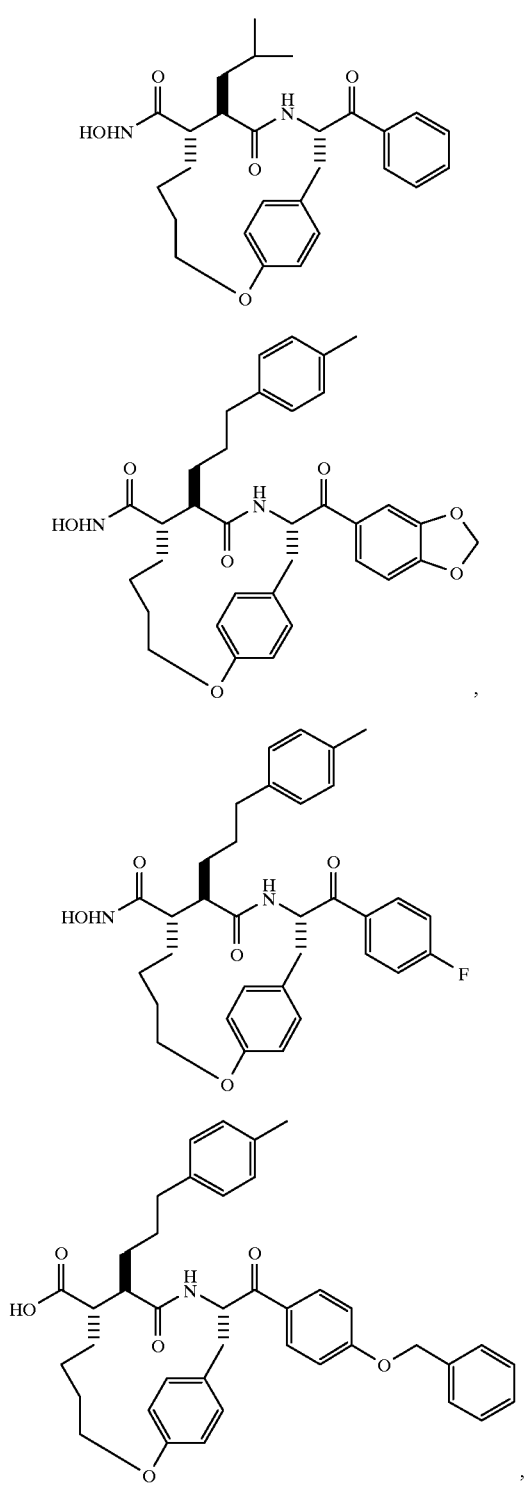
158
-continued
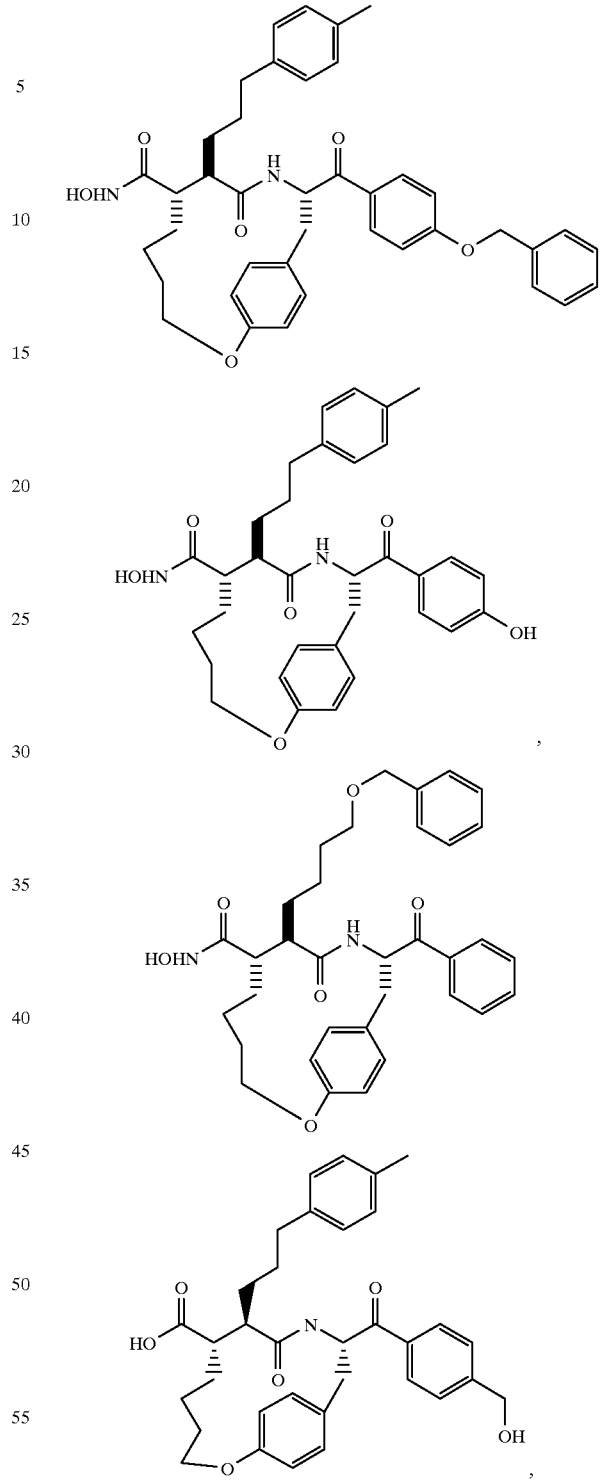

-continued
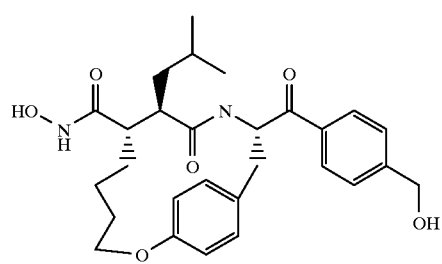
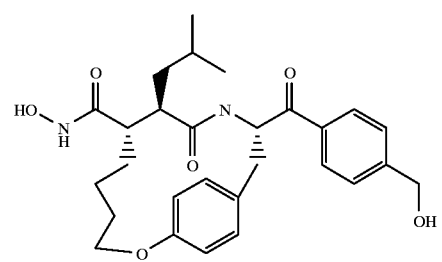
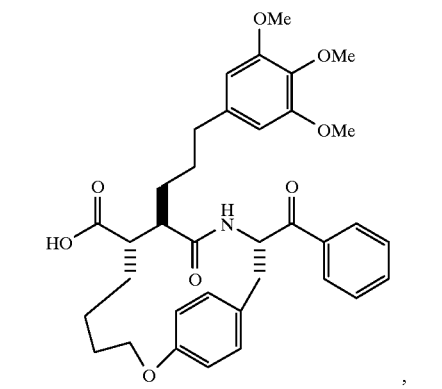
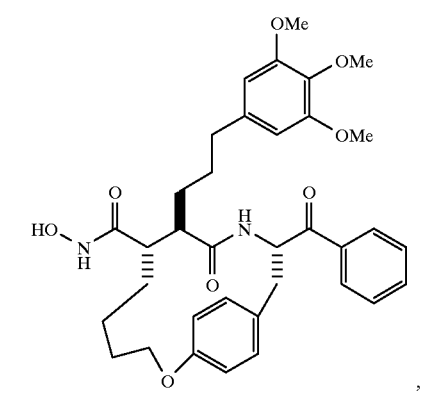
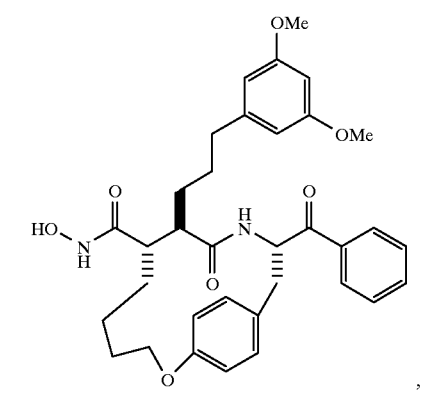
-continued
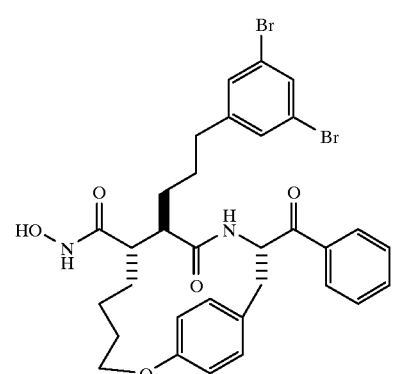
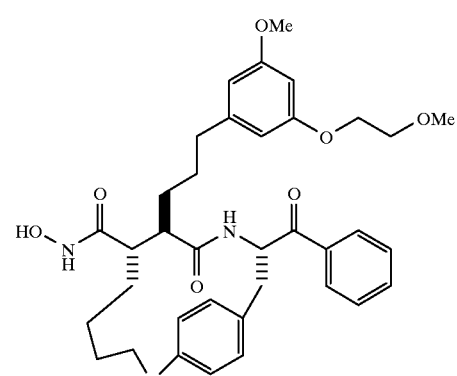
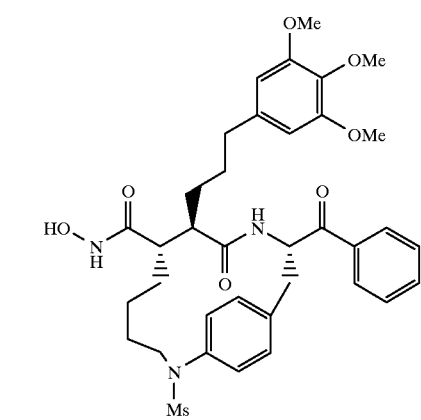

161
-continued

162
-continued

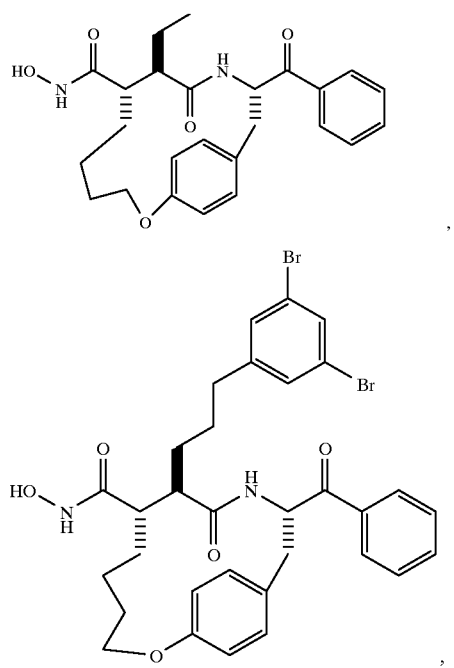

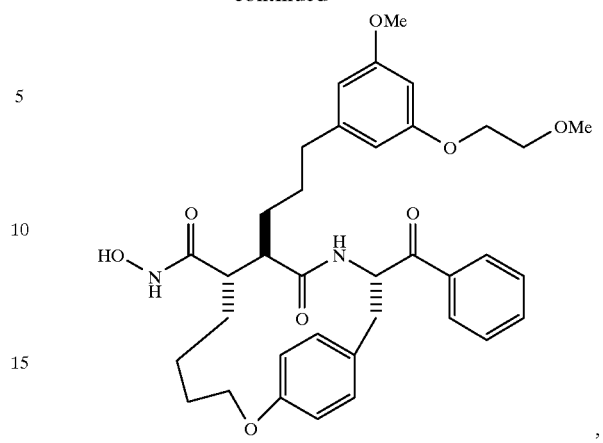

12. A method for inhibiting matrix metalloproteinases in a mammal in need of such treatment, comprising administering to the mammal a therapeutically effective amount of a compound of claim 1.

13. A composition for inhibiting matrix metalloproteinases comprising a pharmaceutical carrier and a therapeutically effective amount of a compound of claim 1.

* * * * *

UNITED STATES PATENT AND TRADEMARK OFFICE
CERTIFICATE OF CORRECTION

PATENT NO. : 5,952,320
DATED : September 14, 1999
INVENTOR(S) : Steven K. Davidsen et al.

It is certified that error appears in the above-identified patent and that said Letters Patent is hereby corrected as shown below:

Col. 153, line 46  Insert -- Z is --

Signed and Sealed this

Eighth Day of August, 2000

Attest:

Attesting Officer

Q. TODD DICKINSON
Director of Patents and Trademarks